(12) United States Patent
Wang et al.

(10) Patent No.: US 8,105,812 B2
(45) Date of Patent: Jan. 31, 2012

(54) LACCASES, COMPOSITIONS AND METHODS OF USE

(75) Inventors: Huaming Wang, Fremont, CA (US); Joseph C. McAuliffe, Sunnyvale, CA (US)

(73) Assignee: Danisco US Inc., Palo Alto, CA (US)

( * ) Notice: Subject to any disclaimer, the term of this patent is extended or adjusted under 35 U.S.C. 154(b) by 794 days.

(21) Appl. No.: 11/954,804

(22) Filed: Dec. 12, 2007

(65) Prior Publication Data

US 2008/0196173 A1 Aug. 21, 2008

Related U.S. Application Data

(60) Provisional application No. 60/875,518, filed on Dec. 18, 2006, provisional application No. 60/875,454, filed on Dec. 18, 2006.

(51) Int. Cl.
*C12N 9/02* (2006.01)
(52) U.S. Cl. ........................ 435/189; 536/23.2
(58) Field of Classification Search .................. 435/189; 536/23.2
See application file for complete search history.

(56) References Cited

U.S. PATENT DOCUMENTS

| | | | |
|---|---|---|---|
| 5,752,980 | A | 5/1998 | Pedersen et al. |
| 5,861,271 | A | 1/1999 | Fowler et al. |
| 7,279,564 | B2 | 10/2007 | De Nobel et al. |
| 7,354,752 | B2 | 4/2008 | Dunn-Coleman et al. |
| 7,413,877 | B2 | 8/2008 | Collier et al. |
| 7,413,887 | B2 | 8/2008 | Dunn-Coleman et al. |
| 2006/0154843 | A1 | 7/2006 | Wang et al. |

FOREIGN PATENT DOCUMENTS

| | | |
|---|---|---|
| EP | 0 238 023 A2 | 9/1987 |
| EP | 0 504 005 B1 | 9/1992 |
| JP | 02238885 A | 9/1990 |
| WO | WO 92/01046 A1 | 1/1992 |
| WO | WO 95/01426 A1 | 1/1995 |
| WO | WO 95/33836 A1 | 12/1995 |
| WO | WO 95/33837 A1 | 12/1995 |
| WO | WO 96/00290 A1 | 1/1996 |
| WO | WO 96/00787 A1 | 1/1996 |
| WO | WO 96/12845 A1 | 5/1996 |
| WO | WO 97/08325 A2 | 3/1997 |
| WO | WO 97/11217 A1 | 3/1997 |
| WO | WO 2005/001036 A2 | 1/2005 |
| WO | WO 2005/093050 A2 | 10/2005 |

OTHER PUBLICATIONS

Michniewicz et al. [Appl. Micrbiol. Biotechnol. (2006) 69: 682-688; Published online: Jun. 28, 2005).*
Altschul, S.F. et al. "Basic local alignment search tool." *J. Mol. Biol* 215(3): 403-410, 1990.
Altschul, S.F. et al. "Gapped BLAST and PSI-BLAST: a new generation of protein database search programs." *Nucleic Acids Res.* 25(17): 3389-3402, 1997.
Lyashenko, A.V. et al. "Purification, crystallization and preliminary X-ray study of the fungal laccase from *Cerrena maxima* ." *Acta Crystallogr Sect F Struct Biol Cryst Commun.* F62(Pt 10): 954-957, Oct. 1, 2006.
Mander, G.J. et al. "Use of Laccase as a Novel, Versatile Reporter System in Filamentous Fungi." *Appl. Environ. Microbiol.* 72(7): 5020-5026, Jul. 1, 2006.
Michniewicz, A. et al. "The white-rot fungus *Cerrena unicolor* strain 137 produces two laccase isoforms with different physico-chemical and catalytic properties." *Applied Microbiology and Biotechnology* 69(6): 682-688, Feb. 11, 2006.
Zhang, M. et al. "Characterization and decolorization ability of a laccase from *Panus rudis*." *Enzyme and Microbial Technology* 39(1): 92-97, Jun. 1, 2006.
Database UniProt. Laccase 1 precursor (EC:1.10.3.2). EBI accession No. UNIPROT:Q2HWK1, Mar. 21, 2006.

* cited by examiner

*Primary Examiner* — Tekchand Saidha

(57) ABSTRACT

Novel laccases, nucleic acid sequences encoding such laccases, and vectors and host cells for expressing the laccases are described. The novel laccase enzymes may be employed in conjunction with mediators to provide an improved method for bleaching denim fabrics.

2 Claims, 10 Drawing Sheets

Figure 7. Bleaching of soluble indigo using a *Thielavia* sp. laccase and a variety of mediators at 50 and 500 uM concentrations.

Figure 8. Bleaching of soluble indigo using a *Thielavia*, *Myceliophthora* and *Cerrena* sp. laccase and a variety of mediators at pH 5.

Figure 9. Bleaching of soluble indigo using a *Thielavia*, *Myceliophthora* and *Cerrena* sp. laccase and a variety of mediators at pH 7.

GC942 Figures (for Examples 7-12)

SEQUENCE LISTING

```
<160> NUMBER OF SEQ ID NOS: 77

<210> SEQ ID NO 1
<211> LENGTH: 2363
<212> TYPE: DNA
<213> ORGANISM: Cerrena unicolor

<400> SEQUENCE: 1
atgagctcaa agctacttgc tcttatcact gtcgctctcg tcttgccact aggcaccgac      60
gccggcatcg gtcctgttac cgacttgcgc atcaccaacc aggatatcgc tccagatggc     120
ttcacccgac cagcggtact agctgggggc acattccctg gagcacttat taccggtcag     180
aaggtatggg agatcaactt ggttgaatag agaaataaaa gtgacaacaa atccttatag     240
ggagacagct tccaaatcaa tgtcatcgac gagcttaccg atgccagcat gttgaccag      300 acatccattg tgagtataat ttaggtccgc tcttctggct atcctttcta actcttaccg     360
tctagcattg gcacggcttc tttcagaagg gatctgcgtg ggccgatggt cctgccttcg     420
ttactcaatg ccctatcgtc accggaaatt ccttcctgta cgactttgat gttcccgacc     480
aacctggtac tttctggtac catagtcact tgtctactca atattgcgat ggtcttcgtg     540
gcccgttcgt tgtatacgat ccaaaggatc ctaataaacg gttgtacgac attgacaatg     600
gtatgtgcat catcatagag atataattca tgcagctact gaccgtgact gatgctgcca     660
```

-continued

| | |
|---|---|
| gatcatacgg ttattaccct ggcagactgg taccacgttc tcgcaagaac tgttgtcgga | 720 |
| gtcgcgtaag tacagtctca cttatagtgg tcttcttact cattttgaca taggacaccc | 780 |
| gacgcaacct tgatcaacgg tttgggccgt tctccagacg ggccagcaga tgctgagttg | 840 |
| gctgtcatca acgttaaacg cggcaaacgg tatgttattg aactcccgat ttctccatac | 900 |
| acagtgaaat gactgtctgg tctagttatc gatttcgtct ggtctccatc tcatgtgacc | 960 |
| ctaattacat cttttctatc gacaaccatt ctatgactgt catcgaagtc gatggtgtca | 1020 |
| acacccaatc cctgaccgtc gattctattc aaatcttcgc aggccaacga tactcgttcg | 1080 |
| tcgtaagtct ctttgcacga ttactgcttc tttgtccatt tctgacctg tttaaacagc | 1140 |
| tccatgccaa ccgtcctgaa acaactatt ggatcagggc caaacctaat atcggtacgg | 1200 |
| atactaccac agacaacggc atgaactctg ccattctgcg atacaacggc gcacctgttg | 1260 |
| cggaaccgca aactgttcaa tctcccagtc tcaccccttt gctcgaacag aaccttcgcc | 1320 |
| ctctcgtgta cactcctgtg gtatgtttca aagcgttgta atttgattgt ggtcattcta | 1380 |
| acgttactgc gtttgcatag cctggaaacc ctacgcctgg cggcgccgat attgtccata | 1440 |
| ctcttgactt gagttttgtg cggagtcaac attcgtaaag ataagagtgt ttctaatttc | 1500 |
| ttcaataata ggatgctggt cgcttcagta tcaacgtgc ctcgttcctt gatcctaccg | 1560 |
| tccccgttct cctgcaaatt ctcagcggca cgcagaatgc acaagatcta ctccctcctg | 1620 |
| gaagtgtgat tcctctcgaa ttaggcaagg tcgtcgaatt agtcatacct gcaggtgtcg | 1680 |
| tcggtggacc tcatccgttc catctccatg gggtacgtaa cccgaactta taacagtctt | 1740 |
| ggacttaccc gctgacaagt gcatagcata acttctgggt cgtgcgaagt gccggaaccg | 1800 |
| accagtacaa ctttaacgat gccattctcc gagacgtcgt cagtatagga ggaaccgggg | 1860 |
| atcaagtcac cattcgtttc gtggtatgtt tcattcttgt ggatgtatgt gctctaggat | 1920 |
| actaaccggc ttgcgcgtat agaccgataa ccccggaccg tggttcctcc attgccatat | 1980 |
| cgactggcac ttggaagcgg gtctcgctat cgtatttgca gagggaattg aaaatactgc | 2040 |
| tgcgtctaat ttaaccccc gtacgcggtt ccctcacat cctggagcta agcagcttac | 2100 |
| taacatacat ttgcagaggc ttgggatgag ctttgcccga agtataacgc gctcagcgca | 2160 |
| caaaagaagg ttgcatctaa gaaaggcact gccatctaat ttttgtaaca acaaggagg | 2220 |
| gtctcttgta cttttattgg gatttctttc ttggggttta ttgttaaact tgactctact | 2280 |
| atgtttggaa gacgaagggg gctcgcgcat ttatatacta tctctcttgg catcacctgc | 2340 |
| agctcaatcc ttcaaccacc taa | 2363 |

<210> SEQ ID NO 2
<211> LENGTH: 523
<212> TYPE: PRT
<213> ORGANISM: Cerrena unicolor

<400> SEQUENCE: 2

Met Ser Ser Lys Leu Leu Ala Leu Ile Thr Val Ala Leu Val Leu Pro
1               5                   10                  15

Leu Gly Thr Asp Ala Gly Ile Gly Pro Val Thr Asp Leu Arg Ile Thr
            20                  25                  30

Asn Gln Asp Ile Ala Pro Asp Gly Phe Thr Arg Pro Ala Val Leu Ala
        35                  40                  45

Gly Gly Thr Phe Pro Gly Ala Leu Ile Thr Gly Gln Lys Gly Asp Ser
    50                  55                  60

Phe Gln Ile Asn Val Ile Asp Glu Leu Thr Asp Ala Ser Met Leu Thr
65                  70                  75                  80

```
Gln Thr Ser Ile His Trp His Gly Phe Phe Gln Lys Gly Ser Ala Trp
                85                  90                  95

Ala Asp Gly Pro Ala Phe Val Thr Gln Cys Pro Ile Val Thr Gly Asn
            100                 105                 110

Ser Phe Leu Tyr Asp Phe Asp Val Pro Asp Gln Pro Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Lys Asp Pro Asn Lys Arg Leu Tyr Asp Ile
145                 150                 155                 160

Asp Asn Asp His Thr Val Ile Thr Leu Ala Asp Trp Tyr His Val Leu
                165                 170                 175

Ala Arg Thr Val Val Gly Val Ala Thr Pro Asp Ala Thr Leu Ile Asn
            180                 185                 190

Gly Leu Gly Arg Ser Pro Asp Gly Pro Ala Asp Ala Glu Leu Ala Val
        195                 200                 205

Ile Asn Val Lys Arg Gly Lys Arg Tyr Arg Phe Arg Leu Val Ser Ile
    210                 215                 220

Ser Cys Asp Pro Asn Tyr Ile Phe Ser Ile Asp Asn His Ser Met Thr
225                 230                 235                 240

Val Ile Glu Val Asp Gly Val Asn Thr Gln Ser Leu Thr Val Asp Ser
                245                 250                 255

Ile Gln Ile Phe Ala Gly Gln Arg Tyr Ser Phe Val Leu His Ala Asn
            260                 265                 270

Arg Pro Glu Asn Asn Tyr Trp Ile Arg Ala Lys Pro Asn Ile Gly Thr
        275                 280                 285

Asp Thr Thr Thr Asp Ser Gly Met Asn Ser Ala Ile Leu Arg Tyr Asn
    290                 295                 300

Gly Ala Pro Val Ala Glu Pro Gln Thr Val Gln Ser Pro Ser Leu Thr
305                 310                 315                 320

Pro Leu Leu Glu Gln Asn Leu Arg Pro Leu Val Tyr Thr Pro Val Pro
                325                 330                 335

Gly Asn Pro Thr Pro Gly Gly Ala Asp Ile Val His Thr Leu Asp Leu
            340                 345                 350

Ser Phe Asp Ala Gly Arg Phe Ser Ile Asn Gly Ala Ser Phe Leu Asp
        355                 360                 365

Pro Thr Val Pro Val Leu Leu Gln Ile Leu Ser Gly Thr Gln Asn Ala
    370                 375                 380

Gln Asp Leu Leu Pro Pro Gly Ser Val Ile Pro Leu Glu Leu Gly Lys
385                 390                 395                 400

Val Val Glu Leu Val Ile Pro Ala Gly Val Val Gly Gly Pro His Pro
                405                 410                 415

Phe His Leu His Gly His Asn Phe Trp Val Val Arg Ser Ala Gly Thr
            420                 425                 430

Asp Gln Tyr Asn Phe Asn Asp Ala Ile Leu Arg Asp Val Val Ser Ile
        435                 440                 445

Gly Gly Thr Gly Asp Gln Val Thr Ile Arg Phe Val Thr Asp Asn Pro
    450                 455                 460

Gly Pro Trp Phe Leu His Cys His Ile Asp Trp His Leu Glu Ala Gly
465                 470                 475                 480

Leu Ala Ile Val Phe Ala Glu Gly Ile Glu Asn Thr Ala Ala Ser Asn
                485                 490                 495

Leu Thr Pro Gln Ala Trp Asp Glu Leu Cys Pro Lys Tyr Asn Ala Leu
```

```
                500               505               510
Ser Ala Gln Lys Lys Leu Asn Pro Ser Thr Thr
            515                 520

<210> SEQ ID NO 3
<211> LENGTH: 2374
<212> TYPE: DNA
<213> ORGANISM: Cerrena unicolor

<400> SEQUENCE: 3
atgagctcaa agctacttgc tcttattact gtcgctctcg tcttgccact aggcactgac      60
gccggcatcg gtcctgttac cgacttgcgc atcaccaacc aggatatcgc tccagatggc     120
ttcacccgac cagctgtact ggctgggggc acattccccg agcactgat taccggtcag      180 aaggtatggg agatcgattt cgttgaatag agaaatacaa ctgaaaacaa attcttatag     240
ggagacagct tccaaatcaa tgtcatcgac gagcttaccg atgccagcat gttgacccag     300
acatccattg tgagtataat atgggtccgc tcttctagct atcctttcta actcttaccc     360
tctagcattg gcacggcttc tttcagaagg gatctgcgtg ggccgatggt cctgccttcg     420
ttactcaatg tcctatcgtc accggaaatt ccttcctgta cgactttgat gtccccgacc     480
aacctggtac tttctggtac catagtcact tgtctactca atattgcgat ggtcttcggg     540
gcccgttcgt tgtatacgat ccaaaggatc ctaataaacg ttgtacgac attgacaatg      600 gtatgtgcat catcataaaa atataattca tgcagctact gaccgcgact gatgctgcca     660
gatcatacgt ttattaccct ggcagactgg taccacgttc tcgcacgaac tgttgtcgga     720
gtcgcgtaag tacagtctga cttatagtgg tcttcttact cattttgaca taggacaccc     780
gacgcaacct tgatcaacgg tttgggccgt tctccagacg ggccagcaga tgctgagttg     840
gctgtcatca acgttaaacg cggcaaacgg tatgtcattg aactcccgat ttctccattc     900
acattgaaat gactgtctgg tctagttatc gattccgtct ggtctccatc tcatgtgacc     960
ctaattacat cttttctatc gacaaccatt ctatgactgt catcgaagtc gatggtgtca    1020
acacccaatc cctgaccgtc gattctatcc aaatcttcgc aggccaacgc tactcgttcg    1080
tcgtaagtct ctttgaatgg ttggtgcttt ttctgtccat tctctaaccc gtttatacag    1140
ctccatgcca accgtcctga aaacaactat tggatcaggg ccaaacctaa tatcggtacg    1200
gatactacca cagacaacgg catgaactct gccattctgc gatacaacgg cgcacctgtt    1260
gcggaaccgc aaactgttca atctcccagt ctcacccctt tgctcgaaca gaaccttcgc    1320
cctctcgtgt acactcctgt ggtatgtttc aaagcgttgt aatttgattg tggtcattct    1380
aacgttactg cctttgcaca gcctggaaat cctacgcctg gcggggccga tattgtccat    1440
actcttgact tgagttttgt gcggagtcaa cattcgtaaa gataagagtg tttctaattt    1500
cttcaataat aggatgctgg tcgcttcagt atcaacggtg cctcgttcct tgatcctacc    1560
gtccctgttc tcctgcaaat tctcagcggc acgcagaatg cacaagatct actccctcct    1620
ggaagtgtga ttcctctcga attaggcaag gtcgtcgaat tagtcatacc tgcaggtgtt    1680
gtcggtggac ctcatccgtt ccatctccat ggggtacgta acccgaactt ataacagtct    1740
tggacttacc cgctgacaag tgtatagcat aacttctggg tcgtgcgaag tgccggaacc    1800
gaccagtaca acttaacga tgccattctc cgagacgtcg tcagtatagg aggaaccgag     1860
gatcaagtca ccattcgatt cgtggtatat acttcattct tgtggatgta tgtgctctag    1920
gatactaact ggcttgcgcg tatagaccga taaccccgga ccgtggttcc tccattgcca    1980
tatcgactgg cacttggaag cgggtctcgc tatcgtattt gcagagggaa ttgaaaatac    2040
```

-continued

```
tgctgcgtct aatccaaccc cccgtatgcg gtttcccaca cattctgaat ctaagcagct    2100
tactaatata catttgcaga ggcttgggat gagctttgcc cgaagtataa cgcgctcaac    2160
gcacaaaaga aggttgcatc taagaaaggc actgccatct aatccttgta acaaacaagg    2220
agggtctctt gtactttat tgggatttat tcttggggt ttattgttca acttgattct      2280
actatgtttg gaagtagcga ttacgaaagg ggcttgcgca tttatatacc atctttcttg    2340
gcaccacctg cagctcaatc cttcaaccac ctaa                                2374
```

<210> SEQ ID NO 4
<211> LENGTH: 523
<212> TYPE: PRT
<213> ORGANISM: Cerrena unicolor

<400> SEQUENCE: 4

```
Met Ser Ser Lys Leu Leu Ala Leu Ile Thr Val Ala Leu Val Leu Pro
1               5                   10                  15

Leu Gly Thr Asp Ala Gly Ile Gly Pro Val Thr Asp Leu Arg Ile Thr
            20                  25                  30

Asn Gln Asp Ile Ala Pro Asp Gly Phe Thr Arg Pro Ala Val Leu Ala
        35                  40                  45

Gly Gly Thr Phe Pro Gly Ala Leu Ile Thr Gly Gln Lys Gly Asp Ser
    50                  55                  60

Phe Gln Ile Asn Val Ile Asp Glu Leu Thr Asp Ala Ser Met Leu Thr
65                  70                  75                  80

Gln Thr Ser Ile His Trp His Gly Phe Phe Gln Lys Gly Ser Ala Trp
                85                  90                  95

Ala Asp Gly Pro Ala Phe Val Thr Gln Cys Pro Ile Val Thr Gly Asn
            100                 105                 110

Ser Phe Leu Tyr Asp Phe Asp Val Pro Asp Gln Pro Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Lys Asp Pro Asn Lys Arg Leu Tyr Asp Ile
145                 150                 155                 160

Asp Asn Asp His Thr Val Ile Thr Leu Ala Asp Trp Tyr His Val Leu
                165                 170                 175

Ala Arg Thr Val Val Gly Val Ala Thr Pro Asp Ala Thr Leu Ile Asn
            180                 185                 190

Gly Leu Gly Arg Ser Pro Asp Gly Pro Ala Asp Ala Glu Leu Ala Val
        195                 200                 205

Ile Asn Val Lys Arg Gly Lys Arg Tyr Arg Phe Arg Leu Val Ser Ile
    210                 215                 220

Ser Cys Asp Pro Asn Tyr Ile Phe Ser Ile Asp Asn His Ser Met Thr
225                 230                 235                 240

Val Ile Glu Val Asp Gly Val Asn Thr Gln Ser Leu Thr Val Asp Ser
                245                 250                 255

Ile Gln Ile Phe Ala Gly Gln Arg Tyr Ser Phe Val Leu His Ala Asn
            260                 265                 270

Arg Pro Glu Asn Asn Tyr Trp Ile Arg Ala Lys Pro Asn Ile Gly Thr
        275                 280                 285

Asp Thr Thr Thr Asp Asn Gly Met Asn Ser Ala Ile Leu Arg Tyr Asn
    290                 295                 300

Gly Ala Pro Val Ala Glu Pro Gln Thr Val Gln Ser Pro Ser Leu Thr
305                 310                 315                 320
```

Pro Leu Leu Glu Gln Asn Leu Arg Pro Leu Val Tyr Thr Pro Val Pro
            325                 330                 335

Gly Asn Pro Thr Pro Gly Gly Ala Asp Ile Val His Thr Leu Asp Leu
            340                 345                 350

Ser Phe Asp Ala Gly Arg Phe Ser Ile Asn Gly Ala Ser Phe Leu Asp
            355                 360                 365

Pro Thr Val Pro Val Leu Leu Gln Ile Leu Ser Gly Thr Gln Asn Ala
    370                 375                 380

Gln Asp Leu Leu Pro Pro Gly Ser Val Ile Pro Leu Glu Leu Gly Lys
385                 390                 395                 400

Val Val Glu Leu Val Ile Pro Ala Gly Val Val Gly Gly Pro His Pro
                405                 410                 415

Phe His Leu His Gly His Asn Phe Trp Val Val Arg Ser Ala Gly Thr
            420                 425                 430

Asp Gln Tyr Asn Phe Asn Asp Ala Ile Leu Arg Asp Val Val Ser Ile
            435                 440                 445

Gly Gly Thr Glu Asp Gln Val Thr Ile Arg Phe Val Thr Asp Asn Pro
    450                 455                 460

Gly Pro Trp Phe Leu His Cys His Ile Asp Trp His Leu Glu Ala Gly
465                 470                 475                 480

Leu Ala Ile Val Phe Ala Glu Gly Ile Glu Asn Thr Ala Ala Ser Asn
                485                 490                 495

Pro Thr Pro Gln Ala Trp Asp Glu Leu Cys Pro Lys Tyr Asn Ala Leu
            500                 505                 510

Asn Ala Gln Lys Lys Leu Asn Pro Ser Thr Thr
            515                 520

<210> SEQ ID NO 5
<211> LENGTH: 2173
<212> TYPE: DNA
<213> ORGANISM: Cerrena unicolor

<400> SEQUENCE: 5
atgtctcttc ttcgtagctt gacctccctc atcgtactag tcattggtgc atttgctgca      60
atcggtccag tcactgacct acatatagtg aaccagaatc tcgacccaga tggtttcaac     120
cgccccactg tactcgcagg tggtactttc cccggtcctc tgattcgtgg taacaaggta     180
cgcttcataa ccgccctccg tagacgtagg cttcggctga catgaccatc atctgtaggg     240
agataacttt aaaattaatg tgattgacga cttgacagag cacagtatgc tcaaggctac     300
gtccatcgta agtccctgat aacgtttcca cctggtcata tcgctcaacg tctcgaagca     360
ctggcatggg ttcttccaga agggaaccaa ctgggccgat ggccccgcct tgtcacccca     420
atgtcctatc acatcaggaa acgccttcct gtatgatttc aacgttccgg accaagctgg     480
tactttctgg taccacagcc atctctctac acagtattgt gacggtcttc gtggtgcctt     540
tgtcgtctat gatcctaatg atcccaacaa gcaactctat gatgttgata acggcaagtt     600
ccttgcatat ttcatttcta tcatatcctc acctgtattg cacagaaagc accgtgatt      660
accttggctg attggtatca tgcccttgct cagactgtca ctggtgtcgc gtgagtgaca     720
aatggccctc aattgttcac atattttcct gattatcata tgatagagta tctgatgcaa     780
cgttgatcaa cggattggga cgttcggcca ccggccccgc aaatgcccct ctggcggtca     840
tcagtgtcga gcggaataag aggtcagttc ataattatg attatttccc gcgttacttc      900
ctaacaatta ttttttgtatc cctccacaga tatcgtttcc gattggtttc tatttcttgc     960

```
gaccctaact ttattttctc aattgaccac cacccaatga ccgtaattga gatggacggt    1020
gttaataccc aatctatgac cgtagattcg atccaaatat tcgcaggtca acgatattca    1080
tttgtcgtag gttattataa actgcccacc gatcatctct cacgtaactg ttatagatgc    1140
aagccaacca accagttgga aattattgga tccgcgctaa acctaatgtt gggaacacaa    1200
ctttccttgg aggcctgaac tccgctatat tacgatatgt gggagcccct gaccaagaac    1260
cgaccactga ccaaacaccc aactctacac cgctcgttga ggcgaaccta cgaccgctcg    1320
tctatactcc tgtggtatgt tgttctcgtt acatatacca aacctaatat gaagactgaa    1380
cggatctact agccgggaca gccattccct ggcggtgctg atatcgtcaa gaacttagct    1440
ttgggtttcg tacgtgtatt tcacttccct tttggcagta actgaggtgg aatgtatata    1500
gaatgccggg cgtttcacaa tcaatggagc gtccctcaca cctcctacag tccctgtact    1560
actccagatc ctcagtggta ctcacaatgc acaggatctt ctcccagcag gaagcgtgat    1620
cgaacttgaa cagaataaag ttgtcgaaat cgttttgccc gctgcgggcg ccgttggcgg    1680
tcctcatcct tttcacttac atggtgtaag tatcagacgt cctcatgccc atattgctcc    1740
gaaccttaca cacctgattt cagcacaatt tctgggtggt tcgtagcgcc ggtcaaacca    1800
catacaattt caatgatgct cctatccgtg atgttgtcag tattggcggt gcaaacgatc    1860
aagtcacgat ccgatttgtg gtatgtatct cgtgccttgc attcattcca cgagtaatga    1920
tccttacact tcgggttctc agaccgataa ccctggccca tggttccttc actgtcacat    1980
tgactggcat ttggaggctg ggttcgctgt agtctttgcg gagggaatca atggtactgc    2040
agctgctaat ccagtcccag gtaagactct cgctgctttg cgtaatatct atgaatttaa    2100
atcatatcaa tttgcagcgg cttggaatca attgtgccca ttgtatgatg ccttgagccc    2160
aggtgataca tga                                                       2173

<210> SEQ ID NO 6
<211> LENGTH: 515
<212> TYPE: PRT
<213> ORGANISM: Cerrena unicolor

<400> SEQUENCE: 6

Met Ser Leu Leu Arg Ser Leu Thr Ser Leu Ile Val Leu Val Ile Gly
1               5                   10                  15

Ala Phe Ala Ala Ile Gly Pro Val Thr Asp Leu His Ile Val Asn Gln
            20                  25                  30

Asn Leu Asp Pro Asp Gly Phe Asn Arg Pro Thr Val Leu Ala Gly Gly
        35                  40                  45

Thr Phe Pro Gly Pro Leu Ile Arg Gly Asn Lys Gly Asp Asn Phe Lys
    50                  55                  60

Ile Asn Val Ile Asp Asp Leu Thr Glu His Ser Met Leu Lys Ala Thr
65                  70                  75                  80

Ser Ile His Trp His Gly Phe Phe Gln Lys Gly Thr Asn Trp Ala Asp
                85                  90                  95

Gly Pro Ala Phe Val Thr Gln Cys Pro Ile Thr Ser Gly Asn Ala Phe
            100                 105                 110

Leu Tyr Asp Phe Asn Val Pro Asp Gln Ala Gly Thr Phe Trp Tyr His
        115                 120                 125

Ser His Leu Ser Thr Gln Tyr Cys Asp Gly Leu Arg Gly Ala Phe Val
    130                 135                 140

Val Tyr Asp Pro Asn Asp Pro Asn Lys Gln Leu Tyr Asp Val Asp Asn
145                 150                 155                 160
```

Gly Asn Thr Val Ile Thr Leu Ala Asp Trp Tyr His Ala Leu Ala Gln
            165                 170                 175

Thr Val Thr Gly Val Ala Val Ser Asp Ala Thr Leu Ile Asn Gly Leu
            180                 185                 190

Gly Arg Ser Ala Thr Gly Pro Ala Asn Ala Pro Leu Ala Val Ile Ser
            195                 200                 205

Val Glu Arg Asn Lys Arg Tyr Arg Phe Arg Leu Val Ser Ile Ser Cys
210                 215                 220

Asp Pro Asn Phe Ile Phe Ser Ile Asp His His Pro Met Thr Val Ile
225                 230                 235                 240

Glu Met Asp Gly Val Asn Thr Gln Ser Met Thr Val Asp Ser Ile Gln
            245                 250                 255

Ile Phe Ala Gly Gln Arg Tyr Ser Phe Val Met Gln Ala Asn Gln Pro
            260                 265                 270

Val Gly Asn Tyr Trp Ile Arg Ala Lys Pro Asn Val Gly Asn Thr Thr
            275                 280                 285

Phe Leu Gly Gly Leu Asn Ser Ala Ile Leu Arg Tyr Val Gly Ala Pro
            290                 295                 300

Asp Gln Glu Pro Thr Thr Asp Gln Thr Pro Asn Ser Thr Pro Leu Val
305                 310                 315                 320

Glu Ala Asn Leu Arg Pro Leu Val Tyr Thr Pro Val Pro Gly Gln Pro
            325                 330                 335

Phe Pro Gly Gly Ala Asp Ile Val Lys Asn Leu Ala Leu Gly Phe Asn
            340                 345                 350

Ala Gly Arg Phe Thr Ile Asn Gly Ala Ser Leu Thr Pro Pro Thr Val
            355                 360                 365

Pro Val Leu Leu Gln Ile Leu Ser Gly Thr His Asn Ala Gln Asp Leu
370                 375                 380

Leu Pro Ala Gly Ser Val Ile Glu Leu Glu Gln Asn Lys Val Val Glu
385                 390                 395                 400

Ile Val Leu Pro Ala Ala Gly Ala Val Gly Gly Pro His Pro Phe His
            405                 410                 415

Leu His Gly His Asn Phe Trp Val Val Arg Ser Ala Gly Gln Thr Thr
            420                 425                 430

Tyr Asn Phe Asn Asp Ala Pro Ile Arg Asp Val Val Ser Ile Gly Gly
            435                 440                 445

Ala Asn Asp Gln Val Thr Ile Arg Phe Val Thr Asp Asn Pro Gly Pro
450                 455                 460

Trp Phe Leu His Cys His Ile Asp Trp His Leu Glu Ala Gly Phe Ala
465                 470                 475                 480

Val Val Phe Ala Glu Gly Ile Asn Gly Thr Ala Ala Asn Pro Val
            485                 490                 495

Pro Ala Ala Trp Asn Gln Leu Cys Pro Leu Tyr Asp Ala Leu Ser Pro
            500                 505                 510

Gly Asp Thr
        515

<210> SEQ ID NO 7
<211> LENGTH: 2663
<212> TYPE: DNA
<213> ORGANISM: Cerrena unicolor

<400> SEQUENCE: 7
caccgcgatg tctcttcttc gtagcttgac ctccctcatc gtactagcca ctggtgcatt    60
tgctgcaatc ggtccagtca ccgacctaca tatagtgaac cagaatctcg ccccagatgg   120

```
tttaaaccgc cccactgtac tcgcaggtgg tactttcccc ggtcctctga ttcgtggtaa    180
caaggtacgc ttcataaccg ccctccgtag acgtaggctt cggctgacat gaccatcatc    240
tgtagggaga taactttaaa attaatgtga ttgacgactt gacagaacac agtatgctca    300
aggctacgtc cattgtaagt ccctgattaa cgtttcacct ggtcatatcg ctcaacgtct    360
cgaagcactg gcatgggttc ttccagaagg gaaccaactg ggccgatggc cccgcctttg    420
tcacccaatg tcctatcaca tcaggaaacg ccttcttgta tgatttcaac gttccggacc    480
aagctggtac tttctggtac cacagccatc tctcyacaca gtattgtgac ggtcttcgtg    540
gtgcctttgt cgtctatgat cctaatgatc ccaacaagca actctatgat gttgataacg    600
gcaagtccct tgcatatttc agttctatca tatcctcacc tgtattggca cagaaagcac    660
cgtgattacc ttggctgatt ggtatcatgc ccttgctcag actgtcactg gtgtcgcgtg    720
agtgacaaat ggcccttaat tgttcacata ttttcctgat tatcatatga tagagtatct    780
gatgcaacgt tgatcaacgg attgggacgt tcggccaccg gccccgcaaa tgcccctctg    840
gcggtcatca gtgtcgagcg gaataagagg tcagttccat aattatgatt atttcccgcg    900
ttacttccta acgattattt ttgtatccct ccacagatat cgtttccgat tggtttctat    960
ttcttgcgac cctaaccttta ttttctcaat tgaccaccac ccaatgaccg taattgagat   1020
ggacggtgtt aatacccaat ctatgaccgt agattcgatc caaatattcg caggtcaacg   1080
atattcattt gtcgtaggtt attataaact gcccaccgat catctctcac gtaactgtta   1140
tagatgcaag ccaaccaacc agttggaaat tattggatcc gygctaaacc taatgttggg   1200
aacacaactt tccttggagg cctgaactcc gctatattac gatatgtggg agcccctgac   1260
caagaaccga ccactgacca aacacccaac tctacaccgc tcgtcgaggc gaacctacgt   1320
cccctcgtct atactcctgt ggtatgttgt tctcgttaca tataccaaac ctaatatgag   1380
gactgaacgg atctactagc cgggacagcc attccctggc ggtgctgata tcgtcaagaa   1440
cttagctttg ggtttcgtac gtgtatttca cttcccttttt ggcagtaact gaggtggaat   1500
gtatatagaa tgccgggcgt ttcacaatca atggaacatc cttcacacct cctacagtcc   1560
ctgtactact ccagatcctc agtggtactc acaatgcaca ggatcttctt ccagcaggaa   1620
gcgtgatcga acttgaacag aataaagttg tcgaaatcgt tctgcccgct gcgggcgccg   1680
ttggcggtcc tcatcctttc cacttacatg gtgtaagtat cagacgtcct catgcctata   1740
ttgctccgaa ccttacacac ctgatttcag cacaatttct gggtggttcg tagcgccggt   1800
caaaccacat acaatttcaa tgatgctcct atccgtgatg ttgtcagtat ggcggtgca   1860 aacgatcaag tcacgatccg atttgtggta tgtatctcgt gccttgcatt cattccacga   1920
gtaatgatcc ttacacttcg ggttctcaga ccgataaccc tggcccatgg ttccttcact   1980
gtcacattga ctggcatttg gaggctgggt tcgctgtagt ctttgcggag ggaatcaatg   2040
gcactgcagc tgctaatcca gtcccaggta agactctcgc tgctttgcgt aatatctatg   2100
aatttaaagc atatcaattt gcagcggctt ggaatcaatt gtgcccgttg tatgatgcct   2160
tgagcccagg tgatacatga ttactcgtag ctgtgctttc ttatacatat tctatgggta   2220
tatcggagta gctgtactat agtatgtact atactaggtg ggatatgytg atgttgattt   2280
atataatttt gtttgaagag tgactttatc gacttgggat ttagccgagt acatactgat   2340
ctctcactac aggcttgttt tgtctttggg cgcttactca acagttgact gttttttgcta   2400 ttacgcattg aaccgcattc cggtcygact cgtgtcctct actgtgactt gtattggcat   2460
tctagcacat atgtctctta cctataggaa caatatgtct caacactgtt ccaaaacctg   2520
```

```
cgtaaaccaa atatcgtcca tcagatcaga tcattaacag tgccgcacta acctaataca   2580
ctggcargga ctgtggaaat ccctataaat gacctctaga ccgtgaggtc attgcaaggt   2640
cgctctcctt gtcaagatga ccc                                          2663
```

<210> SEQ ID NO 8
<211> LENGTH: 515
<212> TYPE: PRT
<213> ORGANISM: Cerrena unicolor

<400> SEQUENCE: 8

```
Met Ser Leu Leu Arg Ser Leu Thr Ser Leu Ile Val Leu Ala Thr Gly
1               5                   10                  15

Ala Phe Ala Ala Ile Gly Pro Val Thr Asp Leu His Ile Val Asn Gln
            20                  25                  30

Asn Leu Ala Pro Asp Gly Leu Asn Arg Pro Thr Val Leu Ala Gly Gly
        35                  40                  45

Thr Phe Pro Gly Pro Leu Ile Arg Gly Asn Lys Gly Asp Asn Phe Lys
    50                  55                  60

Ile Asn Val Ile Asp Asp Leu Thr Glu His Ser Met Leu Lys Ala Thr
65                  70                  75                  80

Ser Ile His Trp His Gly Phe Phe Gln Lys Gly Thr Asn Trp Ala Asp
                85                  90                  95

Gly Pro Ala Phe Val Thr Gln Cys Pro Ile Thr Ser Gly Asn Ala Phe
            100                 105                 110

Leu Tyr Asp Phe Asn Val Pro Asp Gln Ala Gly Thr Phe Trp Tyr His
        115                 120                 125

Ser His Leu Ser Thr Gln Tyr Cys Asp Gly Leu Arg Gly Ala Phe Val
    130                 135                 140

Val Tyr Asp Pro Asn Asp Pro Asn Lys Gln Leu Tyr Asp Val Asp Asn
145                 150                 155                 160

Gly Asn Thr Val Ile Thr Leu Ala Asp Trp Tyr His Ala Leu Ala Gln
                165                 170                 175

Thr Val Thr Gly Val Ala Val Ser Asp Ala Thr Leu Ile Asn Gly Leu
            180                 185                 190

Gly Arg Ser Ala Thr Gly Pro Ala Asn Ala Pro Leu Ala Val Ile Ser
        195                 200                 205

Val Glu Arg Asn Lys Arg Tyr Arg Phe Arg Leu Val Ser Ile Ser Cys
    210                 215                 220

Asp Pro Asn Phe Ile Phe Ser Ile Asp His His Pro Met Thr Val Ile
225                 230                 235                 240

Glu Met Asp Gly Val Asn Thr Gln Ser Met Thr Val Asp Ser Ile Gln
                245                 250                 255

Ile Phe Ala Gly Gln Arg Tyr Ser Phe Val Met Gln Ala Asn Gln Pro
            260                 265                 270

Val Gly Asn Tyr Trp Ile Arg Ala Lys Pro Asn Val Gly Asn Thr Thr
        275                 280                 285

Phe Leu Gly Gly Leu Asn Ser Ala Ile Leu Arg Tyr Val Gly Ala Pro
    290                 295                 300

Asp Gln Glu Pro Thr Thr Asp Gln Thr Pro Asn Ser Thr Pro Leu Val
305                 310                 315                 320

Glu Ala Asn Leu Arg Pro Leu Val Tyr Thr Pro Val Pro Gly Gln Pro
                325                 330                 335

Phe Pro Gly Gly Ala Asp Ile Val Lys Asn Leu Ala Leu Gly Phe Asn
            340                 345                 350
```

```
Ala Gly Arg Phe Thr Ile Asn Gly Thr Ser Phe Thr Pro Pro Thr Val
        355                 360                 365

Pro Val Leu Leu Gln Ile Leu Ser Gly Thr His Asn Ala Gln Asp Leu
    370                 375                 380

Leu Pro Ala Gly Ser Val Ile Glu Leu Glu Gln Asn Lys Val Val Glu
385                 390                 395                 400

Ile Val Leu Pro Ala Ala Gly Ala Val Gly Gly Pro His Pro Phe His
                405                 410                 415

Leu His Gly His Asn Phe Trp Val Val Arg Ser Ala Gly Gln Thr Thr
            420                 425                 430

Tyr Asn Phe Asn Asp Ala Pro Ile Arg Asp Val Val Ser Ile Gly Gly
        435                 440                 445

Ala Asn Asp Gln Val Thr Ile Arg Phe Val Thr Asp Asn Pro Gly Pro
    450                 455                 460

Trp Phe Leu His Cys His Ile Asp Trp His Leu Glu Ala Gly Phe Ala
465                 470                 475                 480

Val Val Phe Ala Glu Gly Ile Asn Gly Thr Ala Ala Ala Asn Pro Val
                485                 490                 495

Pro Ala Ala Trp Asn Gln Leu Cys Pro Leu Tyr Asp Ala Leu Ser Pro
            500                 505                 510

Gly Asp Thr
        515

<210> SEQ ID NO 9
<211> LENGTH: 1337
<212> TYPE: DNA
<213> ORGANISM: Cerrena unicolor

<400> SEQUENCE: 9 gtggggcgg atccctaact gtttcgaatc ggcaccgaag tatgcaggtg tgacggagat      60
gaggcgtttt ttcatcttcc actgcagtat aaaatgtctc aggtaacgtc cagcttttg    120 taccagagct acctccaaat acctttactc gcaaaggttt cgcgatgtct cttcttcgta   180
gcttgacctc cctcatcgta ctagccactg gtgcatttgc tgcaatcggt ccagtcactg   240
acctacatat agtgaaccag aatctcgccc cagatggttt caaccgcccc actgtactcg   300
caggtggtac tttccccggt cctctgattc gtggtaacaa ggtacgcttc ataaccgccc   360
tccgtagacg taggcttcgg ctgacatgac catcatctgt agggagataa ctttaaaatt   420
aatgtgattg acgacttgac agaacacagt atgctcaagg ccacgtccat gtaagtccc    480 tgattaacgt ttcacctggt catatcgctc aacgtctcga agcactggca tgggttcttc   540
cagaagggaa ccaactgggc cgatggcccc gcctttgtca cccaatgtcc atcacatca    600 ggaaactcct tcctgtatga tttcaacgtt ccggaccaag ctggtacttt ctggtaccac   660
agccatctct ctacacagta ttgtgacggt cttcgtggtg cctttgtcgt ctatgatcct   720
aatgatccca caagcaact ctatgatgtt gataacggca agtcccttgc atatttcatt    780
tctatcatat cctcacctgt attggcacag aaagcaccgt gattaccttg gctgattggt   840
atcatgccct tgctcagact gtcactggtg tcgcgtgagt gacaaatggc cctcaattgt   900
tcacatattt tcctgattat catatgatag agtatctgat gcaacgttga tcaacggatt   960
gggacgttcg gccaccggcc ccgcaaatgc ccctctggcg gtcatcagtg tcgagcggaa  1020
taagaggtca gttccataat tatgattatt cccgcgttaa cttcctaaca attattcttg  1080
tatccctcca cagatatcgc ttccgattgg tgtctatttc ttgcgaccct aactttattt  1140
```

```
tctcaattga tcaccaccca atgaccgtaa ttgagatgga cggtgttaat acccaatcta    1200
tgaccgtaga ttcgatccaa atattcgcag gtcaacgata ttcatttgtc gtaggttatt    1260
ataaactgcc caccgatcat ctctcacgta actgttatag atgcaagcca accaaccrgt    1320
tggaaattat tggatcc                                                  1337
```

<210> SEQ ID NO 10
<211> LENGTH: 278
<212> TYPE: PRT
<213> ORGANISM: Cerrena unicolor

<400> SEQUENCE: 10

```
Met Ser Leu Leu Arg Ser Leu Thr Ser Leu Ile Val Leu Ala Thr Gly
1               5                   10                  15

Ala Phe Ala Ala Ile Gly Pro Val Thr Asp Leu His Ile Val Asn Gln
            20                  25                  30

Asn Leu Ala Pro Asp Gly Phe Asn Arg Pro Thr Val Leu Ala Gly Gly
        35                  40                  45

Thr Phe Pro Gly Pro Leu Ile Arg Gly Asn Lys Gly Asp Asn Phe Lys
    50                  55                  60

Ile Asn Val Ile Asp Asp Leu Thr Glu His Ser Met Leu Lys Ala Thr
65                  70                  75                  80

Ser Ile His Trp His Gly Phe Phe Gln Lys Gly Thr Asn Trp Ala Asp
                85                  90                  95

Gly Pro Ala Phe Val Thr Gln Cys Pro Ile Thr Ser Gly Asn Ser Phe
            100                 105                 110

Leu Tyr Asp Phe Asn Val Pro Asp Gln Ala Gly Thr Phe Trp Tyr His
        115                 120                 125

Ser His Leu Ser Thr Gln Tyr Cys Asp Gly Leu Arg Gly Ala Phe Val
    130                 135                 140

Val Tyr Asp Pro Asn Asp Pro Asn Lys Gln Leu Tyr Asp Val Asp Asn
145                 150                 155                 160

Gly Lys Thr Val Ile Thr Leu Ala Asp Trp Tyr His Ala Leu Ala Gln
                165                 170                 175

Thr Val Thr Gly Val Ala Val Ser Asp Ala Thr Leu Ile Asn Gly Leu
            180                 185                 190

Gly Arg Ser Ala Thr Gly Pro Ala Asn Ala Pro Leu Ala Val Ile Ser
        195                 200                 205

Val Glu Arg Asn Lys Arg Tyr Arg Phe Arg Leu Val Ser Ile Ser Cys
    210                 215                 220

Asp Pro Asn Phe Ile Phe Ser Ile Asp His His Pro Met Thr Val Ile
225                 230                 235                 240

Glu Met Asp Gly Val Asn Thr Gln Ser Met Thr Val Asp Ser Ile Gln
                245                 250                 255

Ile Phe Ala Gly Gln Arg Tyr Ser Phe Val Met Gln Ala Asn Gln Pro
            260                 265                 270

Val Gly Asn Tyr Trp Ile
        275
```

<210> SEQ ID NO 11
<211> LENGTH: 1080
<212> TYPE: DNA
<213> ORGANISM: Cerrena unicolor

<400> SEQUENCE: 11

```
tgcaatcgga ccggtbgctg accttcacat tacggacgat accattgccc ccgatggttt    60
```

-continued

```
ctctcgtcct gctgttctcg ctggcggggg tttccctggc cctctcatca ccggaaacaa    120
ggtaatgcct aatggttgcg tctttgttgg tgctctcatt catccacgac attttgtacc    180
agggcgacgc ctttaaactc aatgtcatcg atgaactaac ggacgcatcc atgctgaagy    240
cgacttccat cgtaagtctc gctgtattgc tccttgagcc atttcattga ctataactac    300
aaccagcact ggcatggatt cttccaaaag ggtactaatt gggcagatgg tcccgctttt    360
gtgaaccaat gccccatcac cacgggaaac tccttcttgt acgacttcca ggttcctgat    420
caagctggta agcatgagat tacactagga aagtttaatt taataactat tcaatcagga    480
acctactggt atcatagtca tttgtctacg caatactgtg atggtctcag aggtgcattc    540
gttgtctacg acccttcaga tcctcacaag gatctctacg acgtcgacga cggtgagctt    600
tgcttttttc attggtatcc attatcgctc acgtgtcatt actgcgccac agaaagtacc    660
gtcatcactt ggctgattg gtatcatact ttggctcgtc agattgttgg cgttgcgtga    720
gtagtcttgt accgactgaa acatattcca gttgctgact cccacagc atttctgata    780 ctaccttgat aaacggtttg ggccgcaata ccaatggtcc ggctgatgct gctcttgctg    840
tgatcaatgt tgacgctggc aaacggtgtg tccagattac tatactcccc atgacgtctc    900
aatgctgatg tgtactactt ccaggtaccg tttccgtctt gtttccatat cctgtgaccc    960
caattgggta ttctcgattg acaaccatga ctttacggtc attgaagtcg atggtgttaa   1020
cagtcaacct ctcaacgtcg attctgttca gatcttcgcc ggacaacgtt actcgttcgt   1080
```

<210> SEQ ID NO 12
<211> LENGTH: 246
<212> TYPE: PRT
<213> ORGANISM: Cerrena unicolor
<220> FEATURE:
<221> NAME/KEY: misc_feature
<222> LOCATION: (60)..(60)
<223> OTHER INFORMATION: Xaa can be any naturally occurring amino acid

<400> SEQUENCE: 12

```
Ala Ile Gly Pro Val Ala Asp Leu His Ile Thr Asp Asp Thr Ile Ala
1               5                   10                  15

Pro Asp Gly Phe Ser Arg Pro Ala Val Leu Ala Gly Gly Phe Pro
            20                  25                  30

Gly Pro Leu Ile Thr Gly Asn Lys Gly Asp Ala Phe Lys Leu Asn Val
        35                  40                  45

Ile Asp Glu Leu Thr Asp Ala Ser Met Leu Lys Xaa Thr Ser Ile His
    50                  55                  60

Trp His Gly Phe Phe Gln Lys Gly Thr Asn Trp Ala Asp Gly Pro Ala
65                  70                  75                  80

Phe Val Asn Gln Cys Pro Ile Thr Thr Gly Asn Ser Phe Leu Tyr Asp
                85                  90                  95

Phe Gln Val Pro Asp Gln Ala Gly Thr Tyr Trp Tyr His Ser His Leu
            100                 105                 110

Ser Thr Gln Tyr Cys Asp Gly Leu Arg Gly Ala Phe Val Val Tyr Asp
        115                 120                 125

Pro Ser Asp Pro His Lys Asp Leu Tyr Asp Val Asp Asp Glu Ser Thr
    130                 135                 140

Val Ile Thr Leu Ala Asp Trp Tyr His Thr Leu Ala Arg Gln Ile Val
145                 150                 155                 160

Gly Val Ala Ile Ser Asp Thr Thr Leu Ile Asn Gly Leu Gly Arg Asn
                165                 170                 175

Thr Asn Gly Pro Ala Asp Ala Ala Leu Ala Val Ile Asn Val Asp Ala
```

```
              180                 185                 190
Gly Lys Arg Tyr Arg Phe Arg Leu Val Ser Ile Ser Cys Asp Pro Asn
        195                 200                 205

Trp Val Phe Ser Ile Asp Asn His Asp Phe Thr Val Ile Glu Val Asp
        210                 215                 220

Gly Val Asn Ser Gln Pro Leu Asn Val Asp Ser Val Gln Ile Phe Ala
225                 230                 235                 240

Gly Gln Arg Tyr Ser Phe
                245

<210> SEQ ID NO 13
<211> LENGTH: 2809
<212> TYPE: DNA
<213> ORGANISM: Cerrena unicolor

<400> SEQUENCE: 13
gattctaata gaccaggcat accaagagat ctacaggttg acagaccatt cttctaggcg      60
gcatttatgc tgtagcgtca gaaattatct ctccatttgt atcccacagg tcctgtaata     120
acacggagac agtccaaact gggatgcctt ttttctcaac tatgggcgca catagtctgg     180
acgatggtat ataagacgat ggtatgagac ccatgaagtc agaacacttt tgctctctga     240
catttcatgg ttcacactct cgagatggga ttgaactcgg ctattacatc gcttgctatc     300
ttagctctgt cagtcggaag ctatgctgca attgggcccg tggccgacat acacattgtc     360
aacaaagacc ttgctccaga tggcgtacaa cgtccaaccg tgcttgccgg aggcactttt     420
cctgggacgt tgatcaccgg tcagaaagta agggatatta gtttgcgtca aagagccaac     480
caaaactaac cgtcccgtac tatagggtga caacttccag ctcaatgtca tcgatgatct     540
taccgacgat cggatgttga cgccaacttc cattgtgagc ctattattgt atgatttatc     600
cgaatagttt cgcagtctga tcattggatc tctatcgcta gcattggcac ggtttcttcc     660
agaagggaac cgcttgggcc gacggtcccg ccttcgtaac tcagtgccct ataatagcag     720
ataactcttt tctgtatgac ttcgacgtcc cagaccaagc tggtactttc tggtatcata     780
gtcatctatc cactcagtac tgtgacggtt acgtggtgc cttcgttgtg tacgatccta     840
acgatcctca caaagaccta tacgatgttg atgacggtgg gttccaaata tttgttctgc     900
agacattgta ttgacggtgt tcattataat ttcagagagc accgtgatta cccttgcgga     960
ttggtaccat gttctcgccc agaccgttgt cggcgctgcg tgagtaacac atacacgcgc    1020
tccggcacac tgatactaat tttttttat tgtagcactc ctgattctac cttgatcaac    1080
gggttaggcc gttcacagac cggacccgct gatgctgagc tggctgttat cagcgttgaa    1140
cataacaaac ggtatgtcat ctctacccag tatcttctct cctgctctaa ttcgctgttt    1200
caccatagat accgtttccg tttggtttcg atttcgtgcg accccaactt taccttctcc    1260
gttgatggtc ataatatgac tgtcatcgaa gtcgatggtg tcaacacacg acccctgacc    1320
gttgactcta ttcaaatctt cgccggacag aggtattcct ttgtcgtaag ttaatcgata    1380
tattctcctt attaccctg tgtaattgat gtcaatagct caatgctaac caacccgaag    1440
acaattactg gatccgtgct atgccaaaca tcggtagaaa tacaacaaca ctggacggaa    1500
agaatgccgc tatccttcga tacaagaatg cttctgtaga agagcccaag accgttgggg    1560
gccccgctca atcccgttg aatgaagcgg acctgcgtcc actcgtacct gctcctgtgg    1620
tatgtcttgt cgcgctgttc catcgctatt tcatattaac gttttgtttt tgtcaagcct    1680
ggaaacgctg ttccaggtgg cgcagacatc aatcacaggc ttaacttaac tttcgtacgt    1740
```

```
acacctggtt gaaacattat atttccagtc taacctctct tgtagagtaa cggcctcttc   1800
agcatcaaca acgcctcctt cactaatcct tcggtccccg ccttattaca aattctgagc   1860
ggtgctcaga acgctcaaga tttacttcca acgggtagtt acattggcct tgaactaggc   1920
aaggttgtgg agctcgttat acctcctctg gcagttggag gaccgcaccc tttccatctt   1980
catggcgtaa gcataccaca ctcccgcagc cagaatgacg caaactaatc atgatatgca   2040
gcacaatttc tgggtcgtcc gtagtgcagg tagcgatgag tataactttg acgatgctat   2100
cctcagggac gtcgtragca ttggagcggg gactgatgaa gtcacaatcc gtttcgtggt   2160
atgtctcacc cctcgcattt tgagacgcaa gagctgatat attttaacat agaccgacaa   2220
tccgggcccg tggttcctcc attgccatat tgattggcat ttggaggcag gccttgccat   2280
cgtcttcgct gagggcatca atcagaccgc tgcagccaac ccaacacccc gtacgtgaca   2340
ctgagggttt ctttatagtg ctggattact gaatcgagat ttctccacag aagcatggga   2400
tgagctttgc cccaaatata acgggttgag tgcgagccag aaggtcaagc taagaaagg    2460
aactgctatt taaacgtggt cctagactac gggcatataa gtattcgggt agcgcgtgtg   2520
agcaatgttc cgatacacgt agattcatca ccggacacgc tgggacaatt tgtgtataat   2580
ggctagtaac gtatctgagt tctggtgtgt agttcaaaga gacagccctt cctgagacag   2640
cccttcctga cagcccctt cctgagacgt gacctccgta gtctgcacac gatactycta    2700
aatacgtatg gcaagatgac aaagaggagg atgtgagtta ctacgaacag aaatagtgcc   2760
cggcctcgga gagatgttct tgaatatggg actgggacca acatccgga               2809
```

<210> SEQ ID NO 14
<211> LENGTH: 526
<212> TYPE: PRT
<213> ORGANISM: Cerrena unicolor

<400> SEQUENCE: 14

```
Met Gly Leu Asn Ser Ala Ile Thr Ser Leu Ala Ile Leu Ala Leu Ser
1               5                   10                  15

Val Gly Ser Tyr Ala Ala Ile Gly Pro Val Ala Asp Ile His Ile Val
            20                  25                  30

Asn Lys Asp Leu Ala Pro Asp Gly Val Gln Arg Pro Thr Val Leu Ala
        35                  40                  45

Gly Gly Thr Phe Pro Gly Thr Leu Ile Thr Gly Gln Lys Gly Asp Asn
    50                  55                  60

Phe Gln Leu Asn Val Ile Asp Asp Leu Thr Asp Asp Arg Met Leu Thr
65                  70                  75                  80

Pro Thr Ser Ile His Trp His Gly Phe Phe Gln Lys Gly Thr Ala Trp
                85                  90                  95

Ala Asp Gly Pro Ala Phe Val Thr Gln Cys Pro Ile Ile Ala Asp Asn
            100                 105                 110

Ser Phe Leu Tyr Asp Phe Asp Val Pro Asp Gln Ala Gly Thr Phe Trp
        115                 120                 125

Tyr His Ser His Leu Ser Thr Gln Tyr Cys Asp Gly Leu Arg Gly Ala
    130                 135                 140

Phe Val Val Tyr Asp Pro Asn Asp Pro His Lys Asp Leu Tyr Asp Val
145                 150                 155                 160

Asp Asp Gly Gly Thr Val Ile Thr Leu Ala Asp Trp Tyr His Val Leu
                165                 170                 175

Ala Gln Thr Val Val Gly Ala Ala Thr Pro Asp Ser Thr Leu Ile Asn
            180                 185                 190
```

```
Gly Leu Gly Arg Ser Gln Thr Gly Pro Ala Asp Ala Glu Leu Ala Val
        195                 200                 205

Ile Ser Val Glu His Asn Lys Arg Tyr Arg Phe Arg Leu Val Ser Ile
    210                 215                 220

Ser Cys Asp Pro Asn Phe Thr Phe Ser Val Asp Gly His Asn Met Thr
225                 230                 235                 240

Val Ile Glu Val Asp Gly Val Asn Thr Arg Pro Leu Thr Val Asp Ser
                245                 250                 255

Ile Gln Ile Phe Ala Gly Gln Arg Tyr Ser Phe Val Leu Asn Ala Asn
            260                 265                 270

Gln Pro Glu Asp Asn Tyr Trp Ile Arg Ala Met Pro Asn Ile Gly Arg
        275                 280                 285

Asn Thr Thr Thr Leu Asp Gly Lys Asn Ala Ala Ile Leu Arg Tyr Lys
    290                 295                 300

Asn Ala Ser Val Glu Glu Pro Lys Thr Val Gly Gly Pro Ala Gln Ser
305                 310                 315                 320

Pro Leu Asn Glu Ala Asp Leu Arg Pro Leu Val Pro Ala Pro Val Pro
                325                 330                 335

Gly Asn Ala Val Pro Gly Gly Ala Asp Ile Asn His Arg Leu Asn Leu
            340                 345                 350

Thr Phe Ser Asn Gly Leu Phe Ser Ile Asn Asn Ala Ser Phe Thr Asn
        355                 360                 365

Pro Ser Val Pro Ala Leu Leu Gln Ile Leu Ser Gly Ala Gln Asn Ala
    370                 375                 380

Gln Asp Leu Leu Pro Thr Gly Ser Tyr Ile Gly Leu Glu Leu Gly Lys
385                 390                 395                 400

Val Val Glu Leu Val Ile Pro Pro Leu Ala Val Gly Gly Pro His Pro
                405                 410                 415

Phe His Leu His Gly His Asn Phe Trp Val Val Arg Ser Ala Gly Ser
            420                 425                 430

Asp Glu Tyr Asn Phe Asp Asp Ala Ile Leu Arg Asp Val Val Ser Ile
        435                 440                 445

Gly Ala Gly Thr Asp Glu Val Thr Ile Arg Phe Val Thr Asp Asn Pro
    450                 455                 460

Gly Pro Trp Phe Leu His Cys His Ile Asp Trp His Leu Glu Ala Gly
465                 470                 475                 480

Leu Ala Ile Val Phe Ala Glu Gly Ile Asn Gln Thr Ala Ala Ala Asn
                485                 490                 495

Pro Thr Pro Gln Ala Trp Asp Glu Leu Cys Pro Lys Tyr Asn Gly Leu
            500                 505                 510

Ser Ala Ser Gln Lys Val Lys Pro Lys Lys Gly Thr Ala Ile
        515                 520                 525

<210> SEQ ID NO 15
<211> LENGTH: 2299
<212> TYPE: DNA
<213> ORGANISM: Cerrena unicolor

<400> SEQUENCE: 15
gatctggacg atggtatata agacgatggt atgagaccca tgaagtctga acacttttgc     60
tctctgacat ttcatggttc atactctcga gatgggattg aactcggcta ttacatcgct    120
tgctatctta gctctgtcag tcggaagcta tgctgcaatt gggcccgtgg ccgacataca    180
cattgtcaac aaagaccttg ctccagatgg tgtacaacgt ccaaccgtgc tcgccggagg    240 cactttttcct gggacgttga tcaccggtca gaaagtaagg aatattagtt tgcgtcaaag    300
```

| | | | |
|---|---|---|---|
| agccaaccaa | aattaaccgt | cccgtcccat | agggtgacaa cttccagctc aatgtcattg | 360 |
| atgatcttac | cgacgatcgg | atgttgacac | caacttccat tgtgagccta ttattgtatg | 420 |
| atttatccgt | atagtttctc | agtctgatca | ttggctctct atcgctagca ttggcacggt | 480 |
| ttcttccaga | agggaaccgc | ttgggccgac | ggtcccgcct tcgtaactca gtgccctata | 540 |
| atagcagata | actcttttct | gtatgacttc | gacgtccccg accaagctgg tactttctgg | 600 |
| tatcatagtc | atctatccac | tcagtactgt | gacggtttac gtggtgcctt cgttgtgtac | 660 |
| gatcctaacg | atcctcacaa | agacctatac | gatgttgatg acggtgggtt ccaaatactt | 720 |
| gaccaagaaa | cattatattg | atagtatcca | ctctgatttt cagagagcac cgtgattacc | 780 |
| cttgcggatt | ggtaccatgt | tctcgcccag | accgttgtcg gcgctgcgtg agtaacacat | 840 |
| acacgcgctc | cggcacactg | atactaattt | tttattgtag cactcctgat tctaccttga | 900 |
| tcaacgggtt | aggccgttca | cagaccggac | ccgctgatgc tgagctggct gttatcagcg | 960 |
| ttgaacataa | caaacggtat | gtcatctcta | cccattatct tctctcctgc tttaattcgc | 1020 |
| tgtttcacca | tagataccga | ttccgtttgg | tttcgatttc gtgcgacccc aactttacct | 1080 |
| tctccgttga | tggtcataat | atgactgtca | tcgaagtcga cggtgtcaac acacgacccc | 1140 |
| tgaccgttga | ctctattcaa | atcttcgccg | gacagaggta ttcctttgtc gtaagttaat | 1200 |
| cgatatattc | tccctattac | ccctgtgtaa | ttgatgtcaa cagctcaatg ctaaccaacc | 1260 |
| cgacgacaat | tactggatcc | gtgctatgcc | aaacatcggt agaaatacaa caacactgga | 1320 |
| cggaaagaat | gccgctatcc | ttcgatacaa | gaatgcttct gtagaagagc caagaccgt | 1380 |
| tgggggcccc | gctcaatccc | cgttgaatga | agcggacctg cgtccactcg tacctgctcc | 1440 |
| tgtggtatgt | cttgtcgtgc | tgttccatcg | ctatttcata ttaacgtttt gtttttgtca | 1500 |
| agcctggaaa | cgctgttcca | ggtggcgcag | acatcaatca caggcttaac ttaactttcg | 1560 |
| tacgtacacc | tggttgaaac | attatatttc | cagtctaacc tcttgtagag taacggcctt | 1620 |
| ttcagcatca | acaacgcctc | cttcactaat | ccttcggtcc ccgccttatt acaaattctg | 1680 |
| agcggtgctc | agaacgctca | agatttactt | ccaacgggta gttacattgg ccttgaacta | 1740 |
| ggcaaggttg | tggagctcgt | tatacctcct | ctggcagttg gaggaccgca cccttccat | 1800 |
| cttcatggcg | taagcatacc | acactcccgc | agccagaatg acgcaaacta atcatgatat | 1860 |
| gcagcacaat | ttctgggtcg | tccgtagtgc | aggtagcgat gagtataact ttgacgatgc | 1920 |
| tatcctcagg | gacgtcgtga | gcattggagc | ggggactgat gaagtcacaa tccgtttcgt | 1980 |
| ggtatgtctc | accctcgca | ttttgagacg | caagagctga tatattttaa catagaccga | 2040 |
| caatccgggc | ccgtggttcc | tccattgcca | tattgattgg catttggagg caggccttgc | 2100 |
| catcgtcttc | gctgagggca | tcaatcagac | cgctgcagcc aacccaacac cccgtacgtg | 2160 |
| acactgaggg | tttctttata | gtgctggatt | actgaatcga gatttctcca cagaagcatg | 2220 |
| ggatgagctt | tgccccaaat | ataacgggtt | gagtgcgagc cagaaggtca agcctaagaa | 2280 |
| aggaactgct | atttaaacg | | | 2299 |

<210> SEQ ID NO 16
<211> LENGTH: 526
<212> TYPE: PRT
<213> ORGANISM: Cerrena unicolor

<400> SEQUENCE: 16

Met Gly Leu Asn Ser Ala Ile Thr Ser Leu Ala Ile Leu Ala Leu Ser
1               5                   10                  15

-continued

```
Val Gly Ser Tyr Ala Ala Ile Gly Pro Val Ala Asp Ile His Ile Val
            20              25              30
Asn Lys Asp Leu Ala Pro Asp Gly Val Gln Arg Pro Thr Val Leu Ala
            35              40              45
Gly Gly Thr Phe Pro Gly Thr Leu Ile Thr Gly Gln Lys Gly Asp Asn
 50              55              60
Phe Gln Leu Asn Val Ile Asp Asp Leu Thr Asp Arg Met Leu Thr
 65              70              75              80
Pro Thr Ser Ile His Trp His Gly Phe Phe Gln Lys Gly Thr Ala Trp
                85              90              95
Ala Asp Gly Pro Ala Phe Val Thr Gln Cys Pro Ile Ile Ala Asp Asn
            100             105             110
Ser Phe Leu Tyr Asp Phe Asp Val Pro Asp Gln Ala Gly Thr Phe Trp
        115             120             125
Tyr His Ser His Leu Ser Thr Gln Tyr Cys Asp Gly Leu Arg Gly Ala
        130             135             140
Phe Val Val Tyr Asp Pro Asn Asp Pro His Lys Asp Leu Tyr Asp Val
145             150             155             160
Asp Asp Gly Gly Thr Val Ile Thr Leu Ala Asp Trp Tyr His Val Leu
                165             170             175
Ala Gln Thr Val Val Gly Ala Ala Thr Pro Asp Ser Thr Leu Ile Asn
            180             185             190
Gly Leu Gly Arg Ser Gln Thr Gly Pro Ala Asp Ala Glu Leu Ala Val
        195             200             205
Ile Ser Val Glu His Asn Lys Arg Tyr Arg Phe Arg Leu Val Ser Ile
210             215             220
Ser Cys Asp Pro Asn Phe Thr Phe Ser Val Asp Gly His Asn Met Thr
225             230             235             240
Val Ile Glu Val Asp Gly Val Asn Thr Arg Pro Leu Thr Val Asp Ser
            245             250             255
Ile Gln Ile Phe Ala Gly Gln Arg Tyr Ser Phe Val Leu Asn Ala Asn
        260             265             270
Gln Pro Asp Asp Asn Tyr Trp Ile Arg Ala Met Pro Asn Ile Gly Arg
    275             280             285
Asn Thr Thr Thr Leu Asp Gly Lys Asn Ala Ala Ile Leu Arg Tyr Lys
290             295             300
Asn Ala Ser Val Glu Glu Pro Lys Thr Val Gly Gly Pro Ala Gln Ser
305             310             315             320
Pro Leu Asn Glu Ala Asp Leu Arg Pro Leu Val Pro Ala Pro Val Pro
            325             330             335
Gly Asn Ala Val Pro Gly Gly Ala Asp Ile Asn His Arg Leu Asn Leu
        340             345             350
Thr Phe Ser Asn Gly Leu Phe Ser Ile Asn Asn Ala Ser Phe Thr Asn
        355             360             365
Pro Ser Val Pro Ala Leu Leu Gln Ile Leu Ser Gly Ala Gln Asn Ala
370             375             380
Gln Asp Leu Leu Pro Thr Gly Ser Tyr Ile Gly Leu Glu Leu Gly Lys
385             390             395             400
Val Val Glu Leu Val Ile Pro Pro Leu Ala Val Gly Gly Pro His Pro
            405             410             415
Phe His Leu His Gly His Asn Phe Trp Val Val Arg Ser Ala Gly Ser
        420             425             430
Asp Glu Tyr Asn Phe Asp Asp Ala Ile Leu Arg Asp Val Val Ser Ile
        435             440             445
```

```
Gly Ala Gly Thr Asp Glu Val Thr Ile Arg Phe Val Thr Asp Asn Pro
            450                 455                 460

Gly Pro Trp Phe Leu His Cys His Ile Asp Trp His Leu Glu Ala Gly
465                 470                 475                 480

Leu Ala Ile Val Phe Ala Glu Gly Ile Asn Gln Thr Ala Ala Ala Asn
                485                 490                 495

Pro Thr Pro Gln Ala Trp Asp Glu Leu Cys Pro Lys Tyr Asn Gly Leu
            500                 505                 510

Ser Ala Ser Gln Lys Val Lys Pro Lys Lys Gly Thr Ala Ile
            515                 520                 525

<210> SEQ ID NO 17
<211> LENGTH: 1163
<212> TYPE: DNA
<213> ORGANISM: Cerrena unicolor

<400> SEQUENCE: 17
tgcaatcgga ccggtggccg acctcaagat cgtaaaccga cattgcac ctgacggttt       60 tattcgtccc gccgttctcg ctggagggtc gttccctggt cctctcatta cagggcagaa     120
agtacgttac gctatctcgg tgctttggct taattaaact atttgactt gtgttctctt     180 aggggaacga gttcaaaatc aatgtagtca atcaactgac cgatggttct atgttaaaat    240
ccacctcaat cgtaagcaga atgagccctt tgcatctcgt tttattgtta atgcgcccac     300
tatagcattg gcatggattc ttccagaagg gaacaaactg gcagacggt cctgcgttcg     360 tgaaccaatg tccaatcgcc acgaacaatt cgttcttgta tcagtttacc tcacaggaac     420
agccaggtga gtatgagatg gagttcatcc gagcatgaac tgatttattt ggaacctagg     480
cacattttgg taccatagtc atctttccac acaatactgc gatggtttgc gagggccact     540
cgtggtgtat gacccacaag acccgcatgc tgttctctac gacgtcgacg atggttcgta     600
cttcgcatat ccacgctcgc tttcatacaa tgtaaacttt gttcctccag aaagtacaat     660
catcacgctc gcggattggt atcatacctt ggctcggcaa gtgaaaggcc cagcgtaagg     720
cactttagtg tttcctcata gtccaagaaa ttctaacacg ccttcttcat cagggttcct     780
ggtacgacct tgatcaacgg gttggggcgt cacaacaatg gtcctctaga tgctgaacta     840
gcggtgatca gtgttcaagc cggcaaacgg caagttcaat tcacactttt cactctgtac     900
cttcttcctg acattctttt cttgtagtta ccgcttccgc ctgatttcaa tttcatgcga     960
tcccaactac gtattctcca ttgatggcca tgatatgact gtcatcgaag tggatagtgt    1020
taacagtcaa cctctcaagg tagattctat ccaaatattt gcaggtcaga gatattcgtt    1080
cgtggtgagt cagatcaggg catatccttt tgtcgatacg tcattgacca tataatgcta    1140
caagctgaat gccaaccaac cag                                             1163

<210> SEQ ID NO 18
<211> LENGTH: 262
<212> TYPE: PRT
<213> ORGANISM: Cerrena unicolor

<400> SEQUENCE: 18

Ala Ile Gly Pro Val Ala Asp Leu Lys Ile Val Asn Arg Asp Ile Ala
1               5                   10                  15

Pro Asp Gly Phe Ile Arg Pro Val Leu Ala Gly Gly Ser Phe Pro
            20                  25                  30

Gly Pro Leu Ile Thr Gly Gln Lys Gly Asn Glu Phe Lys Ile Asn Val
            35                  40                  45
```

```
Val Asn Gln Leu Thr Asp Gly Ser Met Leu Lys Ser Thr Ser Ile His
        50                  55                  60

Trp His Gly Phe Phe Gln Lys Gly Thr Asn Trp Ala Asp Gly Pro Ala
65                      70                  75                  80

Phe Val Asn Gln Cys Pro Ile Ala Thr Asn Asn Ser Phe Leu Tyr Gln
                85                  90                  95

Phe Thr Ser Gln Glu Gln Pro Gly Thr Phe Trp Tyr His Ser His Leu
            100                 105                 110

Ser Thr Gln Tyr Cys Asp Gly Leu Arg Gly Pro Leu Val Val Tyr Asp
        115                 120                 125

Pro Gln Asp Pro His Ala Val Leu Tyr Asp Val Asp Asp Glu Ser Thr
    130                 135                 140

Ile Ile Thr Leu Ala Asp Trp Tyr His Thr Leu Ala Arg Gln Val Lys
145                 150                 155                 160

Gly Pro Ala Val Pro Gly Thr Thr Leu Ile Asn Gly Leu Gly Arg His
                165                 170                 175

Asn Asn Gly Pro Leu Asp Ala Glu Leu Ala Val Ile Ser Val Gln Ala
                180                 185                 190

Gly Lys Arg Gln Val Gln Phe Thr Leu Phe Thr Leu Tyr Arg Phe Arg
            195                 200                 205

Leu Ile Ser Ile Ser Cys Asp Pro Asn Tyr Val Phe Ser Ile Asp Gly
210                 215                 220

His Asp Met Thr Val Ile Glu Val Asp Ser Val Asn Ser Gln Pro Leu
225                 230                 235                 240

Lys Val Asp Ser Ile Gln Ile Phe Ala Gly Gln Arg Tyr Ser Phe Val
                245                 250                 255

Leu Asn Ala Asn Gln Pro
            260

<210> SEQ ID NO 19
<211> LENGTH: 10
<212> TYPE: PRT
<213> ORGANISM: Cerrena unicolor

<400> SEQUENCE: 19

Ala Ile Gly Pro Val Ala Asp Leu His Ile
1               5                   10

<210> SEQ ID NO 20
<211> LENGTH: 7
<212> TYPE: PRT
<213> ORGANISM: Cerrena unicolor

<400> SEQUENCE: 20

Met Leu Thr Pro Thr Ser Ile
1               5

<210> SEQ ID NO 21
<211> LENGTH: 6
<212> TYPE: PRT
<213> ORGANISM: Cerrena unicolor

<400> SEQUENCE: 21

Thr Val Gly Gly Pro Ala
1               5

<210> SEQ ID NO 22
<211> LENGTH: 10
<212> TYPE: PRT
```

<213> ORGANISM: Cerrena unicolor

<400> SEQUENCE: 22

Tyr Ser Phe Val Leu Asn Ala Asn Gln Pro
1               5                   10

<210> SEQ ID NO 23
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 23
gcaatcggac cngtngcaga                                              20

<210> SEQ ID NO 24
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 24
gcaatcggac cngtngctga                                              20

<210> SEQ ID NO 25
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 25
gcaatcggac cngtngcgga                                              20

<210> SEQ ID NO 26
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature

```
<222> LOCATION: (15)..(15)
<223> OTHER INFORMATION: n is a, c, g, or t

<400> SEQUENCE: 26
gcaatcggac cngtngccga                                              20

<210> SEQ ID NO 27
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 27
ggttgatttg cattnagnac                                              20

<210> SEQ ID NO 28
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 28
ggttgatttg cgttnagnac                                              20

<210> SEQ ID NO 29
<211> LENGTH: 20
<212> TYPE: DNA
<213> ORGANISM: Artificial
<220> FEATURE:
<223> OTHER INFORMATION: synthetic primer

<400> SEQUENCE: 29
ggacgtggcc ttgagcatac                                              20

<210> SEQ ID NO 30
<211> LENGTH: 20
<212> TYPE: DNA
<213> ORGANISM: Artificial
<220> FEATURE:
<223> OTHER INFORMATION: synthetic primer

<400> SEQUENCE: 30
tctgtcaagt cgtcaatcac                                              20

<210> SEQ ID NO 31
<211> LENGTH: 16
<212> TYPE: DNA
<213> ORGANISM: Artificial
<220> FEATURE:
<223> OTHER INFORMATION: synthetic primer
<220> FEATURE:
<221> NAME/KEY: misc_feature
```

```
<222> LOCATION: (1)..(10)
<223> OTHER INFORMATION: n is a, c, g, or t

<400> SEQUENCE: 31
nnnnnnnnnn ggatcc                                                     16

<210> SEQ ID NO 32
<211> LENGTH: 20
<212> TYPE: DNA
<213> ORGANISM: Artificial
<220> FEATURE:
<223> OTHER INFORMATION: synthetic primer

<400> SEQUENCE: 32
ttaccacgaa tcagaggacc                                                 20

<210> SEQ ID NO 33
<211> LENGTH: 20
<212> TYPE: DNA
<213> ORGANISM: Artificial
<220> FEATURE:
<223> OTHER INFORMATION: synthetic primer

<400> SEQUENCE: 33
cctcacctgt attggcacag                                                 20

<210> SEQ ID NO 34
<211> LENGTH: 20
<212> TYPE: DNA
<213> ORGANISM: Artificial
<220> FEATURE:
<223> OTHER INFORMATION: synthetic primer

<400> SEQUENCE: 34
ttggtatcat gcccttgctc                                                 20

<210> SEQ ID NO 35
<211> LENGTH: 20
<212> TYPE: DNA
<213> ORGANISM: Artificial
<220> FEATURE:
<223> OTHER INFORMATION: synthetic primer

<400> SEQUENCE: 35
ttcgcaggtc aacgatattc                                                 20

<210> SEQ ID NO 36
<211> LENGTH: 20
<212> TYPE: DNA
<213> ORGANISM: Artificial
<220> FEATURE:
<223> OTHER INFORMATION: synthetic primer

<400> SEQUENCE: 36
gttaggtggt tgaaggattg                                                 20

<210> SEQ ID NO 37
<211> LENGTH: 1316
<212> TYPE: DNA
<213> ORGANISM: Cerrena unicolor

<400> SEQUENCE: 37
ttcgcaggtc aacgatattc gttcgtcgta agtctctttg aacgattact gcttctttgt     60
ccattctctg acctgtttaa acagctccat gccaaccgtc ctgaaaacaa ctattggatc    120
agggccaaac ctaatatcgg tacggatact accacagaca acggcatgaa ctctgccatt    180
```

-continued

```
ctgcgataca acggcgcacc tgttgcggaa ccgcaaactg ttcaatctcc cagtctcacc      240
cctttgctcg aacagaacct tcgccctctc gtgtacactc ctgtggtatg tttcaaagcg      300
ttgtaatttg attgtggtca ttctaacgtt actgcgtttg catagcctgg aaatcctacg      360
cctggcggcg ccgatattgt ccatattctt gacttgagtt ttgtgcggag tcaacattcg      420
taaagatgag agtgtttcta atttcttcaa aataggatg ctggtcgctt cagtatcaac       480
ggtgcctcgt tccttgatcc taccgtcccc gttctcctgc aaattctcag cggcacgcag      540
aatgcacaag atctactccc tcctggaagt gtgattcctc tcgaattagg caaggtcgtc      600
gaattagtca tacctgcagg tgtcgtcggt ggacctcatc cgttccatct ccatggggta      660
cgtaacccga acttataaca gtcttggact tacccgctga caagtgtata gcataacttc      720
tgggtcgtgc gaagtgccgg aaccgaccag tacaacttta acgatgccat tctccgagac     780
gtcgtcagta taggaggaac cggggatcaa gtcaccattc gtttcgtggt atgtttcatt     840
cttgtggatg tatgtgctct aggatactaa ccggcttacg cgtatagacc gataaccccg      900
gaccgtggtt cctccattgc catatcgact ggcacttgga agcgggtctc gctatcgtat      960
ttgcagaggg aattgaaaat actgctgcgt ctaatccaac cccccgtacg tggtttccct     1020
cacatcgtgg atctaagcag cttactaaca tacatttgca gaggcttggg atgagctttg     1080
cccgaagtat aacgcgctca gcgcacaaaa gaaggttgca tctaagaaag gcactgccat     1140 ctaattttg taacaaacaa ggagggtctc ttgtactttt attgggattt atttcttggg      1200
gtttgttgtt caacttgatt ctactatgtt tggaagtagc gatgacgaaa ggggctcgcg     1260
catttatata ctatctctct tggcatcacc tgcagctcaa tccttcaacc acctaa        1316
```

```
<210> SEQ ID NO 38
<211> LENGTH: 16
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(10)
<223> OTHER INFORMATION: n is a, c, g, or t

<400> SEQUENCE: 38
nnnnnnnnnn cgatcg                                                         16

<210> SEQ ID NO 39
<211> LENGTH: 20
<212> TYPE: DNA
<213> ORGANISM: Artificial
<220> FEATURE:
<223> OTHER INFORMATION: synthetic primer

<400> SEQUENCE: 39
caatctatga ccgtagattc                                                     20

<210> SEQ ID NO 40
<211> LENGTH: 20
<212> TYPE: DNA
<213> ORGANISM: Artificial
<220> FEATURE:
<223> OTHER INFORMATION: synthetic primer

<400> SEQUENCE: 40
accgtggttc ctccattgcc                                                     20
```

```
<210> SEQ ID NO 41
<211> LENGTH: 20
<212> TYPE: DNA
<213> ORGANISM: Artificial
<220> FEATURE:
<223> OTHER INFORMATION: synthetic primer

<400> SEQUENCE: 41
gactggcact tggaagcggg                                          20

<210> SEQ ID NO 42
<211> LENGTH: 19
<212> TYPE: DNA
<213> ORGANISM: Artificial
<220> FEATURE:
<223> OTHER INFORMATION: synthetic primer

<400> SEQUENCE: 42
ggaccaagct ggtactttc                                           19

<210> SEQ ID NO 43
<211> LENGTH: 21
<212> TYPE: DNA
<213> ORGANISM: Artificial
<220> FEATURE:
<223> OTHER INFORMATION: synthetic primer

<400> SEQUENCE: 43
cgtggtacca gtctgccagg g                                        21

<210> SEQ ID NO 44
<211> LENGTH: 21
<212> TYPE: DNA
<213> ORGANISM: Artificial
<220> FEATURE:
<223> OTHER INFORMATION: synthetic primer

<400> SEQUENCE: 44
ggcagcatca gtcacggtca g                                        21

<210> SEQ ID NO 45
<211> LENGTH: 23
<212> TYPE: DNA
<213> ORGANISM: Artificial
<220> FEATURE:
<223> OTHER INFORMATION: synthetic primer

<400> SEQUENCE: 45
caccagcatg agctcaaagc tac                                      23

<210> SEQ ID NO 46
<211> LENGTH: 24
<212> TYPE: DNA
<213> ORGANISM: Artificial
<220> FEATURE:
<223> OTHER INFORMATION: synthetic primer

<400> SEQUENCE: 46
caccgcgatg tctcttcttc gtag                                     24

<210> SEQ ID NO 47
<211> LENGTH: 23
<212> TYPE: DNA
<213> ORGANISM: Artificial
<220> FEATURE:
<223> OTHER INFORMATION: synthetic primer

<400> SEQUENCE: 47
```

```
tgragrtgga asggatgwgg tcc                                            23

<210> SEQ ID NO 48
<211> LENGTH: 22
<212> TYPE: DNA
<213> ORGANISM: Artificial
<220> FEATURE:
<223> OTHER INFORMATION: synthetic primer

<400> SEQUENCE: 48
gtccctgtac tactccagat cc                                             22

<210> SEQ ID NO 49
<211> LENGTH: 22
<212> TYPE: DNA
<213> ORGANISM: Artificial
<220> FEATURE:
<223> OTHER INFORMATION: synthetic primer

<400> SEQUENCE: 49
ccagcaggaa gcgtgatcga ac                                             22

<210> SEQ ID NO 50
<211> LENGTH: 27
<212> TYPE: DNA
<213> ORGANISM: Artificial
<220> FEATURE:
<223> OTHER INFORMATION: synthetic primer

<400> SEQUENCE: 50
gtaatcatgt atcacctggg ctcaagg                                        27

<210> SEQ ID NO 51
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 51
acgaacgagt ancgttgncc                                                20

<210> SEQ ID NO 52
<211> LENGTH: 7
<212> TYPE: PRT
<213> ORGANISM: Cerrena unicolor

<400> SEQUENCE: 52

Gly Gln Arg Tyr Ser Phe Val
1               5

<210> SEQ ID NO 53
<211> LENGTH: 19
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (11)..(11)
```

```
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 53
ctggttggtt ngcattnag                                                  19

<210> SEQ ID NO 54
<211> LENGTH: 6
<212> TYPE: PRT
<213> ORGANISM: Cerrena unicolor

<400> SEQUENCE: 54

Leu Asn Ala Asn Gln Pro
 1               5

<210> SEQ ID NO 55
<211> LENGTH: 20
<212> TYPE: DNA
<213> ORGANISM: Artificial
<220> FEATURE:
<223> OTHER INFORMATION: synthetic primer

<400> SEQUENCE: 55
cacacgaccc ctgaccgttg                                                 20

<210> SEQ ID NO 56
<211> LENGTH: 20
<212> TYPE: DNA
<213> ORGANISM: Artificial
<220> FEATURE:
<223> OTHER INFORMATION: synthetic primer

<400> SEQUENCE: 56
tgaccggtga tcaacgtccc                                                 20

<210> SEQ ID NO 57
<211> LENGTH: 20
<212> TYPE: DNA
<213> ORGANISM: Artificial
<220> FEATURE:
<223> OTHER INFORMATION: synthetic primer

<400> SEQUENCE: 57
ggcgcagaca tcaatcacag                                                 20

<210> SEQ ID NO 58
<211> LENGTH: 20
<212> TYPE: DNA
<213> ORGANISM: Artificial
<220> FEATURE:
<223> OTHER INFORMATION: synthetic primer

<400> SEQUENCE: 58
tcttcagcat caacaacgcc                                                 20

<210> SEQ ID NO 59
<211> LENGTH: 18
<212> TYPE: DNA
<213> ORGANISM: Artificial
<220> FEATURE:
<223> OTHER INFORMATION: synthetic primer

<400> SEQUENCE: 59
tccggcaagc acggttgg                                                   18
```

<210> SEQ ID NO 60
<211> LENGTH: 20
<212> TYPE: DNA
<213> ORGANISM: Artificial
<220> FEATURE:
<223> OTHER INFORMATION: synthetic primer

<400> SEQUENCE: 60
tcgtcttcgc tgagggcatc                                         20

<210> SEQ ID NO 61
<211> LENGTH: 20
<212> TYPE: DNA
<213> ORGANISM: Artificial
<220> FEATURE:
<223> OTHER INFORMATION: synthetic primer

<400> SEQUENCE: 61
cagaccgctg cagccaaccc                                         20

<210> SEQ ID NO 62
<211> LENGTH: 20
<212> TYPE: DNA
<213> ORGANISM: Artificial
<220> FEATURE:
<223> OTHER INFORMATION: synthetic primer

<400> SEQUENCE: 62
aacacggaga cagtccaaac                                         20

<210> SEQ ID NO 63
<211> LENGTH: 23
<212> TYPE: DNA
<213> ORGANISM: Artificial
<220> FEATURE:
<223> OTHER INFORMATION: synthetic primer

<400> SEQUENCE: 63
cacctctcga gatgggattg aac                                     23

<210> SEQ ID NO 64
<211> LENGTH: 22
<212> TYPE: DNA
<213> ORGANISM: Artificial
<220> FEATURE:
<223> OTHER INFORMATION: synthetic primer

<400> SEQUENCE: 64
cgtttaaata gcagttcctt tc                                      22

<210> SEQ ID NO 65
<211> LENGTH: 48
<212> TYPE: DNA
<213> ORGANISM: Artificial
<220> FEATURE:
<223> OTHER INFORMATION: synthetic primer

<400> SEQUENCE: 65
ggactagtgt cgccgtttac aaacgcgcaa tcggtccagt cactgacc          48

<210> SEQ ID NO 66
<211> LENGTH: 2159
<212> TYPE: DNA
<213> ORGANISM: Artificial
<220> FEATURE:
<223> OTHER INFORMATION: synthetic PCR fragment

<400> SEQUENCE: 66

```
actagtgtcg ccgtttacaa acgcgcaatc ggtccagtca ctgacctaca tatagtgaac      60
cagaatctcg acccagatgg tttcaaccgc cccactgtac tcgcaggtgg tactttcccc     120
ggtcctctga ttcgtggtaa caaggtacgc ttcataaccg ccctccgtag acgtaggctt     180
cggctgacat gaccatcatc tgtagggaga taactttaaa attaatgtga ttgacgactt     240
gacagagcac agtatgctca aggctacgtc catcgtaagt ccctgattaa cgtttcacct     300
ggtcatatcg ctcaacgtct cgaagcactg gcatgggttc ttccagaagg gaaccaactg     360
ggccgatggc cccgcctttg tcacccaatg tcctatcaca tcaggaaacg ccttcctgta     420
tgatttcaac gttccggacc aagctggtac tttctggtac cacagccatc tctctacaca     480
gtattgtgac ggtcttcgtg gtgcctttgt cgtctatgat cctaatgatc ccaacaagca     540
actctatgat gttgataacg gcaagttcct tgcatatttc atttctatca tatcctcacc     600
tgtattggca cagaaagcac cgtgattacc ttggctgatt ggtatcatgc ccttgctcag     660
actgtcactg gtgtcgcgtg agtgacaaat ggccctcaat tgttcacata ttttcctgat     720
tatcatatga tagagtatct gatgcaacgt tgatcaacgg attgggacgt tcggccaccg     780
gccccgcaaa tgcccctctg gcggtcatca gtgtcgagcg aataagagg tcagttccat      840
aattatgatt atttcccgcg ttacttccta acaattattt ttgtatccct ccacagatat     900
cgtttccgat tggtttctat ttcttgcgac cctaacttta ttttctcaat tgaccaccac     960
ccaatgaccg taattgagat ggacggtgtt aatacccaat ctatgaccgt agattcgatc    1020
caaatattcg caggtcaacg atattcattt gtcgtaggtt attataaact gcccaccgat    1080
catctctcac gtaactgtta tagatgcaag ccaaccaacc agttggaaat tattggatcc    1140
gcgctaaacc taatgttggg aacacaactt tccttggagg cctgaactcc gctatattac    1200
gatatgtggg agcccctgac caagaaccga ccactgacca acacccaac tctacaccgc     1260
tcgttgaggc gaacctacga ccccctcgtct atactcctgt ggtatgttgt tctcgttaca    1320
tataccaaac ctaatatgaa gactgaacgg atctactagc cgggacagcc attccctggc    1380
ggtgctgata tcgtcaagaa cttagctttg ggtttcgtac gtgtatttca cttccctttt    1440
ggcagtaact gaggtggaat gtatatagaa tgccgggcgt ttcacaatca atggagcgtc    1500
cctcacacct cctacagtcc ctgtactact ccagatcctc agtggtactc acaatgcaca    1560
ggatcttctc ccagcaggaa gcgtgatcga acttgaacag aataaagttg tcgaaatcgt    1620
tttgcccgct gcgggcgccg ttggcggtcc tcatcctttt cacttacatg gtgtaagtat    1680
cagacgtcct catgcccata ttgctccgaa ccttacacac ctgatttcag cacaatttct    1740
gggtggttcg tagcgccggt caaaccacat acaatttcaa tgatgctcct atccgtgatg    1800
ttgtcagtat tggcggtgca aacgatcaag tcacgatccg atttgtggta tgtatctcgt    1860
gccttgcatt cattccacga gtaatgatcc ttacacttcg ggttctcaga ccgataaccc    1920
tggcccatgg ttccttcact gtcacattga ctggcatttg gaggctgggt tcgctgtagt    1980
ctttgcggag ggaatcaatg gtactgcagc tgctaatcca gtcccaggta agactctcgc    2040
tgctttgcgt aatatctatg aatttaaatc atatcaattt gcagcggctt ggaatcaatt    2100
gtgcccattg tatgatgcct tgagcccagg tgatacatga ttacaagggt gggcgcgcc    2159
```

<210> SEQ ID NO 67
<211> LENGTH: 1523
<212> TYPE: DNA
<213> ORGANISM: Artificial
<220> FEATURE:
<223> OTHER INFORMATION: synthetic codon optimized laccase B

<400> SEQUENCE: 67

```
actagtgtcg ccgtttacaa acgcgcaatc ggtcccgtca ctgacctgca tattgtgaac    60
cagaatctcg accccgatgg tttcaaccgc cccactgtcc tcgcaggtgg tactttcccc   120
ggtcctctga ttcgtggtaa caagggagat aactttaaaa ttaatgtgat tgacgacttg   180
acagagcaca gcatgctcaa ggctacgtcc atccactggc atggcttctt ccagaaggga   240
accaactggg ccgatggccc cgcctttgtc acccaatgtc ctatcacatc aggaaacgcc   300
ttcctgtacg atttcaacgt tccggaccaa gctggtactt tctggtacca cagccatctc   360
tctacacagt actgtgacgg tcttcgtggt gcctttgtcg tctacgatcc taatgatccc   420
aacaagcaac tctacgatgt tgataacggc aacaccgtga ttaccttggc tgattggtac   480
catgcccttg ctcagactgt cactggtgtc gcagtctctg atgcaacgtt gatcaacgga   540
ttgggacgtt cggccaccgg ccccgcaaat gcccctctgg cggtcatcag cgtcgagcgc   600
aataagcgct atcgtttccg attggtttct atttcttgcg accctaactt tattttctca   660
attgaccacc accccatgac cgtcattgag atggacggtg ttaatacccca atctatgacc   720
gtagattcga tccaaatctt cgcaggtcaa cgatactcat tgtcatgca agccaaccaa    780
ccagttggaa attactggat ccgcgctaaa cctaatgttg caacacaac tttccttgga    840
ggcctgaact ccgctatctt gcgatacgtg ggagccctg accaagaacc gaccactgac    900
caaacaccca actctacacc gctcgttgag gcgaacctgc gaccctcgt ctacactcct    960
gtgccgggac agccattccc tggcggtgct gatatcgtca agaacttggc tttgggtttc  1020
aatgccgggc gtttcacaat caatggagcg tccctcacac ctcctacagt ccctgtcctg  1080
ctccagatcc tcagcggtac tcacaatgca caggatcttc tcccggcagg aagcgtgatc  1140
gaacttgaac agaataaagt tgtcgaaatc gttttgcccg ctgcgggcgc cgttggcggt  1200
cctcatcctt ttcacttgca tggtcacaat ttctgggtgg ttcgtagcgc cggtcaaacc  1260
acatacaatt tcaatgatgc tcctatccgt gatgttgtca gcattggcgg tgcaaacgat  1320
caagtcacga tccgatttgt gaccgataac cctggcccat ggttccttca ctgtcacatt  1380
gactggcatt tggaggctgg attcgctgtc gtctttgcgg agggaatcaa tggtactgca  1440
gctgctaatc ccgtcccggc ggcttggaat caattgtgcc cgttgtacga tgccttgagc  1500
ccgggtgata catgaggcgc gcc                                           1523
```

<210> SEQ ID NO 68
<211> LENGTH: 47
<212> TYPE: DNA
<213> ORGANISM: Artificial
<220> FEATURE:
<223> OTHER INFORMATION: synthetic primer

<400> SEQUENCE: 68

```
ggactagtgt cgccgtttac aaacgcgcaa ttgggcccgt ggccgac                 47
```

<210> SEQ ID NO 69
<211> LENGTH: 33
<212> TYPE: DNA
<213> ORGANISM: Artificial
<220> FEATURE:
<223> OTHER INFORMATION: synthetic primer

<400> SEQUENCE: 69

```
aaggcgcgcc ttaaatagca gttcctttct tag                                33
```

<210> SEQ ID NO 70
<211> LENGTH: 1550
<212> TYPE: DNA
<213> ORGANISM: Artificial
<220> FEATURE:
<223> OTHER INFORMATION: synthetic codon optimized laccase D

<400> SEQUENCE: 70

| | | | | | |
|---|---|---|---|---|---|
| actagtgtcg | ccgtttacaa | acgcgctatt | ggaccagttg | ctgatctgca | catcgttaac | 60 |
| aaggatttgg | ccccagacgg | cgtccagcgc | ccaactgttc | tggccggtgg | aacttttccg | 120 |
| ggcacgctga | ttaccggtca | aaagggcgac | aacttccagc | tgaacgtgat | tgatgacctg | 180 |
| accgacgatc | gcatgttgac | ccctacttcg | atccattggc | atggtttctt | ccagaaggga | 240 |
| accgcctggg | ccgacggtcc | ggctttcgtt | acacagtgcc | ctattatcgc | agacaactcc | 300 |
| ttcctctacg | atttcgacgt | tcccgaccag | gcgggcacct | tctggtacca | ctcacacttg | 360 |
| tctacacagt | actgcgacgg | tctgcgcggt | gccttcgttg | tttacgaccc | caacgaccct | 420 |
| cacaaggacc | tttatgatgt | cgatgacggt | ggcacagtta | tcacattggc | tgactggtat | 480 |
| cacgtcctcg | ctcagaccgt | tgtcggagct | gctacacccg | actctacgct | gattaacggc | 540 |
| ttgggacgca | gccagactgg | ccccgccgac | gctgagctgg | ccgttatctc | tgttgaacac | 600 |
| aacaagagat | accgtttcag | actcgtctcc | atctcgtgcg | atcccaactt | cacttttagc | 660 |
| gtcgacggtc | acaacatgac | ggttatcgag | gttgatggcg | tgaatacccg | ccctctcacc | 720 |
| gtcgattcca | ttcaaatttt | cgccggccag | cgatactcct | tgtgctgaa | tgccaatcag | 780 |
| cccgaggata | actactggat | ccgcgctatg | cctaacatcg | gacgaaacac | cactacccct | 840 |
| gatggcaaga | atgccgctat | cctgcgatac | aagaacgcca | gcgttgagga | gcccaaaacc | 900 |
| gtcggaggac | ccgcgcagag | cccattgaac | gaggccgacc | tgcgacctct | ggtgcccgct | 960 |
| cctgtccctg | gcaacgcagt | tcctggtggt | gcggacatca | accaccgcct | gaacctgaca | 1020 |
| ttcagcaacg | gcctcttctc | tatcaataac | gcatcattta | caaaccccag | cgtccctgcc | 1080 |
| ttgttgcaga | ttcttttccgg | cgcacaaaac | gctcaggatc | tgcttcccac | cggttcttat | 1140 |
| atcggcttgg | agttgggcaa | ggtcgttgaa | ctcgtgatcc | ctcccttggc | cgttggtggc | 1200 |
| ccccatccat | tccacttgca | cggccacaac | ttttgggtcg | tccgaagcgc | tggttctgac | 1260 |
| gagtataatt | tcgacgatgc | aattttgcgc | gacgtggtca | gcattggcgc | gggaactgac | 1320 |
| gaggttacta | tccgtttttgt | cactgataac | ccaggcccctt | ggttcctcca | ttgccacatc | 1380 |
| gactggcacc | tcgaagccgg | cctcgccatt | gttttcgccg | aaggcatcaa | tcaaaccgca | 1440 |
| gccgccaacc | cgactccaca | ggcctgggac | gaactctgcc | ccaagtataa | cggactctcc | 1500 |
| gcttcccaga | aagtgaagcc | caagaaggga | acagccatct | aaggcgcgcc | | 1550 |

<210> SEQ ID NO 71
<211> LENGTH: 1507
<212> TYPE: DNA
<213> ORGANISM: Artificial
<220> FEATURE:
<223> OTHER INFORMATION: synthetic codon optimized laccase D

<400> SEQUENCE: 71

| | | | | | |
|---|---|---|---|---|---|
| ggatcctgaa | gctatcggtc | cggttgcaga | tttacacatc | gtaaacaaag | atcttgcacc | 60 |
| tgacggcgtt | caacgtccaa | ctgtacttgc | tggtggaaca | ttccctggta | cacttattac | 120 |
| tggtcaaaaa | ggtgacaaact | tccaattaaa | cgtaattgac | gatcttacag | atgaccgtat | 180 |
| gcttacaccg | acttcaattc | actggcacgg | tttctttcaa | aaaggaacag | catgggctga | 240 |

-continued

```
tggtcctgca ttcgttacac aatgtccaat cattgctgat aactctttcc tttacgattt    300
tgacgttcct gatcaagctg gtacattctg gtatcactca cacttatcca cacaatactg    360
cgatggactt cgcggagctt tcgtagttta cgacccaaac gatcctcata aagaccttta    420
cgatgtagat gatggtggaa cagttatcac attagctgat tggtaccatg tacttgctca    480
aacagttgta ggtgcagcta caccagattc aacacttatc aatggattag gacgttctca    540
aactggtcct gctgacgcag aacttgctgt aatctctgtt gaacataaca aacgttacag    600
attccgtctt gttagcattt cttgcgatcc aaacttcaca ttttcagttg acggacataa    660
catgacagtt atcgaagtag atggtgtaaa cacacgtcca cttactgtag actctatcca    720
aatcttcgca ggacaacgtt actcattcgt attaaacgca atcaaccag aagataacta    780 ctggattcgt gcaatgccaa acatcggacg taacactaca actcttgacg gcaaaaacgc    840
agctattctt cgttacaaaa acgcttctgt tgaagaacct aaaacagttg gtggaccagc    900
acaatcacca cttaacgaag ctgacttacg tccactggtt ccagcacctg tacctggaaa    960
cgctgtacca ggaggtgctg atattaatca tagacttaac cttactttct ctaacggtct   1020
gttctcaatc aacaacgctt cattcacaaa tccttcagtt ccagcacttt tacaaattct   1080
tagcggtgca caaaatgctc aggatctttt accaactgga tcttacattg gtcttgaact   1140
gggtaaagta gttgaattag taattcctcc gcttgctgta ggtggaccac atcctttcca   1200
tcttcacggt cataacttct gggttgtacg ttctgctggt tcagatgaat caacttcga    1260 tgacgcaatt cttcgtgatg ttgtatctat tggtgctgga acagatgaag taactattcg   1320
tttcgtaaca gataaccctg gtccttggtt cttacattgt catatcgatt ggcatcttga   1380
agctggactt gctattgttt tcgctgaagg aatcaatcaa acagctgcag ctaacccaac   1440
acctcaagca tgggacgaat tatgtccaaa atacaacgca ctttctccag agatactta    1500 aaagctt                                                             1507
```

<210> SEQ ID NO 72
<211> LENGTH: 34
<212> TYPE: DNA
<213> ORGANISM: Artificial
<220> FEATURE:
<223> OTHER INFORMATION: synthetic primer

<400> SEQUENCE: 72
gcagatctgc gatgtctctt cttcgtagct tgac                                34

<210> SEQ ID NO 73
<211> LENGTH: 42
<212> TYPE: DNA
<213> ORGANISM: Artificial
<220> FEATURE:
<223> OTHER INFORMATION: synthetic primer

<400> SEQUENCE: 73
gaggtcacct ctagatcatg tatcacctgg gctcaaggca tc                        42

<210> SEQ ID NO 74
<211> LENGTH: 51
<212> TYPE: DNA
<213> ORGANISM: Artificial
<220> FEATURE:
<223> OTHER INFORMATION: synthetic primer

<400> SEQUENCE: 74
ttgctagcaa cgtgatctcc aagcgtgcaa tcggtccagt cactgaccta c              51

```
<210> SEQ ID NO 75
<211> LENGTH: 32
<212> TYPE: DNA
<213> ORGANISM: Artificial
<220> FEATURE:
<223> OTHER INFORMATION: synthetic primer

<400> SEQUENCE: 75
acgcagcctg aactagttgc gatcctctag ag                                    32

<210> SEQ ID NO 76
<211> LENGTH: 37
<212> TYPE: DNA
<213> ORGANISM: Artificial
<220> FEATURE:
<223> OTHER INFORMATION: synthetic primer

<400> SEQUENCE: 76
ctctgatcaa ggtcatcagg tgtcgcccgg ggacagg                               37

<210> SEQ ID NO 77
<211> LENGTH: 6
<212> TYPE: PRT
<213> ORGANISM: Artificial
<220> FEATURE:
<223> OTHER INFORMATION: synthetic Kex2 site

<400> SEQUENCE: 77

Asn Val Ile Ser Lys Arg
1               5
```

US 8,105,812 B2

LACCASES, COMPOSITIONS AND METHODS OF USE

CROSS-REFERENCE TO RELATED APPLICATIONS

The present application claims priority to U.S. Provisional Patent Application Ser. No. 60/875,518, entitled "Novel Laccases, Compositions and Methods of Use", filed 18 Dec. 2006 and U.S. Provisional Patent Application Ser. No. 60/875,454, entitled "Laccase Mediators and Methods of Use", filed 18 Dec. 2006.

FIELD OF THE INVENTION

The present invention relates to laccases and nucleic acid sequences encoding the laccases, and to enzymatic methods for bleaching materials.

BACKGROUND OF THE INVENTION

Laccases are copper-containing enzymes that are known to be good oxidizing agents in the presence of oxygen. Laccases are found in microbes, fungi, and higher organisms. Laccase enzymes are used for many applications, including pulp and textiles bleaching, treatment of pulp waste water, de-inking, industrial color removal, bleaching laundry detergents, oral care teeth whiteners, and as catalysts or facilitators for polymerization and oxidation reactions.

Laccases can be utilized for a wide variety of applications in a number of industries, including the detergent industry, the paper and pulp industry, the textile industry and the food industry. In one application, phenol oxidizing enzymes are used as an aid in the removal of stains, such as food stains, from clothes during detergent washing.

Most laccases exhibit pH optima in the acidic pH range while being inactive in neutral or alkaline pHs.

Laccases are known to be produced by a wide variety of fungi, including species of the genii *Aspergillus, Neurospora, Podospora, Botrytis, Pleurotus, Fornes, Phlebia, Trametes, Polyporus, Stachybotrys, Rhizoctonia, Bipolaris, Curvularia, Amerosporium,* and *Lentinus.* However, there remains a need for laccases having different performance profiles in various applications.

For many applications, the oxidizing efficiency of a laccase can be improved through the use of a mediator, also known as an enhancing agent. Systems that include a laccase and a mediator are known in the art as laccase-mediator systems (LMS). The same compounds can also be used to activate or initiate the action of laccase.

There are several known mediators for use in a laccase-mediator system. These include HBT (1-hydroxybenzotriazole), ABTS [2,2'-azinobis(3-ethylbenzothiazoline-6-sulfinic acid)], NHA (N-hydroxyacetanilide), NEIAA (N-acetyl-N-phenylhydroxylamine), HBTO (3-hydroxy 1,2,3-benzotriazin-4(3H)-one), and VIO (violuric acid). In addition, there are several compounds containing NH—OH or N—O that have been found to be useful as mediators.

Functional groups and substituents have large effects on mediator efficiency. Even within the same class of compounds, a substituent can change the laccase specificity towards a substrate, thereby increasing or decreasing mediator efficiency greatly. In addition, a mediator may be effective for one particular application but unsuitable for another application. Another drawback for current mediators is their tendency to polymerize during use. Thus, there is a need to discover efficient mediators for specific applications. One such application is the bleaching of textiles, wherein it is also important that the mediators are not unduly expensive or hazardous. Other applications of the laccase-mediator system are given below.

Thus, there is a need to identify additional mediators that activate laccase, and/or enhance the activity of enzymes that exhibit laccase activity.

SUMMARY OF THE INVENTION

Described herein are novel laccases, nucleic acid sequences encoding such laccases, and vectors and host cells for expressing the laccases.

DETAILED DESCRIPTION OF THE INVENTION

Figure 1:
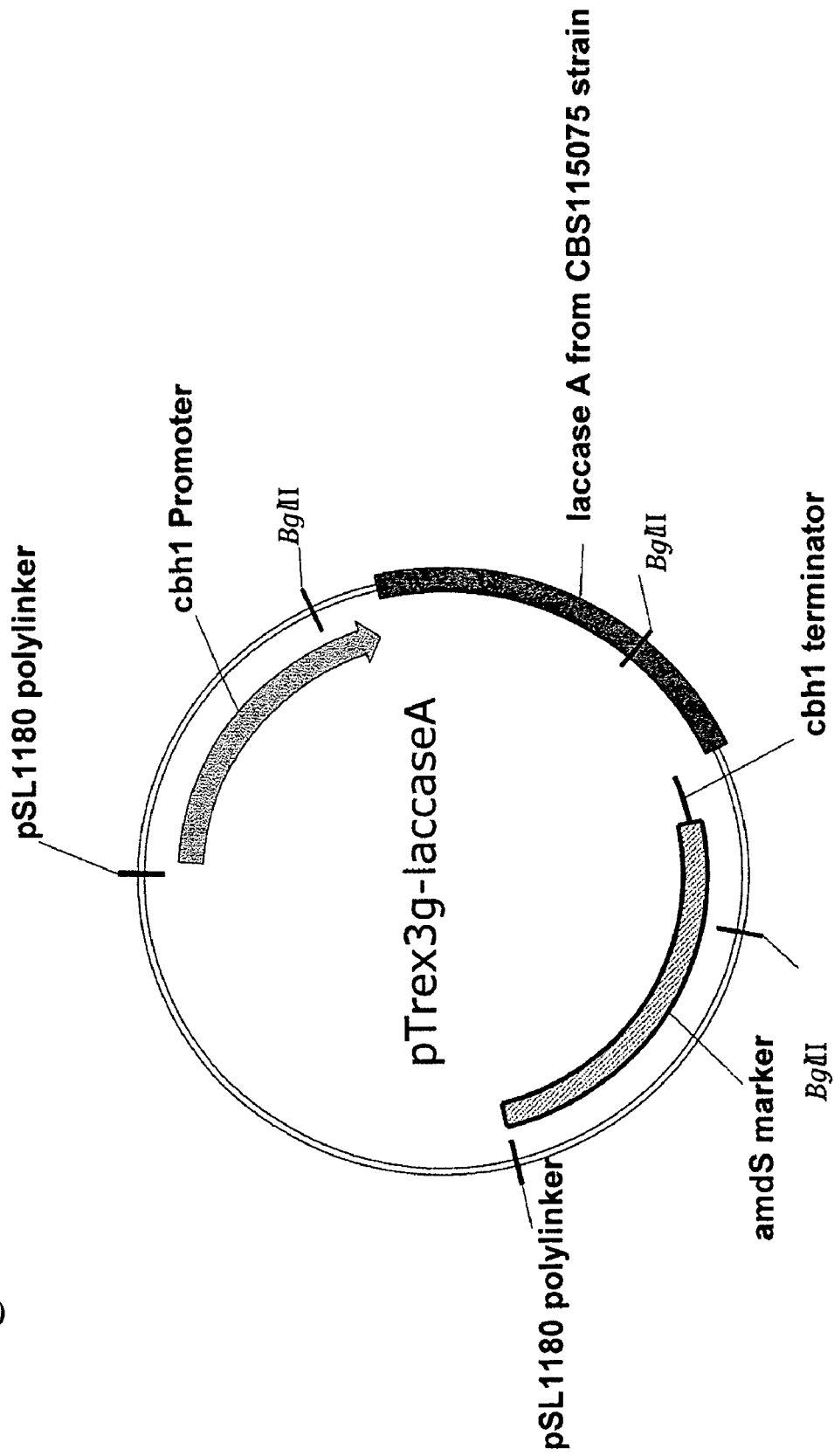
FIG. 1 is a schematic of the *Trichoderma* expression plasmid, pTrex3g-laccaseA, used in Example 7. The laccase A gene may be replaced with other laccase genes described herein.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Laccase and Laccase Related Enzymes

In the context of this invention, laccases and laccase related enzymes contemplate any laccase enzyme comprised by the enzyme classification (EC 1.10.3.2). The laccase enzymes are known from microbial and plant origin. The microbial laccase enzyme may be derived from bacteria or fungi (including filamentous fungi and yeasts) and suitable examples include a laccase derivable from a strain of *Aspergillus, Neurospora*, e.g. *N. crassa. Podospora, Botrytis, Collybia, Cerrena, Stachybotrys, Panus*,e.g., *Panus rudis, Theilava, Fomes, Lentinus, Pleurotus, Trametes*, e.g. *T. villosa* and *T. versicolor, Rhizoctonia*, e.g. *R. solani, Coprinus*, e.g. *C. plicatilis* and *C. cinereus, Psatyrella, Myceliophthora*, e.g. *M. thermonhila, Schytalidium, Phlebia*, e.g., *P. radita* (WO 92/01046), or *Coriolus*, e.g. *C. hirsutus* (JP 2--238885), *Spongipellis* sp., *Polyporus, Ceriporiopsis subvermispora, Ganoderma tsunodae* and *Trichoderma*.

The laccase or the laccase related enzyme may furthermore be produced by a method comprising cultivating a host cell transformed with a recombinant DNA vector which carries a DNA sequence encoding said laccase as well as DNA sequences permitting the expression of the DNA sequence encoding the laccase, in a culture medium under conditions permitting the expression of the laccase enzyme, and recovering the laccase from the culture.

The expression vector may be transformed into a suitable host cell, such as a fungal cell, preferred examples of which are species of *Aspergillus*, most preferably *Aspergillus oryzae* and *Aspergillus niger*, and species of *Fusarium*, most preferably *Fusarium venenatum*. Fungal cells may be transformed by a process involving protoplast formation and transformation of the protoplasts followed by regeneration of the cell wall in a manner known per se. The use of *Aspergillus* as a host microorganism is described in EP 238,023. The use of *Fusarium* as a host microorganism is described in WO 96/00787 and WO 97/08325.

Alternatively, the host organism may be a bacterium, in particular strains of *Bacillus, Pseudomonas, Streptomyces*, or *E. coli*. The transformation of bacterial cells may be performed according to conventional methods, e.g., as described in T. Maniatis et al., Molecular Cloning: A Laboratory Manual, Cold Spring Harbor, 1982. The screening of appropriate DNA sequences and construction of vectors may also be carried out by standard procedures, cf. T. Maniatis et al., op. cit.

The medium used to cultivate the transformed host cells may be any conventional medium suitable for growing the host cells in question. The expressed enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

In an embodiment, the expression host may be a *Trichoderma reesei* with the laccase coding region under the control of a CBH1 promoter and terminator. (See, e.g., U.S. Pat. No. 5,861,271). The expression vector may be pTrex3g, as disclosed in U.S. patent application Ser. No. 11/245,628 filed 7 Oct. 2005.

In this manner the following novel genes and laccases were prepared:

```
A. Cerrena laccase A1 gene from CBS115.075 strain
(SEQ ID No. 1) having the sequence
ATGAGCTCAA AGCTACTTGC TCTTATCACT GTCGCTCTCG TCTTGCCACT      50

AGGCACCGAC GCCGGCATCG GTCCTGTTAC CGACTTGCGC ATCACCAACC     100

AGGATATCGC TCCAGATGGC TTCACCCGAC CAGCGGTACT AGCTGGGGGC     150

ACATTCCCTG GAGCACTTAT TACCGGTCAG AAGGTATGGG AGATCAACTT     200

GGTTGAATAG AGAAATAAAA GTGACAACAA ATCCTTATAG GGAGACAGCT     250

TCCAAATCAA TGTCATCGAC GAGCTTACCG ATGCCAGCAT GTTGACCCAG     300

ACATCCATTG TGAGTATAAT TTAGGTCCGC TCTTCTGGCT ATCCTTTCTA     350

ACTCTTACCG TCTAGCATTG GCACGGCTTC TTTCAGAAGG GATCTGCGTG     400

GGCCGATGGT CCTGCCTTCG TTACTCAATG CCCTATCGTC ACCGGAAATT     450

CCTTCCTGTA CGACTTTGAT GTTCCCGACC AACCTGGTAC TTTCTGGTAC     500

CATAGTCACT TGTCTACTCA ATATTGCGAT GGTCTTCGTG GCCCGTTCGT     550

TGTATACGAT CCAAAGGATC CTAATAAACG GTTGTACGAC ATTGACAATG     600

GTATGTGCAT CATCATAGAG ATATAATTCA TGCAGCTACT GACCGTGACT     650

GATGCTGCCA GATCATACGG TTATTACCCT GGCAGACTGG TACCACGTTC     700
```

```
TCGCAAGAAC TGTTGTCGGA GTCGCGTAAG TACAGTCTCA CTTATAGTGG        750

TCTTCTTACT CATTTTGACA TAGGACACCC GACGCAACCT TGATCAACGG        800

TTTGGGCCGT TCTCCAGACG GGCCAGCAGA TGCTGAGTTG GCTGTCATCA        850

ACGTTAAACG CGGCAAACGG TATGTTATTG AACTCCCGAT TTCTCCATAC        900

ACAGTGAAAT GACTGTCTGG TCTAGTTATC GATTTCGTCT GGTCTCCATC        950

TCATGTGACC CTAATTACAT CTTTTCTATC GACAACCATT CTATGACTGT       1000

CATCGAAGTC GATGGTGTCA ACACCCAATC CCTGACCGTC GATTCTATTC       1050

AAATCTTCGC AGGCCAACGA TACTCGTTCG TCGTAAGTCT CTTTGCACGA       1100

TTACTGCTTC TTTGTCCATT CTCTGACCTG TTTAAACAGC TCCATGCCAA       1150

CCGTCCTGAA AACAACTATT GGATCAGGGC CAAACCTAAT ATCGGTACGG       1200

ATACTACCAC AGACAACGGC ATGAACTCTG CCATTCTGCG ATACAACGGC       1250

GCACCTGTTG CGGAACCGCA AACTGTTCAA TCTCCCAGTC TCACCCCTTT       1300

GCTCGAACAG AACCTTCGCC CTCTCGTGTA CACTCCTGTG GTATGTTTCA       1350

AAGCGTTGTA ATTTGATTGT GGTCATTCTA ACGTTACTGC GTTTGCATAG       1400

CCTGGAAACC CTACGCCTGG CGGCGCCGAT ATTGTCCATA CTCTTGACTT       1450

GAGTTTTGTG CGGAGTCAAC ATTCGTAAAG ATAAGAGTGT TTCTAATTTC       1500

TTCAATAATA GGATGCTGGT CGCTTCAGTA TCAACGGTGC CTCGTTCCTT       1550

GATCCTACCG TCCCCGTTCT CCTGCAAATT CTCAGCGGCA CGCAGAATGC       1600

ACAAGATCTA CTCCCTCCTG GAAGTGTGAT TCCTCTCGAA TTAGGCAAGG       1650

TCGTCGAATT AGTCATACCT GCAGGTGTCG TCGGTGGACC TCATCCGTTC       1700

CATCTCCATG GGGTACGTAA CCCGAACTTA TAACAGTCTT GGACTTACCC       1750

GCTGACAAGT GCATAGCATA ACTTCTGGGT CGTGCGAAGT GCCGGAACCG       1800

ACCAGTACAA CTTTAACGAT GCCATTCTCC GAGACGTCGT CAGTATAGGA       1850

GGAACCGGGG ATCAAGTCAC CATTCGTTTC GTGGTATGTT TCATTCTTGT       1900

GGATGTATGT GCTCTAGGAT ACTAACCGGC TTGCGCGTAT AGACCGATAA       1950

CCCCGGACCG TGGTTCCTCC ATTGCCATAT CGACTGGCAC TTGGAAGCGG       2000

GTCTCGCTAT CGTATTTGCA GAGGGAATTG AAAATACTGC TGCGTCTAAT       2050

TTAACCCCCC GTACGCGGTT TCCCTCACAT CCTGGAGCTA AGCAGCTTAC       2100

TAACATACAT TTGCAGAGGC TTGGGATGAG CTTTGCCCGA AGTATAACGC       2150

GCTCAGCGCA CAAAAGAAGG TTGCATCTAA GAAAGGCACT GCCATCTAAT       2200

TTTTGTAACA AACAAGGAGG GTCTCTTGTA CTTTTATTGG GATTTCTTTC       2250

TTGGGGTTTA TTGTTAAACT TGACTCTACT ATGTTTGGAA GACGAAAGGG       2300

GCTCGCGCAT TTATATACTA TCTCTCTTGG CATCACCTGC AGCTCAATCC       2350

TTCAACCACC TAA                                               2363
encoding the enzyme laccase A1, having the translated
protein sequence (SEQ ID No. 2)
MSSKLLALIT VALVLPLGTD AGIGPVTDLR ITNQDIAPDG FTRPAVLAGG         50

TFPGALITGQ KGDSFQINVI DELTDASMLT QTSIHWHGFF QKGSAWADGP        100

AFVTQCPIVT GNSFLYDFDV PDQPGTFWYH SHLSTQYCDG LRGPFVVYDP       150

KDPNKRLYDI DNDHTVITLA DWYHVLARTV VGVATPDATL INGLGRSPDG       200

PADAELAVIN VKRGKRYRFR LVSISCDPNY IFSIDNHSMT VIEVDGVNTQ       250

SLTVDSIQIF AGQRYSFVLH ANRPENNYWI RAKPNIGTDT TTDSGMNSAI       300
```

```
LRYNGAPVAE PQTVQSPSLT PLLEQNLRPL VYTPVPGNPT PGGADIVHTL    350

DLSFDAGRFS INGASFLDPT VPVLLQILSG TQNAQDLLPP GSVIPLELGK    400

VVELVIPAGV VGGPHPFHLH GHNFWVVRSA GTDQYNFNDA ILRDVVSIGG    450

TGDQVTIRFV TDNPGPWFLH CHIDWHLEAG LAIVFAEGIE NTAASNLTPQ    500

AWDELCPKYN ALSAQKKLNP STT                                523

B. Cerrena laccase A2 gene from CBS154.29 strain
(SEQ ID No. 3)
ATGAGCTCAA AGCTACTTGC TCTTATTACT GTCGCTCTCG TCTTGCCACT     50

AGGCACTGAC GCCGGCATCG GTCCTGTTAC CGACTTGCGC ATCACCAACC    100

AGGATATCGC TCCAGATGGC TTCACCCGAC CAGCTGTACT GGCTGGGGGC    150

ACATTCCCCG GAGCACTGAT TACCGGTCAG AAGGTATGGG AGATCGATTT    200

CGTTGAATAG AGAAATACAA CTGAAAACAA ATTCTTATAG GGAGACAGCT    250

TCCAAATCAA TGTCATCGAC GAGCTTACCG ATGCCAGCAT GTTGACCCAG    300

ACATCCATTG TGAGTATAAT ATGGGTCCGC TCTTCTAGCT ATCCTTTCTA    350

ACTCTTACCC TCTAGCATTG GCACGGCTTC TTTCAGAAGG GATCTGCGTG    400

GGCCGATGGT CCTGCCTTCG TTACTCAATG TCCTATCGTC ACCGGAAATT    450

CCTTCCTGTA CGACTTTGAT GTCCCCGACC AACCTGGTAC TTTCTGGTAC    500

CATAGTCACT TGTCTACTCA ATATTGCGAT GGTCTTCGGG GCCCGTTCGT    550

TGTATACGAT CCAAAGGATC CTAATAAACG GTTGTACGAC ATTGACAATG    600

GTATGTGCAT CATCATAAAA ATATAATTCA TGCAGCTACT GACCGCGACT    650

GATGCTGCCA GATCATACGG TTATTACCCT GGCAGACTGG TACCACGTTC    700

TCGCACGAAC TGTTGTCGGA GTCGCGTAAG TACAGTCTGA CTTATAGTGG    750

TCTTCTTACT CATTTTGACA TAGGACACCC GACGCAACCT TGATCAACGG    800

TTTGGGCCGT TCTCCAGACG GGCCAGCAGA TGCTGAGTTG GCTGTCATCA    850

ACGTTAAACG CGGCAAACGG TATGTCATTG AACTCCCGAT TCTCCATTC     900

ACATTGAAAT GACTGTCTGG TCTAGTTATC GATTCCGTCT GGTCTCCATC    950

TCATGTGACC CTAATTACAT CTTTTCTATC GACAACCATT CTATGACTGT   1000

CATCGAAGTC GATGGTGTCA ACACCCAATC CCTGACCGTC GATTCTATCC   1050

AAATCTTCGC AGGCCAACGC TACTCGTTCG TCGTAAGTCT CTTTGAATGG   1100

TTGGTGCTTT TTCTGTCCAT TCTCTAACCT GTTTATACAG CTCCATGCCA   1150

ACCGTCCTGA AAACAACTAT TGGATCAGGG CCAAACCTAA TATCGGTACG   1200

GATACTACCA CAGACAACGG CATGAACTCT GCCATTCTGC GATACAACGG   1250

CGCACCTGTT GCGGAACCGC AAACTGTTCA ATCTCCCAGT CTCACCCCTT   1300

TGCTCGAACA GAACCTTCGC CCTCTCGTGT ACACTCCTGT GGTATGTTTC   1350

AAAGCGTTGT AATTTGATTG TGGTCATTCT AACGTTACTG CCTTTGCACA   1400

GCCTGGAAAT CCTACGCCTG GCGGGGCCGA TATTGTCCAT ACTCTTGACT   1450

TGAGTTTTGT GCGGAGTCAA CATTCGTAAA GATAAGAGTG TTTCTAATTT   1500

CTTCAATAAT AGGATGCTGG TCGCTTCAGT ATCAACGGTG CCTCGTTCCT   1550

TGATCCTACC GTCCCTGTTC TCCTGCAAAT TCTCAGCGGC ACGCAGAATG   1600

CACAAGATCT ACTCCCTCCT GGAAGTGTGA TTCCTCTCGA ATTAGGCAAG   1650

GTCGTCGAAT TAGTCATACC TGCAGGTGTT GTCGGTGGAC CTCATCCGTT   1700
```

-continued

```
CCATCTCCAT GGGGTACGTA ACCCGAACTT ATAACAGTCT TGGACTTACC    1750

CGCTGACAAG TGTATAGCAT AACTTCTGGG TCGTGCGAAG TGCCGGAACC    1800

GACCAGTACA ACTTTAACGA TGCCATTCTC CGAGACGTCG TCAGTATAGG    1850

AGGAACCGAG GATCAAGTCA CCATTCGATT CGTGGTATAT ACTTCATTCT    1900

TGTGGATGTA TGTGCTCTAG GATACTAACT GGCTTGCGCG TATAGACCGA    1950

TAACCCCGGA CCGTGGTTCC TCCATTGCCA TATCGACTGG CACTTGGAAG    2000

CGGGTCTCGC TATCGTATTT GCAGAGGGAA TTGAAAATAC TGCTGCGTCT    2050

AATCCAACCC CCCGTATGCG GTTTCCCACA CATTCTGAAT CTAAGCAGCT    2100

TACTAATATA CATTTGCAGA GGCTTGGGAT GAGCTTTGCC CGAAGTATAA    2150

CGCGCTCAAC GCACAAAAGA AGGTTGCATC TAAGAAAGGC ACTGCCATCT    2200

AATCCTTGTA ACAAACAAGG AGGGTCTCTT GTACTTTTAT TGGGATTTAT    2250

TTCTTGGGGT TTATTGTTCA ACTTGATTCT ACTATGTTTG GAAGTAGCGA    2300

TTACGAAAGG GGCTTGCGCA TTTATATACC ATCTTTCTTG GCACCACCTG    2350

CAGCTCAATC CTTCAACCAC CTAA                                2374
``` encoding the enzyme laccase A2, having the translated
protein sequence shown in (SEQ ID No. 4)

```
MSSKLLALIT VALVLPLGTD AGIGPVTDLR ITNQDIAPDG FTRPAVLAGG      50

TFPGALITGQ KGDSFQINVI DELTDASMLT QTSIHWHGFF QKGSAWADGP     100

AFVTQCPIVT GNSFLYDFDV PDQPGTFWYH SHLSTQYCDG LRGPFVVYDP    150

KDPNKRLYDI DNDHTVITLA DWYHVLARTV VGVATPDATL INGLGRSPDG    200

PADAELAVIN VKRGKRYRFR LVSISCDPNY IFSIDNHSMT VIEVDGVNTQ    250

SLTVDSIQIF AGQRYSFVLH ANRPENNYWI RAKPNIGTDT TTDNGMNSAI    300

LRYNGAPVAE PQTVQSPSLT PLLEQNLRPL VYTPVPGNPT PGGADIVHTL    350

DLSFDAGRFS INGASFLDPT VPVLLQILSG TQNAQDLLPP GSVIPLELGK    400

VVELVIPAGV VGGPHPFHLH GHNFWVVRSA GTDQYNFNDA ILRDVVSIGG    450

TEDQVTIRFV TDNPGPWFLH CHIDWHLEAG LAIVFAEGIE NTAASNPTPQ    500

AWDELCPKYN ALNAQKKLNP STT                                 523
```

C. Cerrena laccase B1 gene from CBS115.075 strain
(SEQ ID No. 5)

```
ATGTCTCTTC TTCGTAGCTT GACCTCCCTC ATCGTACTAG TCATTGGTGC      50

ATTTGCTGCA ATCGGTCCAG TCACTGACCT ACATATAGTG AACCAGAATC    100

TCGACCCAGA TGGTTTCAAC CGCCCCACTG TACTCGCAGG TGGTACTTTC    150

CCCGGTCCTC TGATTCGTGG TAACAAGGTA CGCTTCATAA CCGCCCTCCG    200

TAGACGTAGG CTTCGGCTGA CATGACCATC ATCTGTAGGG AGATAACTTT    250

AAAATTAATG TGATTGACGA CTTGACAGAG CACAGTATGC TCAAGGCTAC    300

GTCCATCGTA AGTCCCTGAT TAACGTTTCA CCTGGTCATA TCGCTCAACG    350

TCTCGAAGCA CTGGCATGGG TTCTTCCAGA AGGGAACCAA CTGGGCCGAT    400

GGCCCCGCCT TTGTCACCCA ATGTCCTATC ACATCAGGAA ACGCCTTCCT    450

GTATGATTTC AACGTTCCGG ACCAAGCTGG TACTTTCTGG TACCACAGCC    500

ATCTCTCTAC ACAGTATTGT GACGGTCTTC GTGGTGCCTT TGTCGTCTAT    550

GATCCTAATG ATCCCAACAA GCAACTCTAT GATGTTGATA ACGGCAAGTT    600

CCTTGCATAT TTCATTTCTA TCATATCCTC ACCTGTATTG GCACAGAAAG    650

CACCGTGATT ACCTTGGCTG ATTGGTATCA TGCCCTTGCT CAGACTGTCA    700
```

```
CTGGTGTCGC GTGAGTGACA AATGGCCCTC AATTGTTCAC ATATTTTCCT      750
GATTATCATA TGATAGAGTA TCTGATGCAA CGTTGATCAA CGGATTGGGA      800
CGTTCGGCCA CCGGCCCCGC AAATGCCCCT CTGGCGGTCA TCAGTGTCGA      850
GCGGAATAAG AGGTCAGTTC CATAATTATG ATTATTTCCC GCGTTACTTC      900
CTAACAATTA TTTTTGTATC CCTCCACAGA TATCGTTTCC GATTGGTTTC      950
TATTTCTTGC GACCCTAACT TTATTTTCTC AATTGACCAC CACCCAATGA     1000
CCGTAATTGA GATGGACGGT GTTAATACCC AATCTATGAC CGTAGATTCG     1050
ATCCAAATAT TCGCAGGTCA ACGATATTCA TTTGTCGTAG GTTATTATAA     1100
ACTGCCCACC GATCATCTCT CACGTAACTG TTATAGATGC AAGCCAACCA     1150
ACCAGTTGGA AATTATTGGA TCCGCGCTAA ACCTAATGTT GGGAACACAA     1200
CTTTCCTTGG AGGCCTGAAC TCCGCTATAT TACGATATGT GGGAGCCCCT     1250
GACCAAGAAC CGACCACTGA CCAAACACCC AACTCTACAC CGCTCGTTGA     1300
GGCGAACCTA CGACCCCTCG TCTATACTCC TGTGGTATGT TGTTCTCGTT     1350
ACATATACCA AACCTAATAT GAAGACTGAA CGGATCTACT AGCCGGGACA     1400
GCCATTCCCT GGCGGTGCTG ATATCGTCAA GAACTTAGCT TTGGGTTTCG     1450
TACGTGTATT TCACTTCCCT TTTGGCAGTA ACTGAGGTGG AATGTATATA     1500
GAATGCCGGG CGTTTCACAA TCAATGGAGC GTCCCTCACA CCTCCTACAG     1550
TCCCTGTACT ACTCCAGATC CTCAGTGGTA CTCACAATGC ACAGGATCTT     1600
CTCCCAGCAG GAAGCGTGAT CGAACTTGAA CAGAATAAAG TTGTCGAAAT     1650
CGTTTTGCCC GCTGCGGGCG CCGTTGGCGG TCCTCATCCT TTTCACTTAC     1700
ATGGTGTAAG TATCAGACGT CCTCATGCCC ATATTGCTCC GAACCTTACA     1750
CACCTGATTT CAGCACAATT TCTGGGTGGT TCGTAGCGCC GGTCAAACCA     1800
CATACAATTT CAATGATGCT CCTATCCGTG ATGTTGTCAG TATTGGCGGT     1850
GCAAACGATC AAGTCACGAT CCGATTTGTG GTATGTATCT CGTGCCTTGC     1900
ATTCATTCCA CGAGTAATGA TCCTTACACT TCGGGTTCTC AGACCGATAA     1950
CCCTGGCCCA TGGTTCCTTC ACTGTCACAT TGACTGGCAT TTGGAGGCTG     2000
GGTTCGCTGT AGTCTTTGCG GAGGGAATCA ATGGTACTGC AGCTGCTAAT     2050
CCAGTCCCAG GTAAGACTCT CGCTGCTTTG CGTAATATCT ATGAATTTAA     2100
ATCATATCAA TTTGCAGCGG CTTGGAATCA ATTGTGCCCA TTGTATGATG     2150
CCTTGAGCCC AGGTGATACA TGA                                  2173
encoding the enzyme laccase B1, having the translated
protein sequence (SEQ ID No. 6)
MSLLRSLTSL IVLVIGAFAA IGPVTDLHIV NQNLDPDGFN RPTVLAGGTF       50
PGPLIRGNKG DNFKINVIDD LTEHSMLKAT SIHWHGFFQK GTNWADGPAF      100
VTQCPITSGN AFLYDFNVPD QAGTFWYHSH LSTQYCDGLR GAFVVYDPND      150
PNKQLYDVDN GNTVITLADW YHALAQTVTG VAVSDATLIN GLGRSATGPA      200
NAPLAVISVE RNKRYRFRLV SISCDPNFIF SIDHHPMTVI EMDGVNTQSM      250
TVDSIQIFAG QRYSFVMQAN QPVGNYWIRA KPNVGNTTFL GGLNSAILRY      300
VGAPDQEPTT DQTPNSTPLV EANLRPLVYT PVPGQPFPGG ADIVKNLALG      350
FNAGRETING ASLTPPTVPV LLQILSGTHN AQDLLPAGSV IELEQNKVVE      400
IVLPAAGAVG GPHPFHLHGH NFWVVRSAGQ TTYNENDAPI RDVVSIGGAN      450
```

```
DQVTIRFVTD NPGPWFLHCH IDWHLEAGFA VVFAEGINGT AAANPVPAAW    500

NQLCPLYDAL SPGDT                                         515

D. Cerrena laccase B2 gene from CBS154.29 strain
(SEQ ID No. 7)
CACCGCGATG TCTCTTCTTC GTAGCTTGAC CTCCCTCATC GTACTAGCCA     50

CTGGTGCATT TGCTGCAATC GGTCCAGTCA CCGACCTACA TATAGTGAAC    100

CAGAATCTCG CCCCAGATGG TTTAAACCGC CCCACTGTAC TCGCAGGTGG    150

TACTTTCCCC GGTCCTCTGA TTCGTGGTAA CAAGGTACGC TTCATAACCG    200

CCCTCCGTAG ACGTAGGCTT CGGCTGACAT GACCATCATC TGTAGGGAGA    250

TAACTTTAAA ATTAATGTGA TTGACGACTT GACAGAACAC AGTATGCTCA    300

AGGCTACGTC CATTGTAAGT CCCTGATTAA CGTTTCACCT GGTCATATCG    350

CTCAACGTCT CGAAGCACTG GCATGGGTTC TTCCAGAAGG GAACCAACTG    400

GGCCGATGGC CCCGCCTTTG TCACCCAATG TCCTATCACA TCAGGAAACG    450

CCTTCTTGTA TGATTTCAAC GTTCCGGACC AAGCTGGTAC TTTCTGGTAC    500

CACAGCCATC TCTCYACACA GTATTGTGAC GGTCTTCGTG GTGCCTTTGT    550

CGTCTATGAT CCTAATGATC CCAACAAGCA ACTCTATGAT GTTGATAACG    600

GCAAGTCCCT TGCATATTTC AGTTCTATCA TATCCTCACC TGTATTGGCA    650

CAGAAAGCAC CGTGATTACC TTGGCTGATT GGTATCATGC CCTTGCTCAG    700

ACTGTCACTG GTGTCGCGTG AGTGACAAAT GGCCCTTAAT TGTTCACATA    750

TTTTCCTGAT TATCATATGA TAGAGTATCT GATGCAACGT TGATCAACGG    800

ATTGGGACGT TCGGCCACCG GCCCCGCAAA TGCCCCTCTG GCGGTCATCA    850

GTGTCGAGCG GAATAAGAGG TCAGTTCCAT AATTATGATT ATTTCCCGCG    900

TTACTTCCTA ACGATTATTT TTGTATCCCT CCACAGATAT CGTTTCCGAT    950

TGGTTTCTAT TTCTTGCGAC CCTAACTTTA TTTTCTCAAT TGACCACCAC   1000

CCAATGACCG TAATTGAGAT GGACGGTGTT AATACCCAAT CTATGACCGT   1050

AGATTCGATC CAAATATTCG CAGGTCAACG ATATTCATTT GTCGTAGGTT   1100

ATTATAAACT GCCCACCGAT CATCTCTCAC GTAACTGTTA TAGATGCAAG   1150

CCAACCAACC AGTTGGAAAT TATTGGATCC GYGCTAAACC TAATGTTGGG   1200

AACACAACTT TCCTTGGAGG CCTGAACTCC GCTATATTAC GATATGTGGG   1250

AGCCCCTGAC CAAGAACCGA CCACTGACCA AACACCCAAC TCTACACCGC   1300

TCGTCGAGGC GAACCTACGT CCCCTCGTCT ATACTCCTGT GGTATGTTGT   1350

TCTCGTTACA TATACCAAAC CTAATATGAG GACTGAACGG ATCTACTAGC   1400

CGGGACAGCC ATTCCCTGGC GGTGCTGATA TCGTCAAGAA CTTAGCTTTG   1450

GGTTTCGTAC GTGTATTTCA CTTCCCTTTT GGCAGTAACT GAGGTGGAAT   1500

GTATATAGAA TGCCGGGCGT TCACAATCA ATGGAACATC CTTCACACCT    1550

CCTACAGTCC CTGTACTACT CCAGATCCTC AGTGGTACTC ACAATGCACA   1600

GGATCTTCTT CCAGCAGGAA GCGTGATCGA ACTTGAACAG AATAAAGTTG   1650

TCGAAATCGT TCTGCCCGCT GCGGGCGCCG TTGGCGGTCC TCATCCTTTC   1700

CACTTACATG GTGTAAGTAT CAGACGTCCT CATGCCTATA TTGCTCCGAA   1750

CCTTACACAC CTGATTTCAG CACAATTTCT GGGTGGTTCG TAGCGCCGGT   1800

CAAACCACAT ACAATTTCAA TGATGCTCCT ATCCGTGATG TTGTCAGTAT   1850

TGGCGGTGCA AACGATCAAG TCACGATCCG ATTTGTGGTA TGTATCTCGT   1900
```

-continued

```
GCCTTGCATT CATTCCACGA GTAATGATCC TTACACTTCG GGTTCTCAGA    1950
CCGATAACCC TGGCCCATGG TTCCTTCACT GTCACATTGA CTGGCATTTG    2000
GAGGCTGGGT TCGCTGTAGT CTTTGCGGAG GGAATCAATG GCACTGCAGC    2050
TGCTAATCCA GTCCCAGGTA AGACTCTCGC TGCTTTGCGT AATATCTATG    2100
AATTTAAAGC ATATCAATTT GCAGCGGCTT GGAATCAATT GTGCCCGTTG    2150
TATGATGCCT TGAGCCCAGG tGATACATGA TTACTCGTAG CTGTGCTTTC    2200
TTATACATAT TCTATGGGTA TATCGGAGTA GCTGTACTAT AGTATGTACT    2250
ATACTAGGTG GGATATGYTG ATGTTGATTT ATATAATTTT GTTTGAAGAG    2300
TGACTTTATC GACTTGGGAT TTAGCCGAGT ACATACTGAT CTCTCACTAC    2350
AGGCTTGTTT TGTCTTTGGG CGCTTACTCA ACAGTTGACT GTTTTTGCTA    2400
TTACGCATTG AACCGCATTC CGGTCYGACT CGTGTCCTCT ACTGTGACTT    2450
GTATTGGCAT TCTAGCACAT ATGTCTCTTA CCTATAGGAA CAATATGTCT    2500
CAACACTGTT CCAAAACCTG CGTAAACCAA ATATCGTCCA TCAGATCAGA    2550
TCATTAACAG TGCCGCACTA ACCTAATACA CTGGCARGGA CTGTGGAAAT    2600
CCCTATAAAT GACCTCTAGA CCGTGAGGTC ATTGCAAGGT CGCTCTCCTT    2650
GTCAAGATGA CCC                                            2663
``` encoding the enzyme laccase B2, having the translated protein sequence (SEQ ID No. 8)

```
MSLLRSLTSL IVLATGAFAA IGPVTDLHIV NQNLAPDGLN RPTVLAGGTF     50
PGPLIRGNKG DNFKINVIDD LTEHSMLKAT SIHWHGFFQK GTNWADGPAF    100
VTQCPITSGN AFLYDFNVPD QAGTFWYHSH LSTQYCDGLR GAFVVYDPND    150
PNKQLYDVDN GNTVITLADW YHALAQTVTG VAVSDATLIN GLGRSATGPA    200
NAPLAVISVE RNKRYRFRLV SISCDPNFIF SIDHHPMTVI EMDGVNTQSM    250
TVDSIQIFAG QRYSFVMQAN QPVGNYWIRA KPNVGNTTFL GGLNSAILRY    300
VGAPDQEPTT DQTPNSTPLV EANLRPLVYT PVPGQPFPGG ADIVKNLALG    350
FNAGRETING TSFTPPTVPV LLQILSGTHN AQDLLPAGSV IELEQNKVVE    400
IVLPAAGAVG GPHPFHLHGH NFWVVRSAGQ TTYNFNDAPI RDVVSIGGAN    450
DQVTIRFVTD NPGPWFLHCH IDWHLEAGFA VVFAEGINGT AAANPVPAAW    500
NQLCPLYDAL SPGDT                                          515
```

E. Cerrena laccase B3 gene (partial) from ATCC20013 strain (SEQ ID No. 9)

```
GTGGGGGCGG ATCCCTAACT GTTTCGAATC GGCACCGAAG TATGCAGGTG     50
TGACGGAGAT GAGGCGTTTT TTCATCTTCC ACTGCAGTAT AAAATGTCTC    100
AGGTAACGTC CAGCTTTTTG TACCAGAGCT ACCTCCAAAT ACCTTTACTC    150
GCAAAGGTTT CGCGATGTCT CTTCTTCGTA GCTTGACCTC CCTCATCGTA    200
CTAGCCACTG GTGCATTTGC TGCAATCGGT CCAGTCACTG ACCTACATAT    250
AGTGAACCAG AATCTCGCCC AGATGGTTT CAACCGCCCC ACTGTACTCG    300
CAGGTGGTAC TTTCCCCGGT CCTCTGATTC GTGGTAACAA GGTACGCTTC    350
ATAACCGCCC TCCGTAGACG TAGGCTTCGG CTGACATGAC CATCATCTGT    400
AGGGAGATAA CTTTAAAATT AATGTGATTG ACGACTTGAC AGAACACAGT    450
ATGCTCAAGG CCACGTCCAT TGTAAGTCCC TGATTAACGT TTCACCTGGT    500
CATATCGCTC AACGTCTCGA AGCACTGGCA TGGGTTCTTC CAGAAGGGAA    550
```

-continued

```
CCAACTGGGC CGATGGCCCC GCCTTTGTCA CCCAATGTCC TATCACATCA      600

GGAAACTCCT TCCTGTATGA TTTCAACGTT CCGGACCAAG CTGGTACTTT      650

CTGGTACCAC AGCCATCTCT CTACACAGTA TTGTGACGGT CTTCGTGGTG      700

CCTTTGTCGT CTATGATCCT AATGATCCCA ACAAGCAACT CTATGATGTT      750

GATAACGGCA AGTCCCTTGC ATATTTCATT TCTATCATAT CCTCACCTGT      800

ATTGGCACAG AAAGCACCGT GATTACCTTG GCTGATTGGT ATCATGCCCT      850

TGCTCAGACT GTCACTGGTG TCGCGTGAGT GACAAATGGC CCTCAATTGT      900

TCACATATTT TCCTGATTAT CATATGATAG AGTATCTGAT GCAACGTTGA      950

TCAACGGATT GGGACGTTCG GCCACCGGCC CCGCAAATGC CCCTCTGGCG     1000

GTCATCAGTG TCGAGCGGAA TAAGAGGTCA GTTCCATAAT TATGATTATT     1050

TCCCGCGTTA CTTCCTAACA ATTATTCTTG TATCCCTCCA CAGATATCGC     1100

TTCCGATTGG TGTCTATTTC TTGCGACCCT AACTTTATTT TCTCAATTGA     1150

TCACCACCCA ATGACCGTAA TTGAGATGGA CGGTGTTAAT ACCCAATCTA     1200

TGACCGTAGA TTCGATCCAA ATATTCGCAG GTCAACGATA TTCATTTGTC     1250

GTAGGTTATT ATAAACTGCC CACCGATCAT CTCTCACGTA ACTGTTATAG     1300

ATGCAAGCCA ACCAACCRGT TGGAAATTAT TGGATCC                   1337
``` encoding the enzyme laccase B3, having the partial
translated protein sequence (SEQ ID No. 10)

```
MSLLRSLTSL IVLATGAFAA IGPVTDLHIV NQNLAPDGFN RPTVLAGGTF       50

PGPLIRGNKG DNFKINVIDD LTEHSMLKAT SIHWHGFFQK GTNWADGPAF      100

VTQCPITSGN SFLYDFNVPD QAGTFWYHSH LSTQYCDGLR GAFVVYDPND      150

PNKQLYDVDN GKTVITLADW YHALAQTVTG VAVSDATLIN GLGRSATGPA      200

NAPLAVISVE RNKRYRFRLV SISCDPNFIF SIDHHPMTVI EMDGVNTQSM      250

TVDSIQIFAG QRYSFVMQAN QPVGNYWI                             278
```

F. Cerrena laccase C gene (partial) from CBS154.29
strain (SEQ ID No. 11)

```
TGCAATCGGA CCGGTBGCTG ACCTTCACAT TACGGACGAT ACCATTGCCC       50

CCGATGGTTT CTCTCGTCCT GCTGTTCTCG CTGGCGGGGG TTTCCCTGGC      100

CCTCTCATCA CCGGAAACAA GGTAATGCCT AATGGTTGCG TCTTTGTTGG      150

TGCTCTCATT CATCCACGAC ATTTTGTACC AGGGCGACGC CTTTAAACTC      200

AATGTCATCG ATGAACTAAC GGACGCATCC ATGCTGAAGY CGACTTCCAT      250

CGTAAGTCTC GCTGTATTGC TCCTTGAGCC ATTTCATTGA CTATAACTAC      300

AACCAGCACT GGCATGGATT CTTCCAAAAG GGTACTAATT GGGCAGATGG      350

TCCCGCTTTT GTGAACCAAT GCCCCATCAC CACGGGAAAC TCCTTCTTGT      400

ACGACTTCCA GGTTCCTGAT CAAGCTGGTA AGCATGAGAT TACACTAGGA      450

AAGTTTAATT TAATAACTAT TCAATCAGGA ACCTACTGGT ATCATAGTCA      500

TTTGTCTACG CAATACTGTG ATGGTCTCAG AGGTGCATTC GTTGTCTACG      550

ACCCTTCAGA TCCTCACAAG GATCTCTACG ACGTCGACGA CGGTGAGCTT      600

TGCTTTTTTC ATTGGTATCC ATTATCGCTC ACGTGTCATT ACTGCGCCAC      650

AGAAAGTACC GTCATCACTT TGGCTGATTG GTATCATACT TTGGCTCGTC      700

AGATTGTTGG CGTTGCGTGA GTAGTCTTGT ACCGACTGAA ACATATTCCA      750

GTTGCTGACT TCCCCACAGC ATTTCTGATA CTACCTTGAT AAACGGTTTG      800

GGCCGCAATA CCAATGGTCC GGCTGATGCT GCTCTTGCTG TGATCAATGT      850
```

```
TGACGCTGGC AAACGGTGTG TCCAGATTAC TATACTCCCC ATGACGTCTC    900

AATGCTGATG TGTACTACTT CCAGGTACCG TTTCCGTCTT GTTTCCATAT    950

CCTGTGACCC CAATTGGGTA TTCTCGATTG ACAACCATGA CTTTACGGTC   1000

ATTGAAGTCG ATGGTGTTAA CAGTCAACCT CTCAACGTCG ATTCTGTTCA   1050

GATCTTCGCC GGACAACGTT ACTCGTTCGT                         1080
``` encoding the enzyme laccase C, having the partial translated
protein sequence (SEQ ID No. 12)

```
AIGPVADLHI TDDTIAPDGF SRPAVLAGGG FPGPLITGNK GDAFKLNVID     50

ELTDASMLKX TSIHWHGFFQ KGTNWADGPA FVNQCPITTG NSFLYDFQVP    100

DQAGTYWYHS HLSTQYCDGL RGAFVVYDPS DPHKDLYDVD DESIVITLAD    150

WYHTLARQIV GVAISDTTLI NGLGRNTNGP ADAALAVINV DAGKRYRFRL    200

VSISCDPNWV FSIDNHDFTV IEVDGVNSQP LNVDSVQIFA GQRYSF        246
```

G. Cerrena laccase D1 gene from CBS154.29 strain
(SEQ ID No. 13)

```
GATTCTAATA GACCAGGCAT ACCAAGAGAT CTACAGGTTG ACAGACCATT     50

CTTCTAGGCG GCATTTATGC TGTAGCGTCA GAAATTATCT CTCCATTTGT    100

ATCCCACAGG TCCTGTAATA ACACGGAGAC AGTCCAAACT GGGATGCCTT    150

TTTTCTCAAC TATGGGCGCA CATAGTCTGG ACGATGGTAT ATAAGACGAT    200

GGTATGAGAC CCATGAAGTC AGAACACTTT TGCTCTCTGA CATTTCATGG    250

TTCACACTCT CGAGATGGGA TTGAACTCGG CTATTACATC GCTTGCTATC    300

TTAGCTCTGT CAGTCGGAAG CTATGCTGCA ATTGGGCCCG TGGCCGACAT    350

ACACATTGTC AACAAAGACC TTGCTCCAGA TGGCGTACAA CGTCCAACCG    400

TGCTTGCCGG AGGCACTTTT CCTGGGACGT TGATCACCGG TCAGAAAGTA    450

AGGGATATTA GTTTGCGTCA AAGAGCCAAC CAAAACTAAC CGTCCCGTAC    500

TATAGGGTGA CAACTTCCAG CTCAATGTCA TCGATGATCT TACCGACGAT    550

CGGATGTTGA CGCCAACTTC CATTGTGAGC CTATTATTGT ATGATTTATC    600

CGAATAGTTT CGCAGTCTGA TCATTGGATC TCTATCGCTA GCATTGGCAC    650

GGTTTCTTCC AGAAGGGAAC CGCTTGGGCC GACGGTCCCG CCTTCGTAAC    700

TCAGTGCCCT ATAATAGCAG ATAACTCTTT TCTGTATGAC TTCGACGTCC    750

CAGACCAAGC TGGTACTTTC TGGTATCATA GTCATCTATC CACTCAGTAC    800

TGTGACGGTT TACGTGGTGC CTTCGTTGTG TACGATCCTA ACGATCCTCA    850

CAAAGACCTA TACGATGTTG ATGACGGTGG GTTCCAAATA TTTGTTCTGC    900

AGACATTGTA TTGACGGTGT TCATTATAAT TTCAGAGAGC ACCGTGATTA    950

CCCTTGCGGA TTGGTACCAT GTTCTCGCCC AGACCGTTGT CGGCGCTGCG   1000

TGAGTAACAC ATACACGCGC TCCGGCACAC TGATACTAAT TTTTTTTTAT   1050

TGTAGCACTC CTGATTCTAC CTTGATCAAC GGGTTAGGCC GTTCACAGAC   1100

CGGACCCGCT GATGCTGAGC TGGCTGTTAT CAGCGTTGAA CATAACAAAC   1150

GGTATGTCAT CTCTACCCAG TATCTTCTCT CCTGCTCTAA TTCGCTGTTT   1200

CACCATAGAT ACCGTTTCCG TTTGGTTTCG ATTTCGTGCG ACCCCAACTT   1250

TACCTTCTCC GTTGATGGTC ATAATATGAC TGTCATCGAA GTCGATGGTG   1300

TCAACACACG ACCCCTGACC GTTGACTCTA TTCAAATCTT CGCCGGACAG   1350

AGGTATTCCT TTGTCGTAAG TTAATCGATA TATTCTCCTT ATTACCCCTG   1400
```

```
TGTAATTGAT GTCAATAGCT CAATGCTAAC CAACCCGAAG ACAATTACTG    1450

GATCCGTGCT ATGCCAAACA TCGGTAGAAA TACAACAACA CTGGACGGAA    1500

AGAATGCCGC TATCCTTCGA TACAAGAATG CTTCTGTAGA AGAGCCCAAG    1550

ACCGTTGGGG GCCCCGCTCA ATCCCCGTTG AATGAAGCGG ACCTGCGTCC    1600

ACTCGTACCT GCTCCTGTGG TATGTCTTGT CGCGCTGTTC CATCGCTATT    1650

TCATATTAAC GTTTTGTTTT TGTCAAGCCT GGAAACGCTG TTCCAGGTGG    1700

CGCAGACATC AATCACAGGC TTAACTTAAC TTTCGTACGT ACACCTGGTT    1750

GAAACATTAT ATTTCCAGTC TAACCTCTCT TGTAGAGTAA CGGCCTCTTC    1800

AGCATCAACA ACGCCTCCTT CACTaATCCT TCGGTCCCCG CCTTATTACA    1850

AATTCTGAGC GGTGCTCAGA ACGCTCAAGA TTTACTTCCA ACGGGTAGTT    1900

ACATTGGCCT TGAACTAGGC AAGGTTGTGG AGCTCGTTAT ACCTCCTCTG    1950

GCAGTTGGAG GACCGCACCC TTTCCATCTT CATGGCGTAA GCATACCACA    2000

CTCCCGCAGC CAGAATGACG CAAACTAATC ATGATATGCA GCACAATTTC    2050

TGGGTCGTCC GTAGTGCAGG TAGCGATGAG TATAACTTTG ACGATGCTAT    2100

CCTCAGGGAC GTCGTRAGCA TTGGAGCGGG GACTGATGAG GTCACAATCC    2150

GTTTCGTGGT ATGTCTCACC CCTCGCATTT TGAGACGCAA GAGCTGATAT    2200

ATTTTAACAT AGACCGACAA TCCGGGCCCG TGGTTCCTCC ATTGCCATAT    2250

TGATTGGCAT TTGGAGGCAG GCCTTGCCAT CGTCTTCGCT GAGGGCATCA    2300

ATCAGACCGC TGCAGCCAAC CCAACACCCC GTACGTGACA CTGAGGGTTT    2350

CTTTATAGTG CTGGATTACT GAATCGAGAT TTCTCCACAG AAGCATGGGA    2400

TGAGCTTTGC CCCAAATATA ACGGGTTGAG TGCGAGCCAG AAGGTCAAGC    2450

CTAAGAAAGG AACTGCTATT TAAACGTGGT CCTAGACTAC GGGCATATAA    2500

GTATTCGGGT AGCGCGTGTG AGCAATGTTC CGATACACGT AGATTCATCA    2550

CCGGACACGC TGGGACAATT TGTGTATAAT GGCTAGTAAC GTATCTGAGT    2600

TCTGGTGTGT AGTTCAAAGA GACAGCCCTT CCTGAGACAC CCCTTCCTGA    2650

GACAGCCCTT CCTGAGACGT GACCTCCGTA GTCTGCACAC GATACTYCTA    2700

AATACGTATG GCAAGATGAC AAAGAGGAGG ATGTGAGTTA CTACGAACAG    2750

AAATAGTGCC CGGCCTCGGA GAGATGTTCT TGAATATGGG ACTGGGACCA    2800

ACATCCGGA                                                 2809
``` encoding the enzyme laccase D1, having the translated
protein sequence (SEQ ID No. 14)
```
MGLNSAITSL AILALSVGSY AAIGPVADIH IVNKDLAPDG VQRPTVLAGG     50

TFPGTLITGQ KGDNFQLNVI DDLTDDRMLT PTSIHWHGFF QKGTAWADGP    100

AFVTQCPIIA DNSFLYDFDV PDQAGTFWYH SHLSTQYCDG LRGAFVVYDP    150

NDPHKDLYDV DDGGTVITLA DWYHVLAQTV VGAATPDSTL INGLGRSQTG    200

PADAELAVIS VEHNKRYRFR LVSISCDPNF TFSVDGHNMT VIEVDGVNTR    250

PLTVDSIQIF AGQRYSFVLN ANQPEDNYWI RAMPNIGRNT TTLDGKNAAI    300

LRYKNASVEE PKTVGGPAQS PLNEADLRPL VPAPVPGNAV PGGADINHRL    350

NLTFSNGLFS INNASFTNPS VPALLQILSG AQNAQDLLPT GSYIGLELGK    400

VVELVIPPLA VGGPHPFHLH GHNFWVVRSA GSDEYNFDDA ILRDVVSIGA    450

GTDEVTIRFV TDNPGPWFLH CHIDWHLEAG LAIVFAEGIN QTAAANPTPQ    500

AWDELCPKYN GLSASQKVKP KKGTAI                             526
```

H. Cerrena laccase D2 gene from CBS115.075 strain
(SEQ ID No. 15)

```
GATCTGGACG ATGGTATATA AGACGATGGT ATGAGACCCA TGAAGTCTGA    50
ACACTTTTGC TCTCTGACAT TTCATGGTTC ATACTCTCGA GATGGGATTG   100
AACTCGGCTA TTACATCGCT TGCTATCTTA GCTCTGTCAG TCGGAAGCTA   150
TGCTGCAATT GGGCCCGTGG CCGACATACA CATTGTCAAC AAAGACCTTG   200
CTCCAGATGG TGTACAACGT CCAACCGTGC TCGCCGGAGG CACTTTTCCT   250
GGGACGTTGA TCACCGGTCA GAAAGTAAGG AATATTAGTT TGCGTCAAAG   300
AGCCAACCAA AATTAACCGT CCCGTCCCAT AGGGTGACAA CTTCCAGCTC   350
AATGTCATTG ATGATCTTAC CGACGATCGG ATGTTGACAC CAACTTCCAT   400
TGTGAGCCTA TTATTGTATG ATTTATCCGT ATAGTTTCTC AGTCTGATCA   450
TTGGCTCTCT ATCGCTAGCA TTGGCACGGT TCTTCCAGA AGGGAACCGC    500
TTGGGCCGAC GGTCCCGCCT TCGTAACTCA GTGCCCTATA ATAGCAGATA   550
ACTCTTTTCT GTATGACTTC GACGTCCCCG ACCAAGCTGG TACTTTCTGG   600
TATCATAGTC ATCTATCCAC TCAGTACTGT GACGGTTTAC GTGGTGCCTT   650
CGTTGTGTAC GATCCTAACG ATCCTCACAA AGACCTATAC GATGTTGATG   700
ACGGTGGGTT CCAAATACTT GACCAAGAAA CATTATATTG ATAGTATCCA   750
CTCTGATTTT CAGAGAGCAC CGTGATTACC CTTGCGGATT GGTACCATGT   800
TCTCGCCCAG ACCGTTGTCG GCGCTGCGTG AGTAACACAT ACACGCGCTC   850
CGGCACACTG ATACTAATTT TTTATTGTAG CACTCCTGAT TCTACCTTGA   900
TCAACGGGTT AGGCCGTTCA CAGACCGGAC CCGCTGATGC TGAGCTGGCT   950
GTTATCAGCG TTGAACATAA CAAACGGTAT GTCATCTCTA CCCATTATCT  1000
TCTCTCCTGC TTTAATTCGC TGTTTCACCA TAGATACCGA TTCCGTTTGG  1050
TTTCGATTTC GTGCGACCCC AACTTTACCT TCTCCGTTGA TGGTCATAAT  1100
ATGACTGTCA TCGAAGTCGA CGGTGTCAAC ACACGACCCC TGACCGTTGA  1150
CTCTATTCAA ATCTTCGCCG GACAGAGGTA TTCCTTTGTC GTAAGTTAAT  1200
CGATATATTC TCCCTATTAC CCCTGTGTAA TTGATGTCAA CAGCTCAATG  1250
CTAACCAACC CGACGACAAT TACTGGATCC GTGCTATGCC AAACATCGGT  1300
AGAAATACAA CAACACTGGA CGGAAAGAAT GCCGCTATCC TTCGATACAA  1350
GAATGCTTCT GTAGAAGAGC CCAAGACCGT TGGGGGCCCC GCTCAATCCC  1400
CGTTGAATGA AGCGGACCTG CGTCCACTCG TACCTGCTCC TGTGGTATGT  1450
CTTGTCGTGC TGTTCCATCG CTATTTCATA TTAACGTTTT GTTTTTGTCA  1500
AGCCTGGAAA CGCTGTTCCA GGTGGCGCAG ACATCAATCA CAGGCTTAAC  1550
TTAACTTTCG TACGTACACC TGGTTGAAAC ATTATATTTC CAGTCTAACC  1600
TCTTGTAGAG TAACGGCCTT TTCAGCATCA ACAACGCCTC CTTCACTAAT  1650
CCTTCGGTCC CCGCCTTATT ACAAATTCTG AGCGGTGCTC AGAACGCTCA  1700
AGATTTACTT CCAACGGGTA GTTACATTGG CCTTGAACTA GGCAAGGTTG  1750
TGGAGCTCGT TATACCTCCT CTGGCAGTTG GAGGACCGCA CCCTTTCCAT  1800
CTTCATGGCG TAAGCATACC ACACTCCCGC AGCCAGAATG ACGCAAACTA  1850
ATCATGATAT GCAGCACAAT TTCTGGGTCG TCCGTAGTGC AGGTAGCGAT  1900
GAGTATAACT TTGACGATGC TATCCTCAGG GACGTCGTGA GCATTGGAGC  1950
```

```
-continued
GGGGACTGAT GAAGTCACAA TCCGTTTCGT GGTATGTCTC ACCCCTCGCA    2000

TTTTGAGACG CAAGAGCTGA TATATTTTAA CATAGACCGA CAATCCGGGC    2050

CCGTGGTTCC TCCATTGCCA TATTGATTGG CATTTGGAGG CAGGCCTTGC    2100

CATCGTCTTC GCTGAGGGCA TCAATCAGAC CGCTGCAGCC AACCCAACAC    2150

CCCGTACGTG ACACTGAGGG TTTCTTTATA GTGCTGGATT ACTGAATCGA    2200

GATTTCTCCA CAGAAGCATG GGATGAGCTT TGCCCCAAAT ATAACGGGTT    2250

GAGTGCGAGC CAGAAGGTCA AGCCTAAGAA AGGAACTGCT ATTTAAACG     2299
``` encoding the enzyme laccase D2, having the translated protein sequence (SEQ ID No. 16)

```
MGLNSAITSL AILALSVGSY AAIGPVADIH IVNKDLAPDG VQRPTVLAGG      50

TFPGTLITGQ KGDNFQLNVI DDLTDDRMLT PTSIHWHGFF QKGTAWADGP     100

AFVTQCPIIA DNSFLYDFDV PDQAGTFWYH SHLSTQYCDG LRGAFVVYDP    150

NDPHKDLYDV DDGGTVITLA DWYHVLAQTV VGAATPDSTL INGLRSQTG     200

PADAELAVIS VEHNKRYRFR LVSISCDPNF TFSVDGHNMT VIEVDGVNTR    250

PLTVDSIQIF AGQRYSFVLN ANQPDDNYWI RAMPNIGRNT TTLDGKNAAI    300

LRYKNASVEE PKTVGGPAQS PLNEADLRPL VPAPVPGNAV PGGADINHRL    350

NLTFSNGLFS INNASFTNPS VPALLQILSG AQNAQDLLPT GSYIGLELGK    400

VVELVIPPLA VGGPHPFHLH GHNFWVVRSA GSDEYNFDDA ILRDVVSIGA    450

GTDEVTIRFV TDNPGPWFLH CHIDWHLEAG LAIVFAEGIN QTAAANPTPQ    500

AWDELCPKYN GLSASQKVKP KKGTAI                              526
```

I. *Cerrena* laccase E gene (partial) from CBS154.29 strain (SEQ ID No. 17)

```
TGCAATCGGA CCGGTGGCCG ACCTCAAGAT CGTAAACCGA GACATTGCAC      50

CTGACGGTTT TATTCGTCCC GCCGTTCTCG CTGGAGGGTC GTTCCCTGGT    100

CCTCTCATTA CAGGGCAGAA AGTACGTTAC GCTATCTCGG TGCTTTGGCT    150

TAATTAAACT ATTTGACTTT GTGTTCTCTT AGGGGAACGA GTTCAAAATC    200

AATGTAGTCA ATCAACTGAC CGATGGTTCT ATGTTAAAAT CCACCTCAAT    250

CGTAAGCAGA ATGAGCCCTT TGCATCTCGT TTTATTGTTA ATGCGCCCAC    300

TATAGCATTG GCATGGATTC TTCCAGAAGG GAACAAACTG GGCAGACGGT    350

CCTGCGTTCG TGAACCAATG TCCAATCGCC ACGAACAATT CGTTCTTGTA    400

TCAGTTTACC TCACAGGAAC AGCCAGGTGA GTATGAGATG GAGTTCATCC    450

GAGCATGAAC TGATTTATTT GGAACCTAGG CACATTTTGG TACCATAGTC    500

ATCTTTCCAC ACAATACTGC GATGGTTTGC GAGGGCCACT CGTGGTGTAT    550

GACCCACAAG ACCCGCATGC TGTTCTCTAC GACGTCGACG ATGGTTCGTA    600

CTTCGCATAT CCACGCTCGC TTTCATACAA TGTAAACTTT GTTCCTCCAG    650

AAAGTACAAT CATCACGCTC GCGGATTGGT ATCATACCTT GGCTCGGCAA    700

GTGAAAGGCC CAGCGTAAGG CACTTTAGTG TTTCCTCATA GTCCAAGAAA    750

TTCTAACACG CCTTCTTCAT CAGGGTTCCT GGTACGACCT TGATCAACGG    800

GTTGGGGCGT CACAACAATG GTCCTCTAGA TGCTGAACTA GCGGTGATCA    850

GTGTTCAAGC CGGCAAACGG CAAGTTCAAT TCACACTTTT CACTCTGTAC    900

CTTCTTCCTG ACATTCTTTT CTTGTAGTTA CCGCTTCCGC CTGATTTCAA    950

TTTCATGCGA TCCCAACTAC GTATTCTCCA TTGATGGCCA TGATATGACT    1000

GTCATCGAAG TGGATAGTGT TAACAGTCAA CCTCTCAAGG TAGATTCTAT    1050
```

```
CCAAATATTT GCAGGTCAGA GATATTCGTT CGTGGTGAGT CAGATCAGGG    1100

CATATCCTTT TGTCGATACG TCATTGACCA TATAATGCTA CAAGCTGAAT    1150

GCCAACCAAC CAG                                           1163 encoding the enzyme laccase E, having the partial translated
protein sequence (SEQ ID No. 18)
AIGPVADLKI VNRDIAPDGF IRPAVLAGGS FPGPLITGQK GNEFKINVVN      50

QLTDGSMLKS TSIHWHGFFQ KGTNWADGPA FVNQCPIATN NSFLYQFTSQ     100

EQPGTFWYHS HLSTQYCDGL RGPLVVYDPQ DPHAVLYDVD DESTIITLAD     150

WYHTLARQVK GPAVPGTTLI NGLGRHNNGP LDAELAVISV QAGKRQVQFT     200

LFTLYRFRLI SISCDPNYVF SIDGHDMTVI EVDSVNSQPL KVDSIQIFAG     250

QRYSFVLNAN QP                                             262
```

The term "% identity" herein and refers to the level of nucleic acid or amino acid sequence identity between the nucleic acid sequence that encodes a laccase described herein or the laccase amino acid sequence, when aligned using a sequence alignment program.

For example, as used herein, 80% sequence identity is determined by an algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for a laccase, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at www.ncbi.nlm.nih.gov/BLAST. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

An alignment of selected sequences in order to determine "% identity" between two or more sequences, may be performed using, for example, the CLUSTAL-W program in MacVector version 6.5, operated with default parameters, including an open gap penalty of 10.0, an extended gap penalty of 0.1, and a BLOSUM 30 similarity matrix.

II. Mediators

In an embodiment, the enzymatic oxidation system further comprises one or more chemical mediator agents which enhance the activity of the laccase enzyme. The term "chemical mediator" (or "mediator" may be used interchangeably herein) is defined herein as a chemical compound which acts as a redox mediator to effectively shuttle electrons between the enzyme exhibiting oxidase activity and the dye. Chemical mediators are also known as enhancers and accelerators in the art.

The chemical mediator may be a phenolic compound, for example, methyl syringate, and related compounds, as described in WO 95/01426 and 96/12845. The chemical mediator may also be an N-hydroxy compound, an N-oxime compound, or an N-oxide compound, for example, N-hydroxybenzotriazole, violuric acid, or N-hydroxyacetanilide. The chemical mediator may also be a phenoxazine/phenothiazine compound, for example, phenothiazine-10-propionate. The chemical mediator may further be 2,2'-azinobis-(3-ethylbenzothiazoline-6-sulfonic acid) (ABTS). Other chemical mediators are well known in the art. For example, the compounds disclosed in WO 95/01426 are known to enhance the activity of a laccase. In particular embodiments, the mediator may be acetosyringone, methyl syringate, ethyl syringate, propyl syringate, butyl syringate, hexyl syringate, or octyl syringate.

Preferably, the mediator is 4-cyano-2,6-dimethoxyphenol, 4-carboxamido-2,6-dimethoxyphenol or an N-substituted derivative thereof such as, for example, 4-(N-methyl carboxamido)-2,6-dimethoxyphenol, 4-[N-(2-hydroxyethyl) carboxamido]-2,6-dimethoxyphenol, or 4-(N,N-dimethyl carboxamido)-2,6-dimethoxyphenol.

The mediator used in the present invention may be described by the following formula:

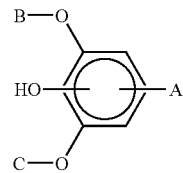

in which formula A is a group such as —R, -D, —CH=CH-D, —CH=CH—CH=CH-D, —CH=N-D, —N=N-D, or —N=CH-D, in which D is selected from the group consisting of —CO-E, —SO$_2$-E, —CN, —NXY, and —N$^+$XYZ, in which E may be —H, —OH, —R, —OR, or —NXY, and X and Y and Z may be identical or different and selected from —H, —OH, —OR and —R; R being a $C_1$-$C_{16}$ alkyl, preferably a $C_1$-$C_8$ alkyl, which alkyl may be saturated or unsaturated, branched or unbranched and optionally substituted with a carboxy, sulfo or amino group; and B and C may be the same or different and selected from $C_mH_{2m+1}$; $1 \leq m \leq 5$.

In an embodiment A in the above mentioned formula is —CN or —CO-E, in which E may be —H, —OH, —R, —OR, or —NXY, where X and Y may be identical or different and selected from —H, —OH, —OR and —R, R being a $C_1$-$C_{16}$ alkyl, preferably a $C_1$-$C_8$ alkyl, which alkyl may be saturated or unsaturated, branched or unbranched and optionally substituted with a carboxy, sulfo or amino group; and B and C may be the same or different and selected from $C_m H_{2m+1}$; $1 \leq m \leq 5$.

In the above mentioned formula A may be placed meta to the hydroxy group instead of being placed in the para-position as shown.

In particular embodiments, the mediator may be acetosyringone, methylsyringate, ethylsyringate, propylsyringate, butylsyringate, hexylsyringate, or octylsyringate. Preferably, the mediator is 4-cyano-2,6-dimethoxyphenol, 4-carboxamido-2,6-dimethoxyphenol or a N-substituted derivative thereof such as 4-(N-methyl carboxamido)-2,6-dimethoxyphenol, 4-[N-(2-hydroxyethyl)carboxamido]-2,6-dimethoxyphenol, or 4-(N,N-dimethyl carboxamido)-2,6-dimethoxyphenol.

The mediator of the invention may be present in concentrations of from 0.005-1000 μmole per g denim, preferably 0.05-500 μmole per g denim, more preferably 0.5-100 μmole per g denim.

The mediators may be prepared by methods known to the skilled artisan, such as those disclosed in WO 97/11217, WO 96/12845 and U.S. Pat. No. 5,752,980.

III. Utility

Industrial applications of laccases include bleaching of pulp and paper and textile bleaching, for example, of indigo-dyed denim fabrics. Laccases have also been found to be useful for hair dyeing (see, e.g., WO 95/33836 and WO 95/33837). European Patent No. 0504005 discloses that laccases can be used for dyeing wool.

The laccases described herein find use in the dyeing and bleaching of textiles, fibers, yarns and the like. The laccases also find use in the treatment of waste water, the delignification of pulp, the depolymerization of high molecular weight aggregates, deinking waste paper, the polymerization of aromatic compounds, radical mediated polymerization and cross-linking reactions (e.g., paints, coatings, biomaterials), and the activation of dyes and to couple organic compounds. The laccases may be used in a cleaning composition or component thereof, or in a detergent.

As described herein, the laccases are capable of oxidizing a wide variety of colored compounds having different chemical structures, using oxygen as the electron acceptor. Accordingly, the laccases presented herein can be used in applications where it is desirable to modify the color associated with colored compounds, such as in cleaning, e.g., for removing the food stains on fabric. In certain situations, a mediator or enhancer can be used to obtain desirable effects.

The laccases presented herein can be used in the field of textiles. For example, the laccases described herein can be used in the treatment, processing, finishing, polishing, or production of fibers, or other fabrics or articles of manufacture. The enzymes herein can be useful, for example, in denim treatment (bleaching work-up processes); in de-coloring indigo waste; in fabric dyeing; in textile bleaching processes; in fiber modification; in achieving enhanced fiber or fabric properties; etc.

The laccases described herein can be used in the leather industry. For example, the laccases can be used in the processing of animal hides including but not limited to de-hairing, liming, bating and/or tanning of hides.

Also disclosed herein is a process for the removal of lignin from lignocellulose-containing material, the bleaching of lignocellulose-containing material (i.e. the enzymatic de-inking of recycled paper) and/or the treatment of waste water arising from the manufacture of paper or cellulose. The process uses laccase enzymes obtained from *Cerrena* sp., at the same time adding or metering in non-aromatic redox agents plus phenolic and/or non-phenolic aromatic redox compounds, the phenolic and non-phenolic units of the lignin either being oxidized directly by the action of these phenolic and/or non-phenolic aromatic compounds, or the lignin being oxidized by other phenolic and/or non-phenolic compounds produced by the oxidizing action of these compounds.

The laccases described herein can be used in the field of pulp and paper. For example, the laccases can be used in the manufacture of paper pulps and fluff pulps from raw materials such as wood, bamboo, and cereal rice straw; the manufacture of paper and boards for printing and writing, packaging, sanitary and other technical uses; recycling of cellulose fiber for the purpose of making paper and boards; and the treatment of waste products generated by and treated at pulp or paper mills and other facilities specifically dedicated to the manufacture of paper, pulp, or fluff. The enzymes presented herein can be useful, for example, in wood processing; in pulp bleaching; in wood fiber modification; in bio-glue (lignin activation) for MDF manufacturing; for enhanced paper properties; in ink removal; in paper dyeing; in adhesives (e.g. lignin based glue for particle- or fiber boards); etc.

The laccases described herein can be used in the field of feed. For example, the laccases presented herein can be used as a feed additive alone or as part of a feed additive with the aim to increase the nutritional value of feed for any kind of animals such as chicken, cows, pigs, fish and pets; and/or as a processing aid to process plant materials and food industry by products with the aim to produce materials/products suitable as feed raw materials.

The laccases described herein can be used in the field of contact lens cleaning. For example, the laccases can be used in the cleaning, storage, disinfecting, and/or preservation of contact lens.

The laccases described herein can be used in the field of starch. For example, the laccases can be used in the processing of a substrate including starch and/or grain to glucose (dextrose) syrup, fructose syrup or any other syrup, alcohol (potable or fuel) or sugar. Such starch processing may include processing steps such as liquefaction, saccharification, isomerization, and de-branching of a substrate.

The laccases described herein can be used in the field of food. For example, the laccases can be used in the preparation, processing, or as an active ingredient in foods such as yellow fat, tea based beverages, culinary products, bakery, and frozen foods for human consumption. The laccases can be used, for example, as a bread improver, in food preservation, as an oxygen scavenger, etc.

The laccases described herein can be used in the field of personal care. For example, the laccases can be used in the preparation of personal products for humans such as fragrances, and products for skin care, hair care, oral hygiene, personal washing and deodorant and/or antiperspirants, for humans. The enzymes presented herein can be useful, for example, in hair dyeing and/or bleaching, nails dyeing and/or bleaching; skin dyeing and/or bleaching; surface modification (e.g., as coupling reagent); as an anti-microbial agent; in odor removal; teeth whitening; etc.

The laccases described herein can be used in the field of cleaning. For example, the laccases can be used in the cleaning, treatment or care of laundry items such as clothing or fabric; in the cleaning of household hard surfaces; in dishcare, including machine dishwashing applications; and in soap bars and liquids and/or synthetic surfactant bars and liquids. The enzymes presented herein can be useful, for example, in stain removal/de-colorization, and/or in the removal of odors, and/or in sanitization, etc.

The laccases described herein can be used in the field of waste-water treatment. For example, the laccases can be used in decolorization of colored compounds; in detoxification of phenolic components; for anti-microbial activity (e.g., in water recycling); in bio-remediation; etc.

The laccases described herein can be used in the field of bio-materials. For example, the laccases can be used as bio-catalysts for various organic reactions; and/or in connection with biopolymers; in connection with packaging; in connection with adhesives; in surface modification (activation and coupling agent); in production of primary alcohols; in connection with biosensors and/or organic syntheses; etc.

The laccases described herein can be used in the field of anti-microbials. For example, the laccases can be used as an anti-microbial agent in cleaning compositions, or for reducing or eliminating the microbial load of various foods (e.g., meats) or feed.

The laccase mediators can be used as sanitization and antimicrobial agents (e.g., wood protection, detergents). The mediators may be used independently of the enzymes or in conjunction with the enzymes.

As used herein, "cleaning compositions" and "cleaning formulations" refer to compositions that find use in the removal of undesired compounds from items to be cleaned, such as fabric, etc. The term encompasses any materials/compounds selected for the particular type of cleaning composition desired and the form of the product (e.g., liquid, gel, granule, or spray composition), as long as the composition is compatible with the laccase and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning and/or bleaching any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the presently contemplated compositions be limited to any particular detergent formulation or composition. Indeed, it is intended that in addition to laccase, the term encompasses detergents that contain surfactants, transferase(s), hydrolytic enzymes, builders, bleaching agents, bleach activators, bluing agents and fluorescent dyes, caking inhibitors, masking agents, enzyme activators, antioxidants, and solubilizers.

As used herein the term "hard surface cleaning composition," refers to detergent compositions for cleaning hard surfaces such as floors, walls, tile, stainless steel vessels (e.g., fermentation tanks), bath and kitchen fixtures, and the like. Such compositions are provided in any form, including but not limited to solids, liquids, emulsions, etc.

EXAMPLES

Example 1

Amino Acid Sequence Analysis of *Cerrena unicolor* Laccase

Four Peptide sequences were obtained using a commercially available laccase: AIGPVADLHI (SEQ ID No. 19), MLTPTSI (SEQ ID No. 20), TVGGPA (SEQ ID No. 21) and YSFVLNANQP (SEQ ID No. 22). The commercially available laccase was purified. N-terminal sequencing resulted in SEQ ID No. 19. Proteolytic digestion with trypsin of the purified sample was performed. Fragments were separated by gel electrophoresis with 3 bands selected and collected manually. Peptide sequencing was performed for each band and resulted in SEQ ID Nos. 20, 21 and 22.

Example 2 a. Cloning of *Cerrena unicolor* Laccase A Gene from ATCC20013 Strain

To clone the laccase A gene from ATCC 20013 strain, two primers were designed and obtained from Invitrogen: TTCG-CAGGTCAACGATATTC (SEQ ID No. 35) based on DNA sequence of the laccase B gene obtained from ATCC20013 strain (see example 3a) and GTTAGGTGGTTGAAG-GATTG (SEQ ID No. 36) based on laccase A gene obtained from CBS115.075 strain (see example 2c). The primers were used in a highT PCR reaction containing genomic DNA obtained from ATCC 20013 strain as template (see example 3). The PCR fragment was purified using a QIAquick spin column from Qiagen and cloned into pTOPO plasmid using TOPO cloning kit (Invitrogen). Twenty-two clones were amplified using Ready-To-Go PCR beads (GE Healthcare) and three PCR fragments (2-1, 2-3 and 2-6) were sequenced. 1316 bps DNA sequence of the laccase A gene from ATCC20013 is listed as SEQ ID No 37.

b. Cloning of *Cerrena unicolor* Laccase A Gene from CBS154.29 Strain

To clone the laccase A gene from CBS154.29 strain, two primer was designed and obtained from Invitrogen: CAC-CAGCATGAGCTCAAAGCTAC (SEQ ID No. 45) based on laccase A gene obtained from CBS115.075 strain (see example 2c) and primer of the SEQ ID No. 36. The primers were used in a Herculase PCR reaction containing genomic DNA template obtained from CBS154.29 strain, dNTPs, primer and 4% DMSO in 1× buffer. The PCR mixture was heated to 98° C. for 4 minutes to denature the DNA template. Herculase® II enzyme (Stratagene) was added to the tube and PCR reaction was performed in 30 cycles of 98° C. for 30 seconds, 50° C. for 30 seconds and 72° C. for 2 minute. The final extension at 72° C. was done for 5 minutes and the reaction was chilled to 4° C. The PCR fragment was purified using the QIAquick spin column and cloned into pENTR/D-TOPO vector (Invitrogen). Fifteen clones were amplified using Ready-To-Go PCR beads and plasmids were isolated from two clones (pENTR15-24 and pENTR15-30) and the DNA templates were sequenced. 2374 bps DNA sequence of the laccase A gene from CBS154.29 was obtained. The DNA sequence is listed as SEQ ID No. 3 and the translated protein sequence is listed as SEQ ID No. 4.

c. Cloning of *Cerrena unicolor* Laccase A Gene from CBS115.075 Strain

The primer CAATCTATGACCGTAGATTC (SEQ ID No. 39) based on the laccase B gene from ATCC20013 strain (see example 3a) and primer NNNNNNNNNNCGATCG (SEQ ID No. 38) where N represents a mixture of all four nucleotides (A, T, C and G) were used in lowT PCR reaction (see example 3a). Genomic DNA was extracted from *Cerrena unicolor* strain (CBS115.075) and was used as template in the first round of lowT PCR reaction. The PCR fragments were purified with a QIAquick spin column and used as template in the second round of lowT PCR reaction with primers of SEQ ID No. 35 based on the laccase B gene from ATCC20013 strain (see example 3a) and primer of the SEQ ID No. 38. The PCR fragments were cloned into pTOPO plasmid using TOPO cloning kit. Sixteen clones were amplified using Ready-To-Go PCR beads and three cloned PCR fragments (B2#1, B2#4 and B2#11) were sequenced.

To clone the 3' end of laccase A gene, the primer ACCGTGGTTCCTCCATTGCC (SEQ ID No. 40) and primer of SEQ ID No. 31 were used in the lowT PCR reaction with the genomic DNA extracted from *Cerrena unicolor* strain (CBS115.075) as template in the first round of lowT PCR reaction. The PCR fragments were purified with a QIAquick spin column and used as template in the second round of lowT PCR reaction with primers GACTGGCACTTGGAAGCGGG (SEQ ID No. 41) and primer of SEQ ID No. 31. The PCR fragments were cloned into pTOPO plasmid using TOPO cloning kit. Twenty-two clones were amplified using Ready-To-Go PCR beads and one cloned PCR fragment (D2#2) was sequenced.

To clone the 5' end of the laccase A gene, a primer, GGACCAAGCTGGTACTTTC (SEQ ID No. 42), was designed based on the laccase B gene sequence. It was used to amplify a DNA fragment with primer of SEQ ID No. 36. The genomic DNA extracted from *Cerrena unicolor* strain (CBS115.075) was used as the PCR template. The 1.7 kb PCR fragment was obtained, purified with a QIAquick spin column and cloned into pTOPO plasmid using TOPO cloning kit. Twenty-two clones were analyzed using Ready-To-Go PCR beads. Plasmid DNA from clone (C5#20) was sequenced. To further clone the 5' of laccase A gene, the primer CGTGGTACCAGTCTGCCAGGG (SEQ ID No. 43) and primer of SEQ ID No. 31 were used in the lowT PCR reaction with the genomic DNA extracted from *Cerrena unicolor* CBS115.075 strain as template. From the first round of lowT PCR reaction, the PCR fragment was purified with a QIAquick spin column and used as template in the second round of lowT PCR reaction with primers GGCAGCATCAGTCACGGTCAG (SEQ ID No. 44) and primer of SEQ ID No. 31. The PCR fragment (a3) was amplified again and used as template in a third round of lowT PCR reaction with primers GGCAGCATCAGTCACGGTCAG (SEQ ID No. 44) and primer of SEQ ID No. 31. The PCT fragment (a3-2) was cloned into pTOPO plasmid using TOPO cloning kit. Eleven clones were amplified using Ready-To-Go PCR beads and two cloned PCR fragments (a3-2#10 and a3-2#11) were sequenced. The DNA sequence of the laccase A gene from CBS115.075 strain including the sequence of 5' and 3' of the coding region is listed as SEQ ID No. 1 and the translated protein sequence is listed as SEQ ID No. 2.

Example 3 a. Cloning and Sequencing of the *Cerrena unicolor* Laccase B Gene from ATCC20013 Strain To clone the DNA fragment encoding the Cerrena laccase gene, four degenerated primers were designed based on the peptide sequence AIGPVADLHI (SEQ ID No. 19) and obtained from Invitrogen. They are named as

```
primerA
GCAATCGGACCNGTNGCAGA;      (SEQ ID No. 23)

primerB
GCAATCGGACCNGTNGCTGA;      (SEQ ID No. 24)

primerC
GCAATCGGACCNGTNGCGGA       (SEQ ID No. 25)
and primerD
GCAATCGGACCNGTNGCCGA.      (SEQ ID No. 26)
```

Two degenerated primers were designed based on the peptide sequence YSFVLNANQP (SEQ ID No. 22) and obtained from Invitrogen. They are named as

```
primerE
GGTTGATTTGCATTNAGNAC       (SEQ ID No. 27)
and primerF
GGTTGATTTGCGTTNAGNAC       (SEQ ID No. 28)
``` where N represents a mixture of all four nucleotides (A, T, C and G). The genomic DNA was extracted from ATCC20013 strain and used as template in the lowT PCR reaction contain following combination of primers: PCR reaction 1 contains no DNA and no primer; PCR reaction 2 contains primerA and primerE; PCR reaction 3 contains primerB and primerE; PCR reaction 4 contains primerC and primerE; PCR reaction 5 contains primerD and primerE; PCR reaction 6 contains primerA and primerF; PCR reaction 7 contains primerB and primerF; PCR reaction 8 contains primerC and primerF and PCR reaction 9 contains primerD and primerF. The PCR reaction mixture contained DNA template, primers, 1× buffer, 0.2 mM dNTP and 1 unit of Taq DNA polymerase. The PCR reaction was performed in 30 cycles of 95° C. for 1 minute, 45° C. for 1 minute and 68° C. for 1 minute. The final extension at 72° C. was done for 7 minutes and the reaction was chilled to 4° C. The PCR fragments from reaction 4, 5 and 8 were cut out of a 1.2% agarose gel and pooled. The PCR fragments were extracted from gel with a Qiagen spin column and cloned into pTOPO plasmid using TOPO cloning kit. Thirty-two cloned PCR fragments were selected and sequenced using Ready-To-Go PCR beads and DNA sequence of clone #A30 was identified as laccase B gene.

To clone the 5' end of laccase gene, a primer was designed and obtained from Invitrogen: GGACGTGGCCTTGAGCATAC (SEQ ID No. 29). It was used in first round of lowT PCR reaction with a degenerated oligo NNNNNNNNNNGGATCC (SEQ ID No. 31) where N represents a mixture of all four nucleotides (A, T, C and G). The PCR product was purified using a QIAquick spin column and used as template in a second lowT PCR reaction containing a primer TCTGTCAAGTCGTCAATCAC (SEQ ID No. 30) and primer of SEQ ID No. 31. The PCR fragment was purified using a QIAquick spin column and diluted 1:10 and 1:100 and used as template in the first round of highT PCR reaction performed in 30 cycles of 95° C. for 1 minute, 50° C. for 1 minute and 72°

C. for 1 minute with two primers (SEQ ID No. 30 and SEQ ID No. 31). The final extension at 72° C. was done for 7 minutes and the reaction was chilled to 4° C. The PCR fragment was purified with a QIAquick spin column and used in the second round of highT PCR reaction with primers of TTACCAC-GAATCAGAGGACC (SEQ ID No. 32) and SEQ ID No. 31. The PCR fragment (D13) was sequenced.

To clone the 3' end of the laccase B gene, a primer was designed and obtained from Invitrogen: CCTCACCTGTAT-TGGCACAG (SEQ ID No. 33) and used with primer of SEQ ID No. 31 in a first round of lowT PCR reaction. The PCR fragment was purified in a QIAquick spin column and used as template in second round of lowT PCR reaction with primer TTGGTATCATGCCCTTGCTC (SEQ ID No. 34) and primer of SEQ ID No. 31. The PCR fragment was cloned into a pTOPO plasmid using TOPO cloning kit. Sixteen clones were amplified using Ready-To-Go PCR beads and four cloned PCR fragments (C3, C4, C5 and C7) were sequenced.

1337 bps DNA fragment was obtained. The DNA sequence is listed as SEQ ID No. 9 and translated protein sequence is listed as SEQ ID No. 10.

b. Cloning of *Cerrena unicolor* Laccase B Gene from CBS154.29 Strain

Two primers were designed and obtained from Invitrogen:

```
CACCGCGATGTCTCTTCTTCGTAG    (SEQ ID No. 46)
and

TGRAGRTGGAASGGATGWGGTCC     (SEQ ID No. 47)
``` where R represent mixture of nucleotides A and G, S represent mixture of nucleotides C and G, and W represent mixture of nucleotides A and T. The two primers were used in the highT PCR reaction. The PCR fragment (A3) was purified using a QIAquick spin column. The PCR fragment was cloned into pTOPO plasmid using TOPO cloning kit. Sixteen clones were amplified using Ready-To-Go PCR beads and two PCR fragments (A3#1 and A3#5) were sequenced.

To clone the 3' end of the laccase B gene from CBS154.29 strain, a primer was designed and obtained from Invitrogen: GTCCCTGTACTACTCCAGATCC (SEQ ID No. 48) and used with a primer having SEQ ID No. 31 in first round of lowT PCR reaction. The PCR fragment was purified in a QIAquick spin column and used as template in second round of lowT PCR reaction with primer CCAGCAGGAAGCGT-GATCGAAC (SEQ ID No. 49) and primer of SEQ ID No. 31. The PCR fragment was cloned into pTOPO plasmid using TOPO cloning kit. Sixteen clones were amplified using Ready-To-Go PCR beads and three PCR fragments (7#6, 7#7 and 7#8) were sequenced. 2663 bps of the laccase B DNA sequence of the CBS154.29 strain is listed as SEQ ID No. 7 and translated protein sequence is listed as SEQ ID No. 8.

c. Cloning of *Cerrena unicolor* Laccase B Gene from CBS115.075 Strain

A primer was designed and obtained from Invitrogen: GTAATCATGTATCACCTGGGCTCAAGG (SEQ ID No. 50). The primer was used in the Herculase PCR reaction (see Example 2b) with primer of SEQ ID No. 46. The PCR fragment was purified using a QIAquick spin column. The PCR fragment was cloned into pTOPO plasmid using TOPO cloning kit. Seventeen clones were analyzed using Ready-To-Go PCR beads and the PCR fragments from four clones (#1, #2, #4 and #5) were sequenced. The plasmid DNA was prepared from two clones (pENTR-laccaseB CBS115075#1 and pENTR-laccaseB CBS115075#3) and both plasmids were sequenced. 2173 bps of the laccase B DNA sequence of the CBS115.075 strain is listed as SEQ ID No. 5 and translated protein sequence is listed as SEQ ID No. 6.

Example 4

Cloning of the *Cerrena unicolor* Laccase C Gene from CBS154.29 Strain

A primer ACGAACGAGTANCGTTGNCC (SEQ ID No. 51), where N represents a mixture of all four nucleotides (i.e., A, T, C and G), was designed based on the translated peptide sequence GQRYSFV (SEQ ID No. 52). This peptide is conserved between the laccase A gene and the laccase B gene (see Examples 2 and 3). The primer was obtained from Invitrogen and was used in the lowT reaction with primer of the SEQ ID No. 24. The PCR fragment was purified using a QIAquick spin column. The PCR fragment was cloned into pTOPO plasmid using TOPO cloning kit. Thirty-three clones were analyzed using Ready-To-Go PCR beads and the PCR fragments from four clones (#12, #5a, #19a and #21a) were sequenced. 1080 bps of the laccase C gene sequence from the CBS154.29 strain is listed as SEQ ID No. 11 and translated protein sequence is listed as SEQ ID No. 12.

Example 5 a. Cloning of *Cerrena unicolor* Laccase D Gene from CBS115.075 Strain

To clone the 5' end of the laccase D gene from CBS115.075 strain, a primer was designed based on laccase D gene from CBS154.29 strain (see Example 5b) (AACACGGAGA-CAGTCCAAAC, SEQ ID No. 62). It was used in the highT PCR reaction with primer of SEQ ID No. 56. The PCR fragment was purified using a QIAquick spin column and sequenced.

To clone the laccase D gene from CBS115.075 strain, two primers (CACCTCTCGAGATGGGATTGAAC, SEQ ID No. 63 and CGTTTAAATAGCAGTTCCTTTC, SEQ ID No. 64) were designed based on the laccase D gene from CBS154.29 strain (see example 5b). The primers were used in a Herculase PCR reaction (see example 2b) with DNA template of the genomic DNA from CBS115.075 strain. The PCR fragment was purified using the QIAquick spin column and cloned into pENTR/D-TOPO vector. Sixteen clones were amplified using Ready-To-Go PCR beads and the PCR fragments generated from four clones were sequenced. The plasmids were isolated from clone #2 (pENTRE-laccaseD#2) and it was sequenced. 2809 bps DNA sequence of the laccase D gene from CBS115.075 was obtained. The DNA sequence is listed as SEQ ID No. 15 and the translated protein sequence is listed as SEQ ID No. 16.

b. Cloning of *Cerrena unicolor* Laccase D Gene from CBS154.29 Strain

A primer, CTGGTTGGTTNGCATTNAG (SEQ ID No. 53), was designed based on the peptide sequence LNANQP (SEQ ID No. 54). The primer was obtained from Invitrogen and used in the lowT PCR reaction with primer of the SEQ ID No. 26. The PCR fragment was purified using a QIAquick spin column and was cloned into pTOPO plasmid using TOPO cloning kit. Eighteen clones were analyzed using Ready-To-Go PCR beads and PCR fragment from a clone was sequenced.

To clone the 3' end of the laccase D gene, a primer (CA-CACGACCCCTGACCGTTG, SEQ ID No. 55) was designed. The primer was used in the lowT PCR reaction with primer of the SEQ ID No. 31. The PCR fragment was purified using a QIAquick spin column and was cloned into pTOPO plasmid using TOPO cloning kit. Twenty-four clones were analyzed using Ready-To-Go PCR beads and PCR fragment(s) from a clone were sequenced.

To clone more of the 3' and the 5' ends of the laccase D gene, inverse PCR was used. 0.4 ug of the genomic DNA from the Cerrena CBS154.29 strain was digested with EcoRV restriction enzyme at 37° C. for 1.5 hours. Digested genomic DNA fragments were precipitated with ethanol. The linear DNA fragments were ligated with T4 DNA ligase in 100 ul volume for more than 5 hours. The ligated DNA fragments were heated to 100° C. for 3 minutes and were used as the DNA template in a first round of the highT PCR reaction using two primers (TGACCGGTGATCAACGTCCC, SEQ ID No. 56, and GGCGCAGACATCAATCACAG, SEQ ID No. 57). The PCR fragments were purified using a QIAquick spin column and were used as a DNA template in the second round of the highT PCR reaction using two primers (TCT-TCAGCATCAACAACGCC, SEQ ID No. 58 and TCCG-GCAAGCACGGTTGG, SEQ ID No. 59). The PCR fragments from second round of PCR reaction were purified using a QIAquick spin column and were sequenced.

To clone more of the 3' end of laccase D gene from CBS154.29 strain, inverse PCR was used. 0.4 ug of the genomic DNA from the Cerrena CBS154.29 strain was digested with SmaI restriction enzyme at 37° C. for 1.5 hours. Digested genomic DNA fragments were precipitated with ethanol. The linear DNA fragments were ligated with T4 DNA ligase in 100 ul volume for more than 5 hours. The ligated DNA fragments were heated to 100° C. for 3 minutes and were used as the DNA template in a first round of highT PCR reaction with primer TCGTCTTCGCTGAGGGCATC, SEQ ID No. 60, and primer of SEQ ID No. 56. The PCR fragments were purified using a QIAquick spin column and were used as DNA template in the second round of the highT PCR reaction using primer (CAGACCGCTGCAGC-CAACCC, SEQ ID No. 61) and primer of SEQ ID No. 59. The PCR fragments from the second round of PCR reaction were purified using a QIAquick spin column and cloned into pTOPO plasmid using TOPO cloning kit. Twenty-one clones were analyzed using Ready-To-Go PCR beads and PCR fragment from clones #Ce11 and #Ce14 were sequenced. 2809 bps of the laccase D gene sequence from the CBS154.29.49 strain is listed as SEQ ID No. 13 and the translated protein sequence is listed as SEQ ID No. 14.

Example 6

Cloning of *Cerrena unicolor* Laccase E Gene from CBS154.29 Strain

The primer of SEQ ID No. 53 was used in the lowT PCR reaction with primer of the SEQ ID No. 26 (see Example 5b). The PCR fragment was purified using a QIAquick spin column and was cloned into pTOPO plasmid using TOPO cloning kit. Eighteen clones were analyzed using Ready-To-Go PCR beads and the PCR fragment from clone #Ae17 was sequenced. 1163 bps of the laccase E gene sequence from the CBS154.29.49 strain is listed as SEQ ID No. 17 and the translated protein sequence is listed as SEQ ID No. 18.

Example 7

Expression of Laccase A Gene in *Trichoderma*

To construct the expression plasmid for the laccase A gene of the CBS strain 115.075, two primers (SEQ ID No. 45 and SEQ ID No. 36) were used in the Herculase PCR reaction containing genomic DNA template obtained from 115.075 strain, dNTPs, and 4% DMSO in 1× buffer. The PCR mixture was heated to 98° C. for 4 minutes to denature the DNA template. Herculase® II enzyme (Stratagene) was added to the tube and PCR reaction was performed in 30 cycles of 98° C. for 30 seconds, 50° C. for 30 seconds and 72° C. for 2 minute. The final extension at 72° C. was done for 5 minutes and the reaction was chilled to 4° C. The PCR fragment was purified using the QIAquick spin column and cloned into pENTR/D-TOPO vector. Fifteen clones were amplified using Ready-To-Go PCR beads and plasmid DNA was isolated from pENTR-laccaseA-CBS115.075#11 clone. The laccase A gene portion was sequenced to confirm fidelity of the PCR amplification of the laccase A gene. The plasmid of pENTR-laccaseA-CBS115.075#11 (50 ng) was converted to the expression plasmid pTrex3g-laccaseA (FIG. 1) in a 10 ul LB clonase II reaction (Invitrogen) containing 6.5 ul of TE, 1 ul of pTrex3g vector (0.1 mg/ml) and 2 ul of ClonaseII. The expression plasmid was confirmed by DNA sequencing and transformed biolistically into a *Trichoderma* strain. Transformation of the *Trichoderma* strain by the biolistic transformation method was accomplished using a Biolistic® PDS-1000/he Particle Delivery System from Bio-Rad (Hercules, Calif.) following the manufacturers instructions (see WO 05/001036 and US 2006/0003408). Sixty-six transformants were selected and were transferred to new plates. A total of 15 stable transformants were grown in 30 ml of the Proflo media for 2 days at 30° C. Five mls of 2 days old culture from Proflo media were transferred to 50 mls of defined media containing 1 mM copper. The cultures were grown for 5 days at 28° C. Culture broths were centrifuged and supernatants were used for ABTS assay.

Example 8 a. Expression of Laccase B Gene in *Aspergillus*

Figure 2:
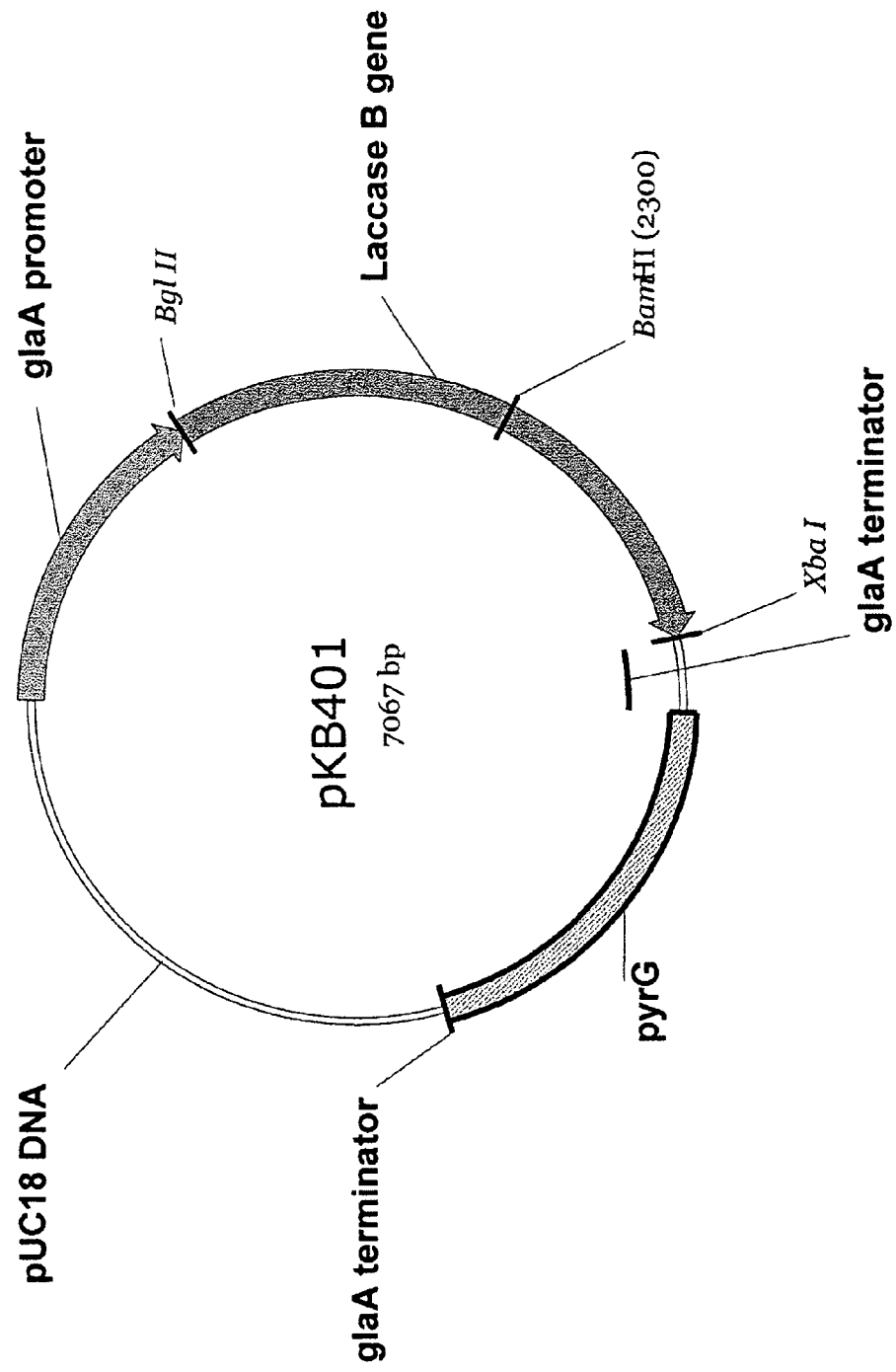
FIG. 2 is a schematic of the *Aspergillus* expression plasmid, pKB401, used in Example 8a. The laccase B gene may be replaced with other laccase genes described herein.
Figure 3:
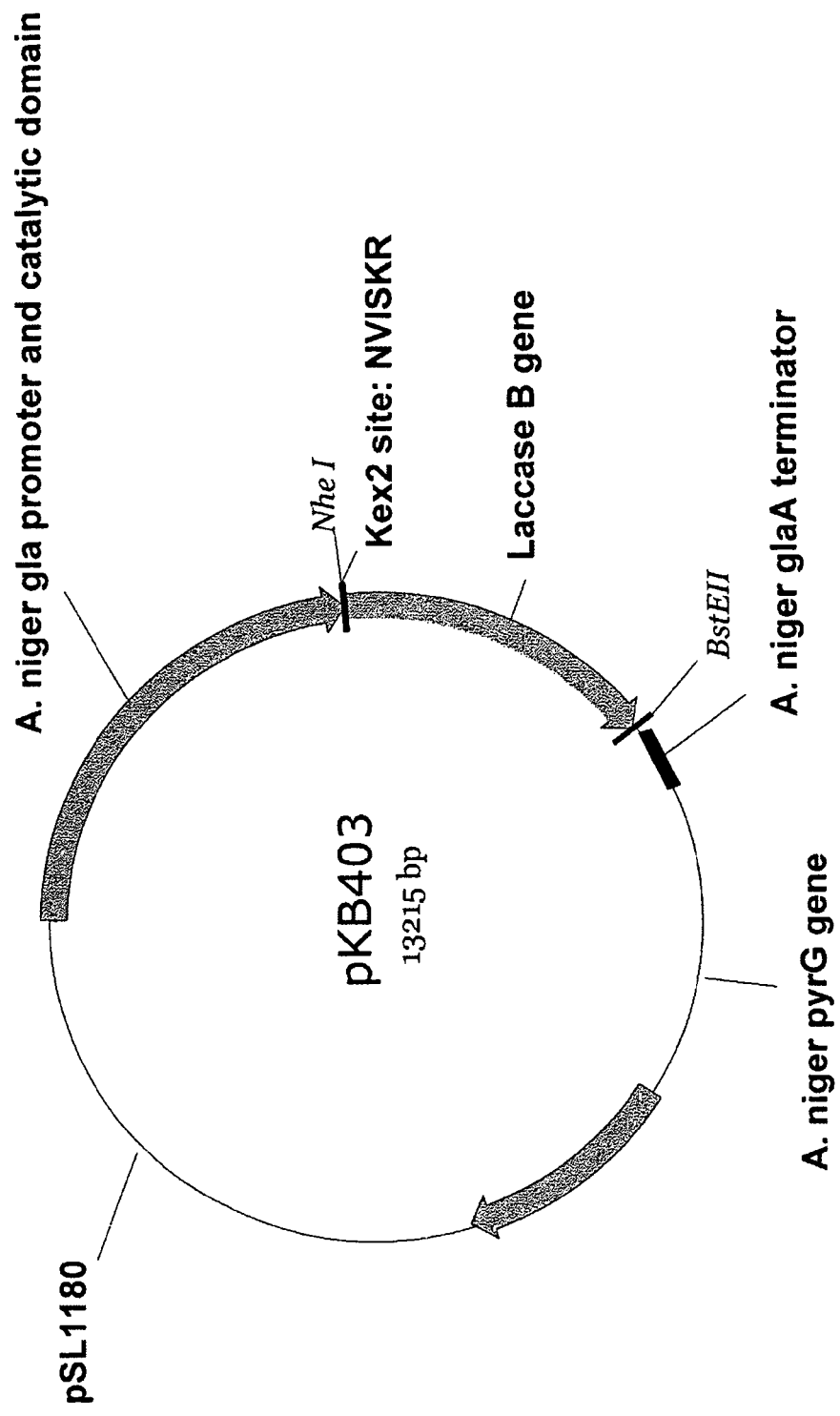
FIG. 3 is a schematic of the *Aspergillus* expression plasmid, pKB403, used in Example 8b. The laccase B gene fused to gene encoding the catalytic domain of glucoamylase. The laccase B gene may be replaced with other laccase genes described herein.

To construct the expression plasmid for the laccase B gene of the CBS strain 115.075, two primers GCAGATCTGC-GATGTCTCTTCTTCGTAGCTTGAC (SEQ ID No. 72) and GAGGTCACCTCTAGATCATGTATCAC-CTGGGCTCAAGGCATC (SEQ ID No. 73) were used in the Herculase PCR reaction containing genomic DNA template obtained from 115.075 strain (see Example 2b). The PCR fragment was purified using the QIAquick spin column and digested with restriction enzyme BglII and XbaI. The DNA fragment was purified again with the QIAquick spin column and was cloned into BglII and XbaI digested pGAPT vector. Fidelity of the plasmid was confirmed by DNA sequencing. The resulting plasmid pKB401 (FIG. 2) was transformed into *A. niger* 2445 for checking expression of laccase B gene. Thirty-four transformants were selected and were transferred onto MM plates and grew for 4 days at 30° C. A small plug of single colony including spores and mycelium was innoculated on to a CMA plate and grew for 4 days at 30° C. A plug of CMA plate containing confluent spores and mycelium was transferred into to 30 mls of Promosoy special broth (pH6.2) containing 1 mM copper. The cultures were grown for 5 days at 30° C. Culture broths were centrifuged and supernatants were used for ABTS assay.

b. Expression of Laccase B Gene in *Aspergillus* as Fusion to Catalytic Domain of the Glucoamylase To construct the fusion expression plasmid for the laccase B gene of the CBS strain 115.075, two primers TTGCTAG-CAACGTGATCTCCAAGCGTGCAATCG-GTCCAGTCACTGACCTAC (51 mer, SEQ ID No. 74) and primer of SEQ ID No. 73 were used in the Herculase PCR reaction containing genomic DNA template obtained from CBS115.075 strain (see Example 2b). The PCR fragment was purified using the QIAquick spin column and digested with NheI and BstEII and was purified again with the QIAquick spin column. This purified fragment was cloned into NheI and BstEI digested vector pGAMpR2-GV (see US Patent application US20050153399). The resulting plasmid pKB403 (FIG. 3) was confirmed by sequencing analysis and was transformed into *A. niger* 2445. Twenty-eight transformants were selected and were transferred onto MM plates and grew for 4 days at 30° C. A small plug of single colony including the spores and mycelium were innoculated onto CMA plate and grew for 4 days at 30° C. A plug of CMA plate containing confluent spores and mycelia was transferred into to 30 mls of Promosoy special broth (pH6.2) (see US Patent application US20050153399) containing 1 mM copper. The cultures were grown for 5 days at 30° C. Culture broths were centrifuged and supernatants were used for ABTS assay.

c. Expression of Laccase B Gene in *Trichoderma*

To construct expression plasmid for the laccase B gene of the CBS115.075 strain (see Example 2b). A primer was designed and obtained from Invitrogen: GTAATCATGTAT-CACCTGGGCTCAAGG (SEQ ID No. 50). The primer was used in the Herculase PCR reaction (see Example 2b) with primer of SEQ ID No. 46. The PCR fragment was purified using the QIAquick spin column and cloned into pENTR/D-TOPO vector (Invitrogen). Seventeen clones were amplified using Ready-To-Go PCR beads and plasmid DNA was isolated from pENTR-CBS115.075#1 clone (see Example 3c). The laccase B gene portion was sequenced to confirm fidelity of the PCR amplification. The plasmid of pENTR-laccaseB-CBS115.075#1 (50 ng) was converted to expression plasmid pTrex3g-laccaseB (see FIG. 1 with the laccase A gene replaced with the laccase B gene) in a 10 ul LB clonase II reaction (Invitrogen) containing 6.5 ul of TE, 1 ul of pTrex3g vector (0.1 mg/ml) and 2 ul of ClonaseII. The expression plasmid was confirmed by DNA sequencing and transformed biolistically into a *Trichoderma* strain. Sixty transformants were selected and were transferred to new plates. A total of 20 stable transformants were grown in 30 ml of the Proflo media for 2 days at 30° C. Three mls of 2 day old culture from Proflo media were transferred to 30 mls of defined media (see US Patent Application 20050153399) containing 1 mM copper. The cultures were grown for 4 days at 28° C. Culture broths were centrifuged and supernatants were used for ABTS assay.

d. Expression of the Laccase B Gene in *Trichoderma* as CBH1 Fusion

To construct the expression plasmid for the laccase B gene of the CBS strain 115.075, a primer was designed and obtained from Invitrogen (GGACTAGTGTCGCCGTTTA-CAAACGCGCAATCGGTCCAGTCACTGACC, SEQ ID No. 65). The primer was used in combination with the reverse primer (obtained from New England Biolab) in the Herculase PCR reaction containing pENTR-laccaseB CBS115075#1 (see example 3c) as the DNA template. The PCR fragment (SEQ ID No. 66)

```
ACTAGTGTCG CCGTTTACAA ACGCGCAATC GGTCCAGTCA CTGACCTACA    50
TATAGTGAAC CAGAATCTCG ACCCAGATGG TTTCAACCGC CCCACTGTAC   100
TCGCAGGTGG TACTTTCCCC GGTCCTCTGA TTCGTGGTAA CAAGGTACGC   150
TTCATAACCG CCCTCCGTAG ACGTAGGCTT CGGCTGACAT GACCATCATC   200
TGTAGGGAGA TAACTTTAAA ATTAATGTGA TTGACGACTT GACAGAGCAC   250
AGTATGCTCA AGGCTACGTC CATCGTAAGT CCCTGATTAA CGTTTCACCT   300
GGTCATATCG CTCAACGTCT CGAAGCACTG GCATGGGTTC TTCCAGAAGG   350
GAACCAACTG GGCCGATGGC CCCGCCTTTG TCACCCAATG TCCTATCACA   400
TCAGGAAACG CCTTCCTGTA TGATTTCAAC GTTCCGGACC AAGCTGGTAC   450
TTTCTGGTAC CACAGCCATC TCTCTACACA GTATTGTGAC GGTCTTCGTG   500
GTGCCTTTGT CGTCTATGAT CCTAATGATC CAACAAGCA ACTCTATGAT    550
GTTGATAACG GCAAGTTCCT TGCATATTTC ATTTCTATCA TATCCTCACC   600
TGTATTGGCA CAGAAAGCAC CGTGATTACC TTGGCTGATT GGTATCATGC   650
CCTTGCTCAG ACTGTCACTG GTGTCGCGTG AGTGACAAAT GGCCCTCAAT   700
TGTTCACATA TTTTCCTGAT TATCATATGA TAGAGTATCT GATGCAACGT   750
TGATCAACGG ATTGGGACGT TCGGCCACCG GCCCCGCAAA TGCCCCTCTG   800
GCGGTCATCA GTGTCGAGCG GAATAAGAGG TCAGTTCCAT AATTATGATT   850
ATTTCCCGCG TTACTTCCTA ACAATTATTT TTGTATCCCT CCACAGATAT   900
CGTTTCCGAT TGGTTTCTAT TTCTTGCGAC CCTAACTTTA TTTTCTCAAT   950
TGACCACCAC CCAATGACCG TAATTGAGAT GGACGGTGTT AATACCCAAT  1000
CTATGACCGT AGATTCGATC CAAATATTCG CAGGTCAACG ATATTCATTT  1050
GTCGTAGGTT ATTATAAACT GCCCACCGAT CATCTCTCAC GTAACTGTTA  1100
TAGATGCAAG CCAACCAACC AGTTGGAAAT TATTGGATCC GCGCTAAACC  1150
```

```
TAATGTTGGG AACACAACTT TCCTTGGAGG CCTGAACTCC GCTATATTAC    1200

GATATGTGGG AGCCCCTGAC CAAGAACCGA CCACTGACCA AACACCCAAC    1250

TCTACACCGC TCGTTGAGGC GAACCTACGA CCCCTCGTCT ATACTCCTGT    1300

GGTATGTTGT TCTCGTTACA TATACCAAAC CTAATATGAA GACTGAACGG    1350

ATCTACTAGC CGGGACAGCC ATTCCCTGGC GGTGCTGATA TCGTCAAGAA    1400

CTTAGCTTTG GGTTTCGTAC GTGTATTTCA CTTCCCTTTT GGCAGTAACT    1450

GAGGTGGAAT GTATATAGAA TGCCGGGCGT TTCACAATCA ATGGAGCGTC    1500

CCTCACACCT CCTACAGTCC CTGTACTACT CCAGATCCTC AGTGGTACTC    1550

ACAATGCACA GGATCTTCTC CCAGCAGGAA GCGTGATCGA ACTTGAACAG    1600

AATAAAGTTG TCGAAATCGT TTTGCCCGCT GCGGGCGCCG TTGGCGGTCC    1650

TCATCCTTTT CACTTACATG GTGTAAGTAT CAGACGTCCT CATGCCCATA    1700

TTGCTCCGAA CCTTACACAC CTGATTTCAG CACAATTTCT GGGTGGTTCG    1750

TAGCGCCGGT CAAACCACAT ACAATTTCAA TGATGCTCCT ATCCGTGATG    1800

TTGTCAGTAT TGGCGGTGCA AACGATCAAG TCACGATCCG ATTTGTGGTA    1850

TGTATCTCGT GCCTTGCATT CATTCCACGA GTAATGATCC TTACACTTCG    1900

GGTTCTCAGA CCGATAACCC TGGCCCATGG TTCCTTCACT GTCACATTGA    1950

CTGGCATTTG GAGGCTGGGT TCGCTGTAGT CTTTGCGGAG GGAATCAATG    2000

GTACTGCAGC TGCTAATCCA GTCCCAGGTA AGACTCTCGC TGCTTTGCGT    2050

AATATCTATG AATTTAAATC ATATCAATTT GCAGCGGCTT GGAATCAATT    2100

GTGCCCATTG TATGATGCCT TGAGCCCAGG TGATACATGA TTACAAGGGT    2150

Figure 4:
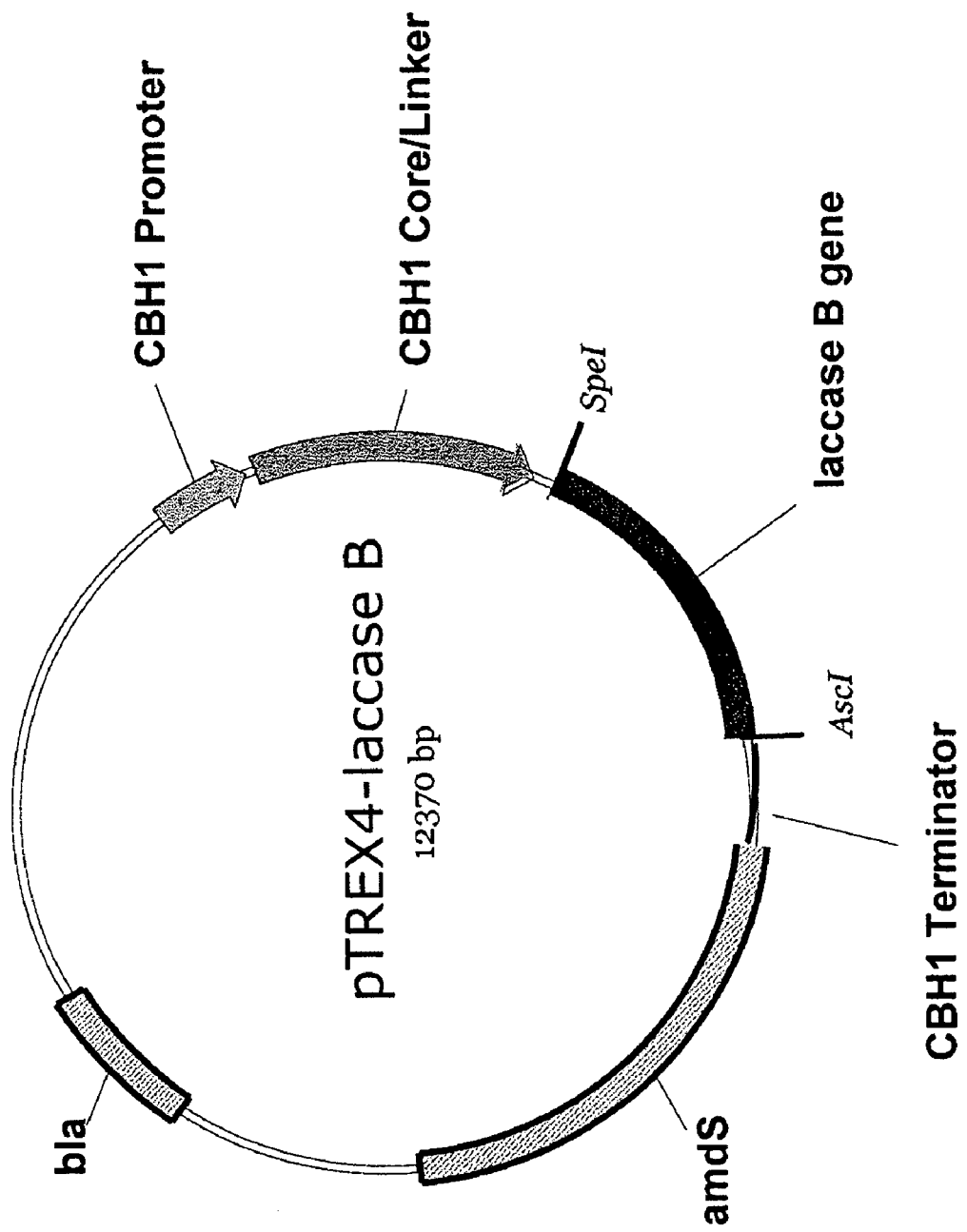
FIG. 4 is a schematic of the *Trichoderma* expression plasmid, pTrex4-laccaseB, used in Example 8d. The laccase B gene fused to gene encoding the catalytic domain of CBH1. The laccase B gene may be replaced with other laccase genes described herein.

GGGCGCGCC                                                 2159
``` was purified using the QIAquick spin column and digested with restriction enzymes SpeI and AscI. This fragment (SEQ ID No. 66) was then cloned into pTrex4 vector which was also digested with SpeI and AscI to create the expression plasmid (pTrex4-laccaseB, FIG. 4). The fidelity of the expression plasmid was confirmed by DNA sequencing and transformed biolistically into a *Trichoderma* strain. More than 100 transformants were generated and sixty transformants were transferred to new plates. A total of 20 stable transformants were grown in 30 ml of the Proflo media for 2 days at 30° C. Five mls of 2 days old culture from Proflo media were transferred to 50 mls of defined media containing 1 mM copper. The cultures were grown for 4 days at 28° C. Culture broths were centrifuged and supernatants were used for ABTS assay.

Example 9 a. Expression of Laccase B Gene of the CBS Strain 115.075 in *Streptomyces*

Figure 5:
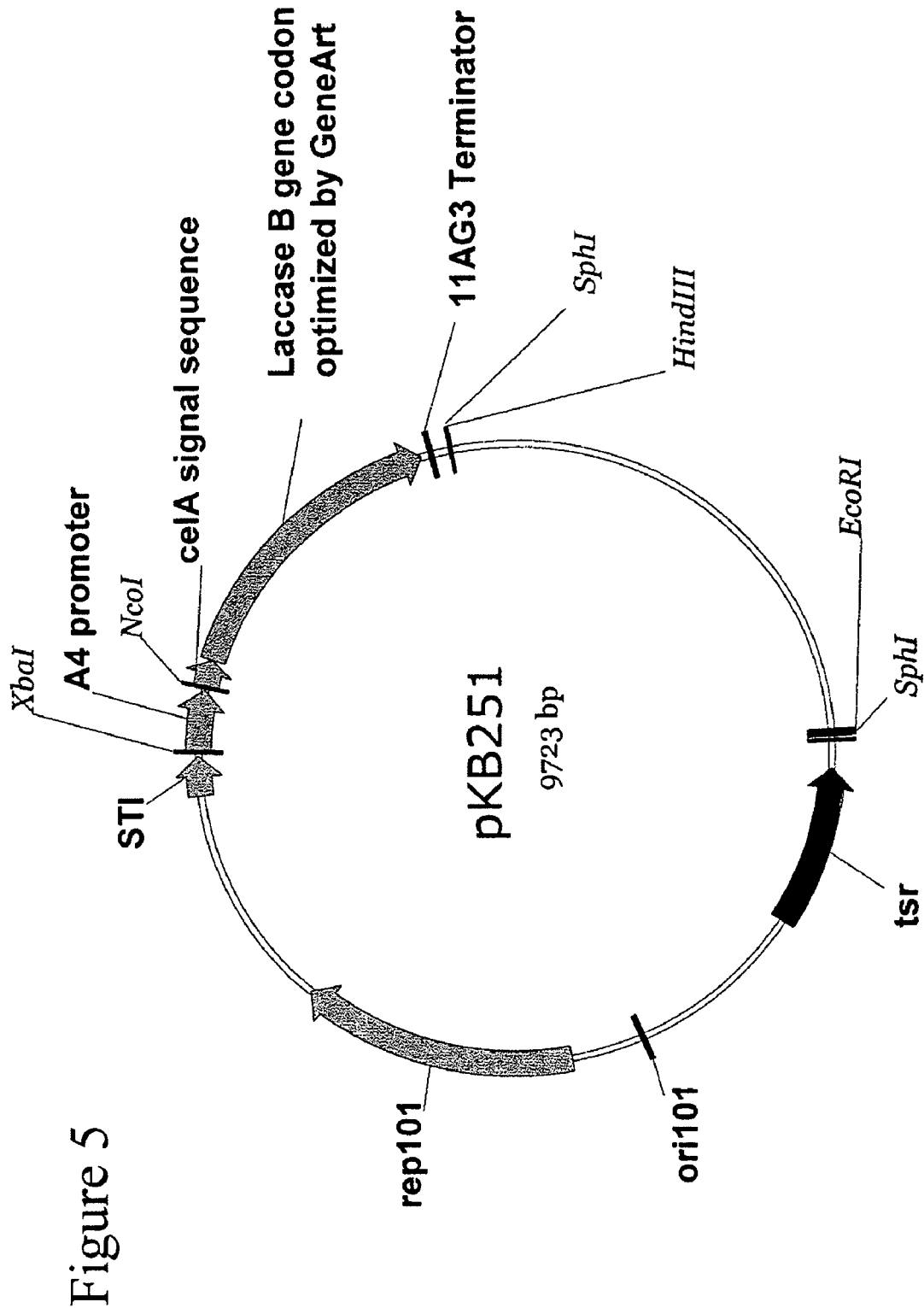
FIG. 5 is a schematic of the *Streptomyces* expression plasmid (pKB251) for codon optimized laccase B gene, used in Example 9.

The laccase B protein sequence was used for codon optimization according to *Streptomyces lividans* codon usage. To construct the expression plasmid for the synthesized laccase B gene of the CBS115.075 strain in *Streptomyces*, two primers ACGCAGCCTGAACTAGTTGCGATCCTCTAGAG (SEQ ID No. 75) and CTCTGATCAAGGTCATCAGGT-GTCGCCCGGGGACAGG (SEQ ID No. 76) were used in the Herculase PCR reaction containing the optimized DNA template (See Example 2b). The PCR fragment was purified using the QIAquick spin column and was digested with XbaI and BclI. The digested fragment was purified by the QIAquick spin column and was cloned into XbaI and BamHI disgested pKB105 (see US 20060154843). The correctness of the resulting plasmid pKB251 (FIG. 5) was confirmed by DNA sequencing. The DNA of plasmid pKB251 was transformed into *Streptomyces lividans* g3s3 strain (see US 20060154843). Twelve thiostrepton resistant transformants were picked and transferred into seed shake flask (20 ml of TSG medium containing 50 ug/ml of thiostrepton in DMSO), grown for 2 days at 30° C. Three mls of 2 days old culture from seed shake flask were transferred to 30 mls of *Streptomyces* modified production medium II containing 1 mM copper. The cultures were grown for 4 days at 30° C. Culture broths were centrifuged and supernatants were used for ABTS assay.

Example 10

Expression of the Laccase B Gene in *Trichoderma* as CBH1 Fusion Using codon optimized synthetic gene

```
The optimized synthtetic laccase B gene (SEQ ID NO:67):
ACTAGTGTCG CCGTTTACAA ACGCGCAATC GGTCCCGTCA CTGACCTGCA    50

TATTGTGAAC CAGAATCTCG ACCCCGATGG TTTCAACCGC CCCACTGTCC    100
```

-continued

```
TCGCAGGTGG TACTTTCCCC GGTCCTCTGA TTCGTGGTAA CAAGGGAGAT    150

AACTTTAAAA TTAATGTGAT TGACGACTTG ACAGAGCACA GCATGCTCAA    200

GGCTACGTCC ATCCACTGGC ATGGCTTCTT CCAGAAGGGA ACCAACTGGG    250

CCGATGGCCC CGCCTTTGTC ACCCAATGTC CTATCACATC AGGAAACGCC    300

TTCCTGTACG ATTTCAACGT TCCGGACCAA GCTGGTACTT TCTGGTACCA    350

CAGCCATCTC TCTACACAGT ACTGTGACGG TCTTCGTGGT GCCTTTGTCG    400

TCTACGATCC TAATGATCCC AACAAGCAAC TCTACGATGT TGATAACGGC    450

AACACCGTGA TTACCTTGGC TGATTGGTAC CATGCCCTTG CTCAGACTGT    500

CACTGGTGTC GCAGTCTCTG ATGAACGTT GATCAACGGA TTGGGACGTT     550

CGGCCACCGG CCCCGCAAAT GCCCCTCTGG CGGTCATCAG CGTCGAGCGC    600

AATAAGCGCT ATCGTTTCCG ATTGGTTTCT ATTTCTTGCG ACCCTAACTT    650

TATTTTCTCA ATTGACCACC ACCCCATGAC CGTCATTGAG ATGGACGGTG    700

TTAATACCCA ATCTATGACC GTAGATTCGA TCCAAATCTT CGCAGGTCAA    750

CGATACTCAT TTGTCATGCA AGCCAACCAA CCAGTTGGAA ATTACTGGAT    800

CCGCGCTAAA CCTAATGTTG GCAACACAAC TTTCCTTGGA GGCCTGAACT    850

CCGCTATCTT GCGATACGTG GGAGCCCCTG ACCAAGAACC GACCACTGAC    900

CAAACACCCA ACTCTACACC GCTCGTTGAG GCGAACCTGC GACCCCTCGT    950

CTACACTCCT GTGCCGGGAC AGCCATTCCC TGGCGGTGCT GATATCGTCA   1000

AGAACTTGGC TTTGGGTTTC AATGCCGGGC GTTTCACAAT CAATGGAGCG   1050

TCCCTCACAC CTCCTACAGT CCCTGTCCTG CTCCAGATCC TCAGCGGTAC   1100

TCACAATGCA CAGGATCTTC TCCCGGCAGG AAGCGTGATC GAACTTGAAC   1150

AGAATAAAGT TGTCGAAATC GTTTTGCCCG CTGCGGGCGC CGTTGGCGGT   1200

CCTCATCCTT TTCACTTGCA TGGTCACAAT TTCTGGGTGG TTCGTAGCGC   1250

CGGTCAAACC ACATACAATT TCAATGATGC TCCTATCCGT GATGTTGTCA   1300

GCATTGGCGG TGCAAACGAT CAAGTCACGA TCCGATTTGT GACCGATAAC   1350

CCTGGCCCAT GGTTCCTTCA CTGTCACATT GACTGGCATT TGGAGGCTGG   1400

ATTCGCTGTC GTCTTTGCGG AGGGAATCAA TGGTACTGCA GCTGCTAATC   1450

CCGTCCCGGC GGCTTGGAAT CAATTGTGCC CGTTGTACGA TGCCTTGAGC   1500

CCGGGTGATA CATGAGGCGC GCC                                1523
``` encoding the laccase B gene was synthesized by McLab Inc. (Molecular Cloning Laboratories, 384 Oyster Point Blvd, Suite 15, South San Francisco, Calif. 94080). The synthetic plasmid DNA was digested with restriction enzymes SpeI and AscI and the 1.5 kb DNA fragment was isolated from gel and cloned into pTrex4 vector which was also digested with SpeI and AscI to create the expression plasmid (pTrex4-laccase-Bopt), which is similar to the expression plasmid shown in FIG. 4 except that the codon optimized laccase B gene replaced the (non-optimized) laccase B gene. The plasmid was transformed biolistically into a *Trichoderma* strain. More than 30 transformants were generated and were transferred to new plates. A total of 20 stable transformants were selected and mycelia were transferred to 30 mls of defined media containing 1 mM copper. The cultures were grown for 4 days at 28° C. Culture broths were centrifuged and supernatants were used for ABTS assay.

Example 11 a. Expression of Laccase D Gene in *Trichoderma*

To construct the expression plasmid for the laccase D gene of the CBS115.075 strain, two primers (SEQ ID No. 63 and SEQ ID No. 64) were used in the Herculase PCR reaction containing genomic DNA template obtained from CBS115.075 strain (see Example 2b). The PCR fragment was purified using the QIAquick spin column and cloned into pENTR/D-TOPO vector. Sixteen clones were amplified using Ready-To-Go PCR beads and four plasmid DNAs were sequenced. The pENTR-laccaseD CBS115.075#2 clone was selected. The pENTR-laccaseD CBS115.075#2 plasmid (50 ng) was converted to expression plasmid pTrex3g-laccaseD, which is similar to the expression plasmid shown in FIG. 1 except that the codon optimized laccase D gene replaced the laccase A gene, in a 10 ul LB clonase II reaction containing 6.5 ul of TE, 1 ul of pTrex3g vector (0.1 mg/ml) and 2 ul of ClonaseII. The expression plasmid was confirmed again by DNA sequencing and transformed biolistically into a *Trichoderma* strain. Forty-five transformants were selected and were transferred to new plates. Mycelia from 28 stable transformants were transferred to 30 mls of defined media containing 0.5 mM copper. The cultures were grown for 4 days at 28° C. Culture broths were centrifuged and supernatants were used for ABTS assay.

b. Expression of the Laccase D Gene in *Trichoderma* as CBH1 Fusion

To construct the expression plasmid for the laccase D gene of the CBS115.075 strain, two primers (GGACTAGTGTCGCCGTTTACAAACGCGCAATTGGGCCCGTGGCCGAC, SEQ ID No. 68) and (AAGGCGCGCCTTAAATAGCAGTTCCTTTCTTAG, SEQ ID No. 69) were designed and obtained from Invitrogen. The primers were used in the Herculase PCR reaction containing genomic DNA of the CBS115.075 strain as the DNA template. The PCR fragment was purified using the QIAquick spin column and digested with restriction enzymes SpeI and AscI and cloned into pTrex4 vector (see U.S. patent application Ser. No. 10/590,956; WO 05/093050) which was also digested with SpeI and AscI to create the expression plasmid (pTrex4-laccaseD). The fidelity of the expression plasmid was confirmed by DNA sequencing and transformed biolistically into *Trichoderma* strain. More than 300 transformants were generated and sixty transformants were transferred to new plates. Mycelia of 25 stable transformants were transferred to 30 mls of defined media containing 0.5 mM copper. The cultures were grown for 4 days at 28° C. Culture broths were centrifuged and supernatants were used for ABTS assay.

Example 12

Expression of the Laccase D Gene in *Trichoderma* as CBH1 Fusion Using Codon Optimized synthetic gene

```
DNA (SEQ ID NO:70):
ACTAGTGTCG CCGTTTACAA ACGCGCTATT GGACCAGTTG CTGATCTGCA      50

CATCGTTAAC AAGGATTTGG CCCCAGACGG CGTCCAGCGC CCAACTGTTC     100

TGGCCGGTGG AACTTTTCCG GGCACGCTGA TTACCGGTCA AAAGGGCGAC     150

AACTTCCAGC TGAACGTGAT TGATGACCTG ACCGACGATC GCATGTTGAC     200

CCCTACTTCG ATCCATTGGC ATGGTTTCTT CCAGAAGGGA ACCGCCTGGG     250

CCGACGGTCC GGCTTTCGTT ACACAGTGCC CTATTATCGC AGACAACTCC     300

TTCCTCTACG ATTTCGACGT TCCCGACCAG GCGGGCACCT TCTGGTACCA     350

CTCACACTTG TCTACACAGT ACTGCGACGG TCTGCGCGGT GCCTTCGTTG     400

TTTACGACCC CAACGACCCT CACAAGGACC TTTATGATGT CGATGACGGT     450

GGCACAGTTA TCACATTGGC TGACTGGTAT CACGTCCTCG CTCAGACCGT     500

TGTCGGAGCT GCTACACCCG ACTCTACGCT GATTAACGGC TTGGGACGCA     550

GCCAGACTGG CCCCGCCGAC GCTGAGCTGG CCGTTATCTC TGTTGAACAC     600

AACAAGAGAT ACCGTTTCAG ACTCGTCTCC ATCTCGTGCG ATCCCAACTT     650

CACTTTTAGC GTCGACGGTC ACAACATGAC GGTTATCGAG GTTGATGGCG     700

TGAATACCCG CCCTCTCACC GTCGATTCCA TTCAAATTTT CGCCGGCCAG     750

CGATACTCCT TTGTGCTGAA TGCCAATCAG CCCGAGGATA ACTACTGGAT     800

CCGCGCTATG CCTAACATCG GACGAAACAC CACTACCCTT GATGGCAAGA     850

ATGCCGCTAT CCTGCGATAC AAGAACGCCA GCGTTGAGGA GCCCAAAACC     900

GTCGGAGGAC CCGCGCAGAG CCCATTGAAC GAGGCCGACC TGCGACCTCT     950

GGTGCCCGCT CCTGTCCCTG GCAACGCAGT TCCTGGTGGT GCGGACATCA    1000

ACCACCGCCT GAACCTGACA TTCAGCAACG GCCTCTTCTC TATCAATAAC    1050

GCATCATTTA CAAACCCCAG CGTCCCTGCC TTGTTGCAGA TTCTTTCCGG    1100

CGCACAAAAC GCTCAGGATC TGCTTCCCAC CGGTTCTTAT ATCGGCTTGG    1150

AGTTGGGCAA GGTCGTTGAA CTCGTGATCC CTCCCTTGGC CGTTGGTGGC    1200

CCCCATCCAT TCCACTTGCA CGGCCACAAC TTTTGGGTCG TCCGAAGCGC    1250

TGGTTCTGAC GAGTATAATT TCGACGATGC AATTTGCGC GACGTGGTCA    1300

GCATTGGCGC GGGAACTGAC GAGGTTACTA TCCGTTTTGT CACTGATAAC    1350
```

-continued

```
CCAGGCCCTT GGTTCCTCCA TTGCCACATC GACTGGCACC TCGAAGCCGG     1400

CCTCGCCATT GTTTTCGCCG AAGGCATCAA TCAAACCGCA GCCGCCAACC     1450

CGACTCCACA GGCCTGGGAC GAACTCTGCC CCAAGTATAA CGGACTCTCC     1500

GCTTCCCAGA AAGTGAAGCC CAAGAAGGGA ACAGCCATCT AAGGCGCGCC     1550
``` encoding the laccase D gene (based on the gene from CBS115.075) was synthesized by DNA2.0 Inc. (1455 Adams Drive, Menlo Park, Calif. 94025). The synthetic plasmid DNA was digested with restriction enzymes SpeI and AscI and The 1.5 kb DNA fragment was isolated from gel and cloned into pTrex4 vector which was also digested with SpeI and AscI to create the expression plasmid (pTrex4-laccase-Dopt). The plasmid was transformed biolistically into a *Trichoderma* strain. Forty transformants were transferred to new plates. A total of 24 stable transformants were selected and mycelia were transferred to 30 mls of defined media containing 0.5 mM copper. The cultures were grown for 4 days at 28° C. Culture broths were centrifuged and supernatants were used for ABTS assay.

Example 13

Expression of the Laccase D Gene in *Bacillus* as BCE103 Fusion Using optimized synthetic gene

```
DNA (SEQ ID NO:71):
GGATCCTGAA GCTATCGGTC CGGTTGCAGA TTTACACATC GTAAACAAAG      50

ATCTTGCACC TGACGGCGTT CAACGTCCAA CTGTACTTGC TGGTGGAACA     100

TTCCCTGGTA CACTTATTAC TGGTCAAAAA GGTGACAACT TCCAATTAAA     150

CGTAATTGAC GATCTTACAG ATGACCGTAT GCTTACACCG ACTTCAATTC     200

ACTGGCACGG TTTCTTTCAA AAAGGAACAG CATGGGCTGA TGGTCCTGCA     250

TTCGTTACAC AATGTCCAAT CATTGCTGAT AACTCTTTCC TTTACGATTT     300

TGACGTTCCT GATCAAGCTG GTACATTCTG GTATCACTCA CACTTATCCA     350

CACAATACTG CGATGGACTT CGCGGAGCTT TCGTAGTTTA CGACCCAAAC     400

GATCCTCATA AAGACCTTTA CGATGTAGAT GATGGTGGAA CAGTTATCAC     450

ATTAGCTGAT TGGTACCATG TACTTGCTCA AACAGTTGTA GGTGCAGCTA     500

CACCAGATTC AACACTTATC AATGGATTAG GACGTTCTCA AACTGGTCCT     550

GCTGACGCAG AACTTGCTGT AATCTCTGTT GAACATAACA AACGTTACAG     600

ATTCCGTCTT GTTAGCATTT CTTGCGATCC AAACTTCACA TTTTCAGTTG     650

ACGGACATAA CATGACAGTT ATCGAAGTAG ATGGTGTAAA CACACGTCCA     700

CTTACTGTAG ACTCTATCCA AATCTTCGCA GGACAACGTT ACTCATTCGT     750

ATTAAACGCA AATCAACCAG AAGATAACTA CTGGATTCGT GCAATGCCAA     800

ACATCGGACG TAACACTACA ACTCTTGACG GCAAAAACGC AGCTATTCTT     850

CGTTACAAAA ACGCTTCTGT TGAAGAACCT AAAACAGTTG GTGGACCAGC     900

ACAATCACCA CTTAACGAAG CTGACTTACG TCCACTGGTT CCAGCACCTG     950

TACCTGGAAA CGCTGTACCA GGAGGTGCTG ATATTAATCA TAGACTTAAC     100

CTTACTTTCT CTAACGGTCT GTTCTCAATC AACAACGCTT CATTCACAAA    1050

TCCTTCAGTT CCAGCACTTT TACAAATTCT TAGCGGTGCA CAAAATGCTC    1100

AGGATCTTTT ACCAACTGGA TCTTACATTG GTCTTGAACT GGGTAAAGTA    1150

GTTGAATTAG TAATTCCTCC GCTTGCTGTA GGTGGACCAC ATCCTTTCCA    1200

TCTTCACGGT CATAACTTCT GGGTTGTACG TTCTGCTGGT TCAGATGAAT    1250

ACAACTTCGA TGACGCAATT CTTCGTGATG TTGTATCTAT TGGTGCTGGA    1300

ACAGATGAAG TAACTATTCG TTTCGTAACA GATAACCCTG GTCCTTGGTT    1350

CTTACATTGT CATATCGATT GGCATCTTGA AGCTGGACTT GCTATTGTTT    1400
```

```
                                    -continued
TCGCTGAAGG AATCAATCAA ACAGCTGCAG CTAACCCAAC ACCTCAAGCA    1450

TGGGACGAAT TATGTCCAAA ATACAACGCA CTTTCTCCAG GAGATACTTA    1500

Figure 6:
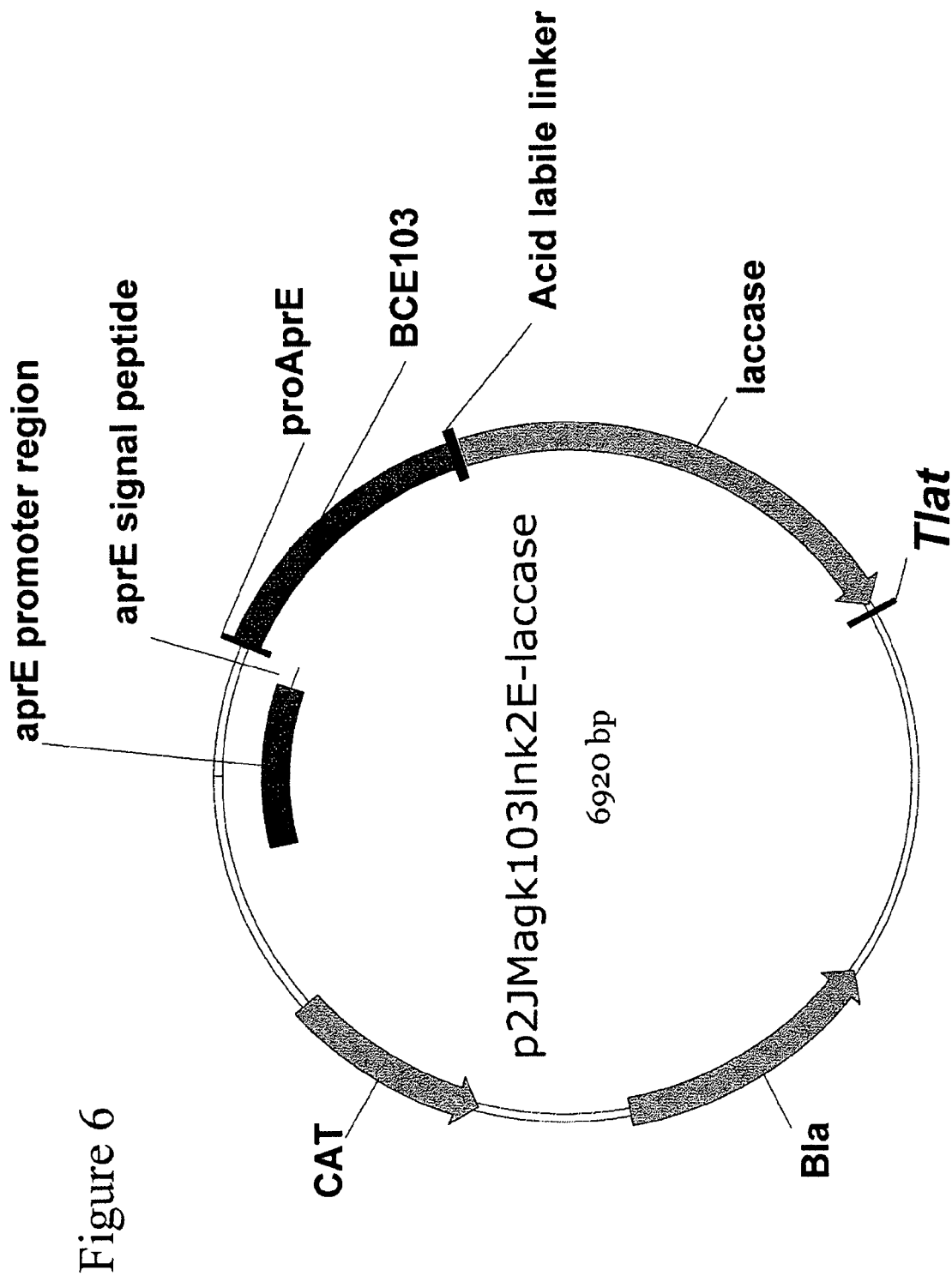
FIG. 6 is a schematic of the *Bacillus* expression plasmid (p2JMagk103lnk2E-laccase) for codon optimized laccase D gene fused to the gene encoding BCE103, used in Example 13.

AAAGCTT                                                   1507
``` encoding the laccase D gene (based on the gene from CBS115.075) was synthesized by DNA2.0 Inc. (1455 Adams Drive, Menlo Park, Calif. 94025). The synthetic plasmid DNA was digested with restriction enzymes BamHI and HindIII and the 1.5 kb DNA fragment was isolated from a gel and ligated into the p2JMagk103lnk2 vector (see US20050202535A1) digested with the same two restriction enzymes to create the expression plasmid p2JMagk103lnk2E-laccase (FIG. 6). The plasmid was transformed into a *B. subtilis* strain (degUHY32, oppA, DspoIIE, DaprE, DnprE, Depr, DispA, Dbpr, Dvpr, DwprA, DmprybfJ, DnprB, amyE::xylRPxylAcomK-ermC) (see US20050202535A1). Two transformants were selected on Luria Broth agar plates with 5 mg/ml chloramphenicol, and then to select for clones with higher gene copy numbers, colonies were serially streaked on Luria Broth agar plates with 25 mg/ml chloramphenicol until rapid colony growth was obtained. The amplified transformants were inoculated into 30 ml MBD medium (see US20050202535A1) containing 0.5 mM copper. The cultures were grown for 60 h at 37° C. Culture broths were centrifuged and supernatants were used for ABTS assay.

Example 14

Bleaching of Solubilized Indigo with Different Laccases

An assay for the bleaching of the solubilized indigo substrate by laccase/mediator combinations was performed in a 96-well microtitre plate as follows A saturated solution of indigo in N-methylpyrrolidone (NMP) was prepared by stirring indigo (30 mg) in NMP (10 ml) at room temperature for 5 hours. The NMP solution was diluted 10-fold into an aqueous buffer solution resulting in a blue solution. For example, dilution into 50 mM sodium acetate buffer at pH 5, or 50 mM sodium phosphate buffer at pH 7. Solutions were shaken well immediately before use.

The assay for the bleaching of the solubilized indigo substrate was performed in a 96-well microtitre plate whereby each well received the soluble indigo solution in 50 mM sodium acetate buffer at pH 5 (180 uL), laccase (10 ppm enzyme) and mediator solution (from a 20 mM stock solution in methanol). The total volume of each well was adjusted to 200 uL with deionzed water. A control containing laccase only was run in duplicate. The plate was sealed and incubated at 50° C. for 2 hours at 800 rpm on a heated agitator (Thermomixer, Eppendorf). Following this period, the plates were unsealed and a solution of ascorbic acid (20 uL of a 10% aqueous solution) added to each well in order to reduce the oxidized forms of the mediators. The extent of indigo bleaching was then assessed by determining the absorbance for each well at 600 nm using a microtitre plate reader. The lower the absorbance reading, the greater the extent of indigo bleaching.

Figure 7:
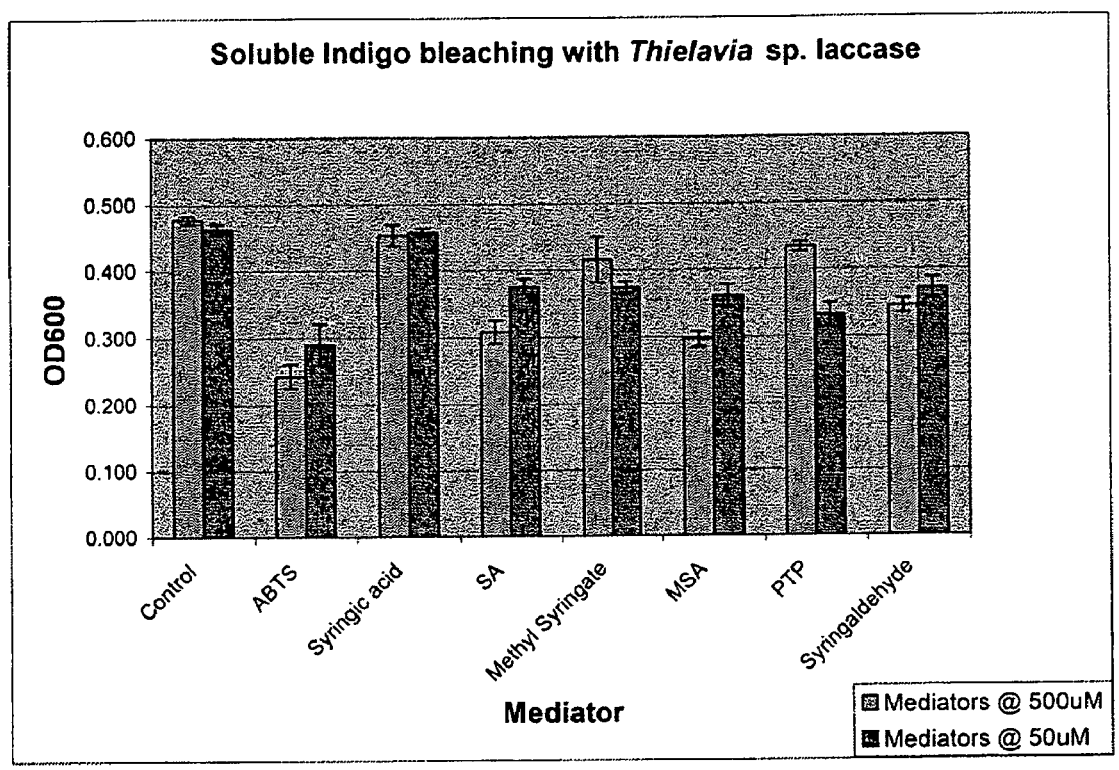
FIG. 7 is a bar graph showing the results of bleaching soluble indigo using a *Thielavia* sp. laccase and a variety of mediators at 50 and 500 uM concentrations.

FIG. 7 shows the results for a *Thielavia* sp. laccase (Ecostone LCC10, AB enzymes, Darmstadt, Germany). The mediators used were 2,2'-azino-bis(3-ethylbenzthiazoline-6-sulphonic acid (ABTS), syringic acid, 4-carboxamido-2,6-dimethoxyphenol (SA), methyl syringate (MS), 4-(N-methyl carboxamido)-2,6-dimethoxyphenol (MSA), 10-(carboxypropyl)-phenothiazine (PTP) and syringaldehyde. The changes in absorbance at 600 nm relative to control are listed in Table 1 where the greatest change in absorbance corresponds to the largest extent of indigo bleaching.

At a mediator concentration of 500 uM, the most effective mediator for indigo bleaching was ABTS, followed by the N-methyl amide (MSA) and the unsubstituted amide, 4-carboxamido-2,6-dimethoxyphenol (SA). At the lower mediator concentration of 50 uM, ABTS was still the most effective mediator, with the remaining mediators being more or less equivalent. The exception was syringic acid, which bleached soluble indigo no more effectively than the control condition.

TABLE 1

Change in absorbance at 600 nm following bleaching of soluble indigo using a *Thielavia* sp. laccase and a variety of mediators at 500 and 50 uM concentrations (n = 2).

| Mediator | 500 mM Concentration | | 50 mM Concentration | |
| --- | --- | --- | --- | --- |
| | ΔA600 | Std Dev | ΔA600 | Std Dev |
| Control | 0 | 0.008 | 0 | 0.010 |
| ABTS | 0.235 | 0.019 | 0.174 | 0.032 |
| Syringic acid | 0.024 | 0.017 | 0.005 | 0.009 |
| SA | 0.170 | 0.018 | 0.088 | 0.014 |
| Methyl Syringate | 0.062 | 0.035 | 0.090 | 0.012 |
| MSA | 0.181 | 0.013 | 0.103 | 0.018 |
| PTP | 0.044 | 0.009 | 0.132 | 0.020 |
| Syringaldehyde | 0.132 | 0.012 | 0.092 | 0.017 |

Example 15

Soluble Indigo Bleaching Assay with Different Laccases at Two pH Values

Laccases derived from *Myceliophtora* (Denilite® II, Novozymes, Bagsvaerd, Denmark), *Thielavia* (Ecostone LCC10, AB enzymes, Darmstadt, Germany) and *Cerrena* sp. were assessed for their ability to bleach solubilized indigo in conjunction with low molecular weight mediators at two pH values.

Figure 8:
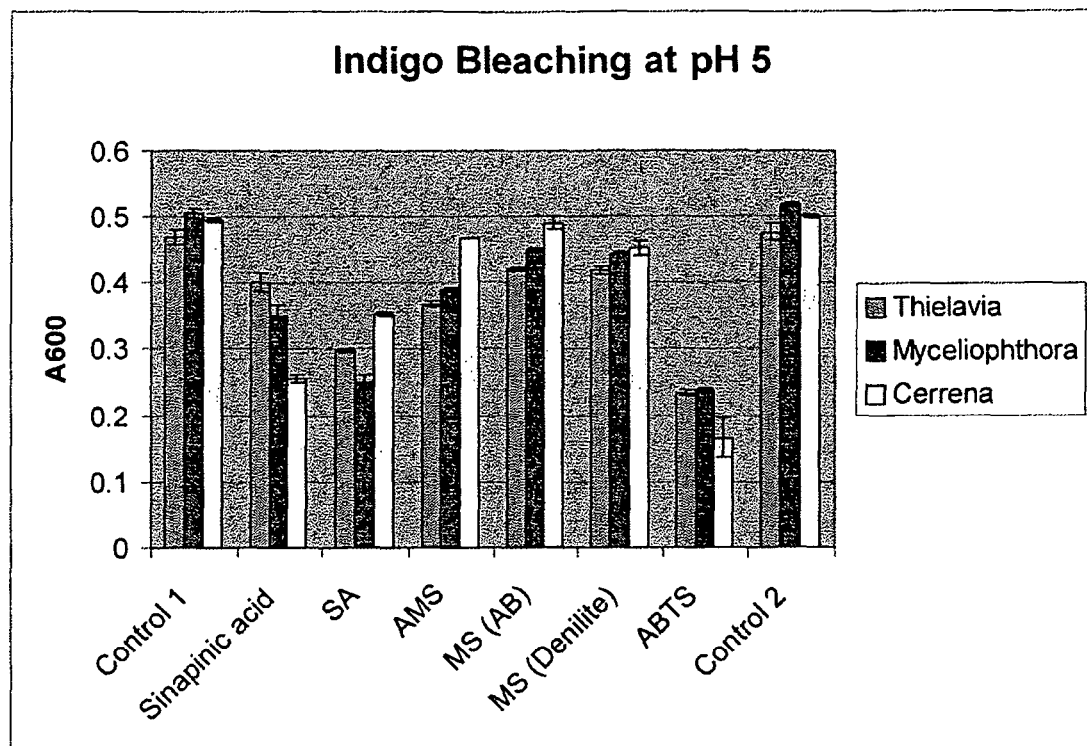
FIG. 8 is a bar graph showing the results of bleaching of soluble indigo using a *Thielavia, Myceliophthora* and *Cerrena* sp. laccase and a variety of mediators at pH 5.
Figure 9:
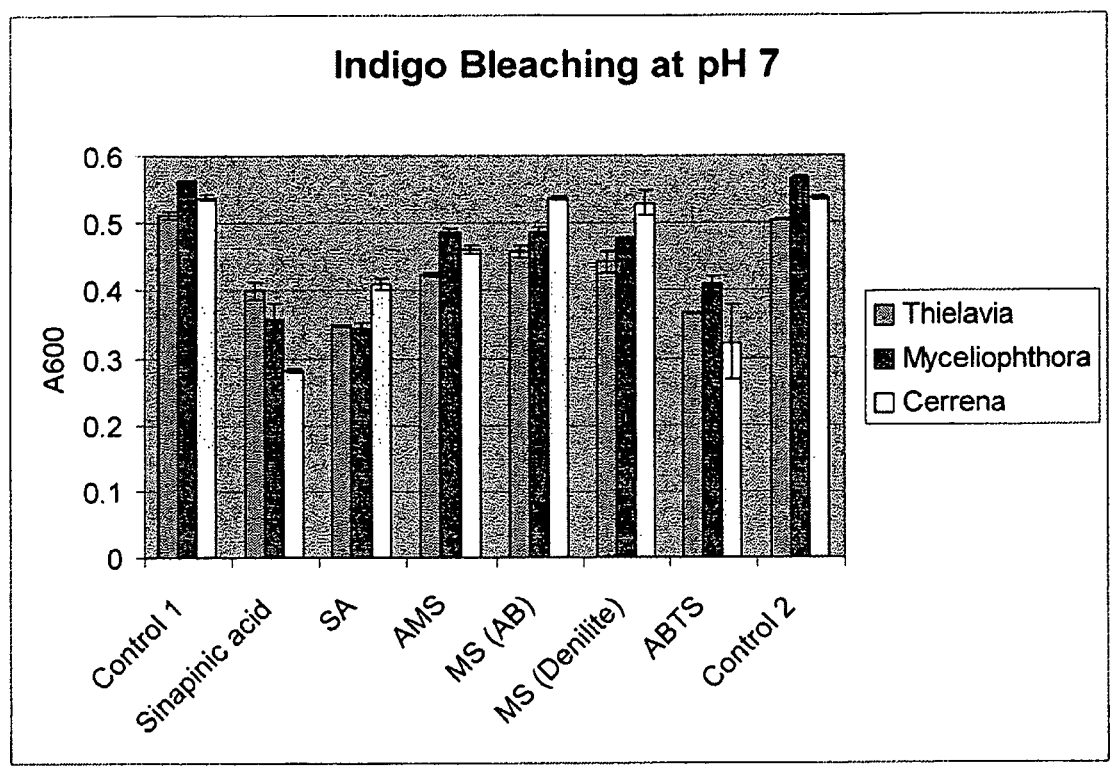
FIG. 9 is a bar graph showing the results of bleaching of soluble indigo using a *Thielavia, Myceliophthora* and *Cerrena* sp. laccase and a variety of mediators at pH 7.

Bleaching of solubilized indigo in 96-well microtitre plates was performed as described in Example 14, using 3 different laccases at pH values of 5 and 7. The mediators used were sinapinic acid, 4-carboxamido-2,6-dimethoxyphenol (SA), methyl 4-acetyl syringate (AMS), methyl syringate (MS) and 2,2'-azino-bis(3-ethylbenzthiazoline-6-sulphonic acid (ABTS). FIGS. 8 and 9 shows the results of soluble indigo bleaching at pH values of 5 and 7 using three laccases derived from Myceliophtora, *Thielavia* and *Cerrena* sp. respectively. These data are tabulated in Tables 2 and 3.

TABLE 2

Change in absorbance at 600 nm relative to a control following bleaching of soluble indigo using laccases from *Thielavia*, *Myceliophtora* and *Cerrena* sp. at pH 5, at a mediator concentration of 250 uM.

| | Laccase | | | | | |
|---|---|---|---|---|---|---|
| | *Thielavia* | | *Myceliophtora* | | *Cerrena* | |
| Mediator | $\Delta A_{600}$ | Std Dev | $\Delta A_{600}$ | Std Dev | $\Delta A_{600}$ | Std Dev |
| Control 1 | 0 | 0.016 | 0 | 0.010 | 0 | 0.005 |
| Sinapinic acid | 0.068 | 0.019 | 0.157 | 0.020 | 0.240 | 0.007 |
| SA | 0.170 | 0.011 | 0.254 | 0.013 | 0.142 | 0.005 |
| AMS | 0.100 | 0.012 | 0.117 | 0.007 | 0.028 | 0.003 |
| MS (AB) | 0.048 | 0.011 | 0.057 | 0.007 | 0.005 | 0.011 |
| MS (Denilite) | 0.050 | 0.013 | 0.061 | 0.007 | 0.043 | 0.013 |
| ABTS | 0.234 | 0.012 | 0.267 | 0.008 | 0.329 | 0.031 |
| Control 2 | −0.007 | 0.017 | −0.011 | 0.007 | −0.006 | 0.005 |

TABLE 3

Change in absorbance at 600 nm relative to a control following bleaching of soluble indigo using laccases from *Thielavia*, *Myceliophtora* and *Cerrena* sp. at pH 7, at a mediator concentration of 250 uM.

| | Laccase | | | | | |
|---|---|---|---|---|---|---|
| | *Thielavia* | | *Myceliophtora* | | *Cerrena* | |
| Mediator | $\Delta A600$ | Std Dev | $\Delta A600$ | Std Dev | $\Delta A600$ | Std Dev |
| Control 1 | 0 | 0.008 | 0 | 0.001 | 0 | 0.006 |
| Sinapinic acid | 0.112 | 0.015 | 0.204 | 0.020 | 0.257 | 0.005 |
| SA | 0.162 | 0.006 | 0.220 | 0.009 | 0.128 | 0.010 |
| AMS | 0.087 | 0.006 | 0.078 | 0.005 | 0.077 | 0.007 |
| MS (AB) | 0.053 | 0.010 | 0.076 | 0.006 | 0.000 | 0.006 |
| MS (Denilite) | 0.069 | 0.017 | 0.086 | 0.001 | 0.008 | 0.018 |
| ABTS | 0.145 | 0.006 | 0.155 | 0.014 | 0.215 | 0.056 |
| Control 2 | 0.007 | 0.006 | −0.004 | 0.001 | 0 | 0.005 |

Example 16

Purification and Determination of Specific Activity

The laccase D optimized gene (SEQ ID NO:70) was expressed using the expression system described in co-pending application U.S. 60/984,430 (Attorney Docket No. GC993P entitled "Signal Sequences and co-expressed chaperones for improved heterologous protein production in a host cell" filed 1 Nov. 2007) in 14 liter fermenters. Fermentation broth from was harvested at 184 hours and concentrated by ultra filtration (UFC 20070245). The concentrate was diafiltered into 25 mM sodium acetate, pH4.0 buffer. Then 500 ml of the diafiltered UFC sample was loaded on to an ion exchange column containing Poros HS-20 resin (Applied Biosystems, 20×275 mm column) equilibrated with 25 mM sodium acetate buffer, pH 4.0. The column was washed with 10 column volumes of 25 mM sodium acetate buffer, pH 4.0. The laccase D protein was eluted from the column using a salt gradient (12 column volumes) from 40 mm to 80 mM sodium chloride in 25 mM sodium acetate buffer, pH 4.0. Fractions containing laccase activity were pooled and further concentrated using an Amicon 400 mL stir cell with a 10K membrane. Total protein was measure by SDS protein gel using BSA as standard as 4 mg/ml (>90% pure). The laccase sample was diluted 10,000 fold with water and stored at RT for 18 hours and at 4° C. for more than 24 hours. ABTS activity was measured as 8570 units/ml. The specific activity of the recombinant laccase D is then calculated by dividing 8570 units/ml by 4 mg/ml resulting in 2140 units/mg of protein which is 100 times more activity than the Stachybotrys laccase (16 u/mg), see Mander et al, Appl. Environ. Microbiol. (2006) 72:5020-5026). Thus, this enzyme results in lower copper discharge into the environment than other laccases, e.g., Stachybotrys laccase, by virtue of the high specific activity.

Example 17

Procedure for Denim Bleaching

Mediators 4-hydroxy-3,5-dimethoxybenzamide (syringamide, SA) was purchased from Punjab Chemicals & Crop Protection Limited (Mumbai, India). 4-hydroxy-3,5-dimethoxybenzonitrile (syringonitrile, SN) was acquired from StereoChemical, Inc., (Newark, Del.) or Punjab Chemicals & Crop Protection Limited (Mumbai, India).

Enzyme

Laccase enzyme, derived from *Cerrena unicolor* (Example 16, 8570 U/ml, 4 mg protein/ml) was used in the experiments.

Procedure

The enzyme incubations were done in an ATLAS LP 2 Launder-O-meter at different conditions in relation to pH, temperature, enzyme concentration and mediator concentration.

Reactions were carried out in 500 ml stainless steel reaction vessels containing 100 ml of liquid. To each vessel five (7×7 cm) stonewashed denim swatches (ACG denim style 80270) and 6 steel balls of 6 mm diameter were added. The reactions vessels were closed and entered into the launder-O-meter that was pre-heated to the desired temperature. The incubation was carried out for 30 minutes after which the swatches were washed with 'running' tap water, spin dried in an AEG IPX4 centrifuge and dried with an Elna Press Electronic iron at program cotton and evaluated.

Stonewashing of Denim

Denim, 12 legs weighing approximately 3 kg, was desized in a Unimac UF 50 washing machine under the following conditions:

Desizing for 15 minutes at 10:1 liquor ratio 50° C. with 0.5 g/l (15 g) of Optisize 160 amylase (Genencor) and 0.5 g/l (15 g) of a non-ionic surfactant (e.g. Rucogen BFA, (Rudolf Chemie) or Ultravon GPN, (Huntsman))

2 cold rinses for 5 minutes at 30:1 liquor ratio.

Following desizing the denim was stonewashed in a Unimac UF 50 washing machine under the following conditions:

Cold rinse for 5 minutes at 10:1 liquor ratio

Stonewashing for 60 minutes at 10:1 liquor ratio 55° C. with 1 kg of pumice stone, citrate buffer (30 g tri-sodium citrate dihydrate and 30 g citric acid monohydrate) and 35 g IndiAge 2XL cellulase (Genencor).

2 cold rinses for 5 minutes at 30:1 liquor ratio.

The denim was dried in a Miele Novotronic T494C household fabric dryer. From the denim legs, swatches of 7×7 cm were cut.

Evaluation of Denim Swatches

The color of the five denim swatches is measured with a Minolta Chromameter CR 310 in the CIE Lab color space with a D 65 light source. Measurements were done before and after laccase treatment and the results of the five swatches were averaged. The total color difference (TCD) is calculated. The total color difference can be calculated with the formula: $TCD = \sqrt{(\Delta L)^2 + (\Delta a)^2 + (\Delta b)^2}$.

Evaluation of Denim Legs

Denim legs were evaluated with a Minolta Chromameter CR 310 in the CIE Lab color space with a D 65 light source. Measurements were done only after laccase treatment. For each denim leg 8 measurements are taken and the result of the 12 legs (96 measurements) was averaged. The total color difference (ΔE) is calculated from the difference between the initial and final CIE L*a*b* values according to the formula $$\Delta E = (\Delta L^2 + \Delta a^2 + \Delta b^2)^{1/2}$$

Example 18

Effect of Temperature on the Recombiant Laccase D Bleaching Performance (Unimac)

Laccase bleaching of stonewashed denim: Denim, 12 legs approximately 3 kg, was desized and stonewashed as described in example 17. After stonewashing a laccase treatment was done in a Unimac UF 50 washing machine according to the following process:

30 minutes at 10:1 liquor ratio,
pH 6 (21 g monosodium phosphate and 5 g adipic acid, laccase D laccase) or pH 4.8 (8.6 g monosodium phosphate and 16.8 g of adipic acid, Novoprime Base 268 laccase)
laccase (laccase D or Novoprime Base 268)
mediator (syringamide (SA) and syringonitrile (SN))
After laccase treatment the denim use rinsed twice in cold water for 5 minutes at 30:1 liquor ratio.

The laccase experiments were carried out and the results are presented in Tables 4 and 5.

TABLE 4

| Laccase D concentration | Mediator | Mediator concentration | Temperature (° C.) | Bleaching level (CIE L) |
|---|---|---|---|---|
| 0.05 g/l/0.4 U/ml | SA | 0.33 mM | 60 | 35.6 |
| 0.05 g/l/0.4 U/ml | SN | 0.47 mM | 60 | 35.9 |
| 0.05 g/l/0.4 U/ml | SA | 0.33 mM | 40 | 35.6 |
| 0.05 g/l/0.4 U/ml | SN | 0.47 mM | 40 | 35.7 |

TABLE 5

| Novoprime base 268 concentration | Mediator concentration | Temperature (° C.) | Bleaching level (CIE L) |
|---|---|---|---|
| 0.05 g/l | 0.023 g/l | 60 | 35.9 |
| 0.05 g/l | 0.023 g/l | 40 | 33.7 |

The recombinant laccase D has better performance at lower temperatures than currently available commercial laccases. The laccase D (in the presence of mediator) provides a bleaching effect at temperatures below 60° C., preferably between 40° C. and 60° C. Thus, the laccase may provide an energy benefit to the textile processor.

Example 19

Effect of Recombinant Laccase Enzyme and Mediator Concentration on Bleaching Performance (Launder-O-Meter)

The effect of laccase and mediator concentration was evaluated running the experiments in the table below at pH 6 (50 mM monosodium phosphate buffer pH adjusted with sodium hydroxide 4N solution) and a temperature of 60° C.

The experiments were done with syringamide (SA)— and syringonitrile (SN) mediator.

100 ml buffer was added to a beaker with five swatches, 7×7 cm. The total weight 12 g, (denim:liquor ratio=1:8). Laccase and mediator concentrations were used as indicated in the tables below.

TABLE 6

| Laccase enzyme concentration (μl/l) | Activity correspondence (Laccase unit/g denim) |
|---|---|
| 10 | 0.67 |
| 33 | 2.17 |
| 55 | 3.67 |
| 78 | 5.17 |
| 100 | 6.67 |

TABLE 7

| Mediator Concentration (mM) |
|---|
| 0.10 |
| 0.33 |
| 0.55 |
| 0.78 |
| 1.00 |

The amounts of syringamide or syringonitrile mediator as indicated in the tables below were added to each beaker as a dilution of a 275 mM SA— or —SN stock solution in 98% methanol. The laccase was added to each beaker as indicated in the tables below, as dilution of a 400 units/ml laccase stock solution. The beakers were closed and processed at 60° C. as described in the example 17. The swatches were evaluated as described in example 17.

TABLE 8

LACCASE + SA at 60° C. pH 6

| Laccase (μl/l) | Mediator syringamide (mM) | TCD |
|---|---|---|
| 100 | 1.00 | 5.6 |
| 100 | 1.00 | 6.0 |
| 100 | 0.10 | 2.9 |
| 78 | 0.33 | 4.4 |
| 55 | 1.00 | 6.2 |
| 55 | 0.55 | 5.3 |
| 33 | 0.78 | 5.5 |
| 33 | 0.33 | 4.6 |
| 10 | 1.00 | 3.2 |
| 10 | 0.10 | 2.5 |
| 55 | 0.55 | 5.8 |
| 100 | 0.55 | 5.3 |
| 78 | 0.78 | 5.9 |
| 100 | 0.10 | 3.2 |
| 55 | 0.10 | 3.1 |
| 10 | 0.55 | 3.6 |

TCD = total color difference

TABLE 9

LACCASE + SN at 60° C. pH 6

| Laccase (μl/l) | Mediator syringonitrile (mM) | TCD |
|---|---|---|
| 100 | 1.00 | 7.6 |
| 100 | 1.00 | 8.1 |
| 100 | 0.10 | 4.1 |

TABLE 9-continued

LACCASE + SN at 60° C. pH 6

| Laccase (µl/l) | Mediator syringonitrile (mM) | TCD |
|---|---|---|
| 78 | 0.33 | 5.6 |
| 55 | 1.00 | 7.0 |
| 55 | 0.55 | 6.0 |
| 33 | 0.78 | 5.5 |
| 33 | 0.33 | 4.4 |
| 10 | 1.00 | 3.8 |
| 10 | 0.10 | 2.7 |
| 55 | 0.55 | 6.3 |
| 100 | 0.55 | 7.1 |
| 78 | 0.78 | 7.1 |
| 100 | 0.10 | 4.0 |
| 55 | 0.10 | 3.5 |
| 10 | 0.55 | 3.4 |

TCD = total color difference

Figure 10:
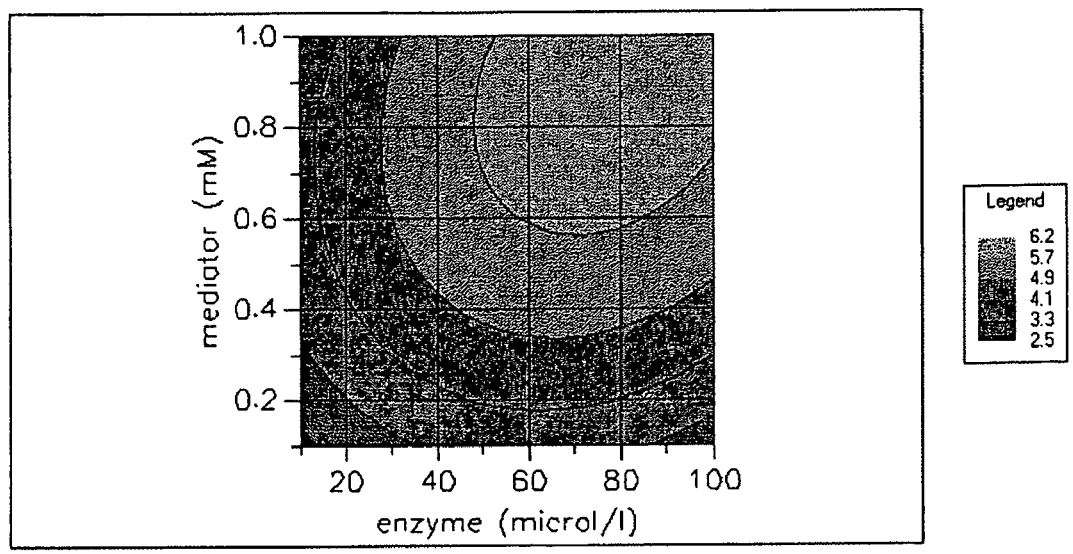
FIG. 10 is a total color difference graph for the recombinant laccase D and syringamide mediator as a function of mediator concentration and enzyme concentration at 60° C. and pH 6.
Figure 11:
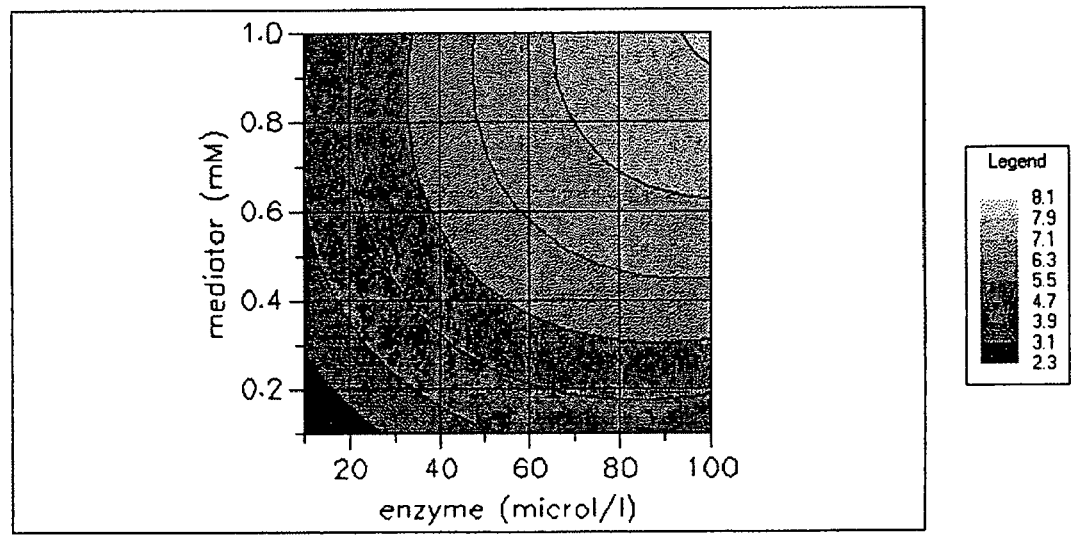
FIG. 11 is a total color difference graph for the recombinant laccase D and syringonitrile mediator as a function of mediator concentration and enzyme concentration at 60° C. and pH 6.

The above Tables and FIGS. 10 and 11 show that you need both enzyme and mediator to get bleaching. Also it shows there is some flexibility in the enzyme/mediator ratio in achieving a certain bleaching level.

Example 20

Recombinant Laccase D Dose Response Effect on the Bleaching Performance (Unimac)

Laccase bleaching of stonewashed denim—Denim, 12 legs weighing approximately 3 kg, was desized and stonewashed as described in Example 17. After stonewashing, a laccase treatment was done according to the following process: 30 minutes at 10:1 liquor ratio and pH 6 (21 g monosodium phosphate and 5 g adipic acid) and 60° C. with laccase and mediator. After laccase treatment the denim use rinsed twice in cold water for 5 minutes at 30:1 liquor ratio.

The following experiments were carried out.
Syringamide 0.33 mM:

| *Cerrena unicolor* laccase concentration (g/l) | Bleaching level (CIE L) |
|---|---|
| 0.010 | 34.6 |
| 0.05 | 36.2 |
| 0.25 | 36.2 |

Syringonitrile 0.39 mM:

| Laccase D concentration (g/l) | Bleaching level (CIE L) |
|---|---|
| 0.25 | 37.7 |
| 0.4 | 39.5 |
| 0.53 | 38.8 |

The results are shown in the above tables. This shows that with recombinant laccase D and the amide mediator the bleaching level flattens quite quickly. With an enzyme concentration of 0.05 and 0.25 the same bleaching level is obtained. For the recombinant laccase D and the nitrile mediator the bleaching level increases up to 0.4 g/l, where there appears to be an optimum.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

The invention claimed is:

1. A recombinant laccase having the amino acid sequence of SEQ ID NO: 14 or having an amino acid sequence that is at least 95% identical to SEQ ID NO: 14.

2. The recombinant laccase of claim 1, wherein the laccase is at least 98% identical to SEQ ID NO: 14.

* * * * *